(12) United States Patent
Brotherton-Pleiss et al.

(10) Patent No.: US 8,742,098 B2
(45) Date of Patent: Jun. 3, 2014

(54) INHIBITORS OF BRUTON'S TYROSINE KINASE

(71) Applicant: Hoffmann-La Roche Inc., Nutley, NJ (US)

(72) Inventors: Christine E. Brotherton-Pleiss, Sunnyvale, CA (US); Francisco Javier Lopez-Tapia, Mahwah, NJ (US); Yan Lou, Fremont, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/706,399

(22) Filed: Dec. 6, 2012

(65) Prior Publication Data

US 2013/0150360 A1 Jun. 13, 2013

Related U.S. Application Data

(60) Provisional application No. 61/568,675, filed on Dec. 9, 2011.

(51) Int. Cl.
*C07D 413/14* (2006.01)
*A61K 31/5377* (2006.01)

(52) U.S. Cl.
CPC .......... *C07D 413/14* (2013.01); *A61K 31/5377* (2013.01)
USPC ....................................... 544/119; 514/234.5

(58) Field of Classification Search
CPC .......................... C07D 413/14; A61K 31/5377
USPC ....................................... 544/119; 514/234.5
See application file for complete search history.

(56) References Cited

U.S. PATENT DOCUMENTS

| | | | |
|---|---|---|---|
| 7,902,194 B2 | 3/2011 | Dewdney et al. | |
| 8,124,604 B2 | 2/2012 | Dewdney et al. | |
| 8,299,077 B2 | 10/2012 | Berthel et al. | |
| 8,324,211 B2 * | 12/2012 | Dewdney et al. | 514/252.01 |
| 2009/0186898 A1 | 7/2009 | Dewdney et al. | |

FOREIGN PATENT DOCUMENTS

| | | |
|---|---|---|
| WO | 2010/006947 | 1/2010 |
| WO | 2010/006970 | 1/2010 |

OTHER PUBLICATIONS (International Search Report in PCT EP2012/074581 Mar 6, 2013).
Rastetter et al., Annu Rev Med 55:477-503 ( 2004).
Hunter, Cell 50:823-829 ( 1987).
Islam and Smith, Immunol. Rev. 178:49-63 ( 2000).
Lindvall et al., Immunol. Rev. 203:200-215 ( 2005).
Jansson and Holmdahl, Clin. Exp. Immunol. 94:459-465 ( 1993).
Horwood et al., J. Exp. Med. 197:1603-1611 ( 2003).
Rosen et al., New Eng. J. Med. 333:431 ( 1995).
Khan et al., Immunity 3:283-299 ( 1995).
Vassilev et al., J. Biol. Chem. 274:1646-1656 ( 1998).
Ellmeier et al., J. Exp. Med. 192:1611-1623 ( 2000).
Pan et al., Chem. Med. Chem. 2:58-61 ( 2007).
Feldhahn et al., J. Exp. Med. 201:1837-1852 ( 2005).
Iwaki et al., J. Biol. Chem. 280:40261-40270 ( 2005).

* cited by examiner

*Primary Examiner* — Robert Havlin

(57) ABSTRACT

This application discloses compounds according to generic Formula I:

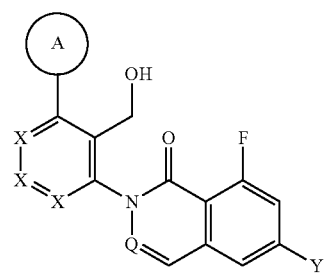

wherein the variables are defined as described herein, and which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation, such as rheumatoid arthritis. Also disclosed are compositions containing compounds of Formula I and at least one carrier, diluent or excipient.

20 Claims, No Drawings

INHIBITORS OF BRUTON'S TYROSINE KINASE

PRIORITY TO RELATED APPLICATIONS

This application is entitled to the benefit of U.S. provisional patent application Ser. No. 61/568,675 filed on Dec. 9, 2011.

FIELD OF THE INVENTION

The present invention relates to the use of novel derivatives which inhibit Btk and are useful for the treatment of autoimmune and inflammatory diseases caused by aberrant B-cell activation. The novel compounds described herein are useful for the treatment of rheumatoid arthritis and asthma.

Protein kinases constitute one of the largest families of human enzymes and regulate many different signaling processes by adding phosphate groups to proteins (T. Hunter, *Cell* 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. *Annu Rev Med* 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. *Immunity* 1995 3:283; Ellmeier et al. *J. Exp. Med.* 2000 192:1611). Mutation of Btk in humans leads to the condition X-linked agammaglobulinemia (XLA) (reviewed in Rosen et al. *New Eng. J. Med.* 1995 333:431 and Lindvall et al. *Immunol. Rev.* 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Z. Pan et al., *Chem. Med Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J. Biol. Chem.* 2005 280:40261). This shows Btk could be useful to treat pathological mast cells responses such as allergy and asthma. Also monocytes from XLA patients, in which Btk activity is absent, show decreased TNF alpha production following stimulation (Horwood et al. *J Exp Med* 197:1603, 2003). Therefore TNF alpha mediated inflammation could be modulated by small molecular Btk inhibitors. Also, Btk has been reported to play a role in apoptosis (Islam and Smith *Immunol. Rev.* 2000 178:49,) and thus Btk inhibitors would be useful for the treatment of certain B-cell lymphomas and leukemias (Feldhahn et al. *J. Exp. Med.* 2005 201:1837).

SUMMARY OF THE INVENTION

The present application provides the Btk inhibitor compounds of Formula I, methods of use thereof, as described herein below:

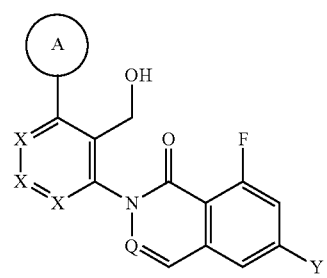

I wherein:

each X is CH or N;

Q is CH or N;

A is

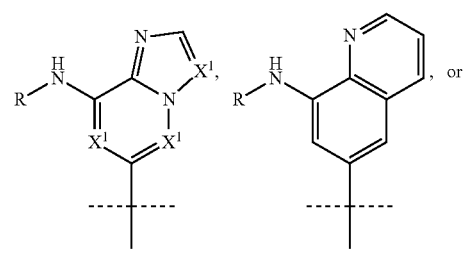

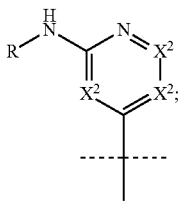

wherein:
one $X^1$ is N and the rest are CH, or each $X^1$ is CH;
one $X^2$ is N and the rest are CH, or each $X^2$ is CH, or one $X^2$ is N and the rest are CH or $CNH_2$;
R is H, —$R^1$, —$R^1$—$R^2$—$R^3$, —$R^1$—$R^3$, or —$R^2$—$R^3$;
  $R^1$ is aryl, heteroaryl, bicyclic heteroaryl, cycloalkyl, heterocycloalkyl, or bicyclic heterocycle, each of which is optionally substituted with one or more lower alkyl, hydroxy, hydroxy lower alkyl, lower alkoxy, halo, nitro, amino, amido, cyano, oxo, or lower haloalkyl;
  $R^2$ is —C(=O), —C(=O)O, —C(=O)$NR^{2'}$, —NHC(=O)O, —C($R^{2'}$)$_2$, —O, —S, —C(=NH)$NR^{2'}$, or —S(=O)$_2$;
  each $R^{2'}$ is independently H or lower alkyl;
  $R^3$ is H or $R^4$;
  $R^4$ is lower alkyl, lower haloalkyl, lower alkoxy, amino, lower alkyl amino, cycloalkyl amino, lower dialkyl amino, aryl, arylalkyl, alkylaryl, heteroaryl, lower alkyl heteroaryl, heteroaryl lower alkyl, cycloalkyl, lower alkyl cycloalkyl, cycloalkyl lower alkyl, heterocycloalkyl, lower alkyl heterocycloalkyl, heterocycloalkyl lower alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;
Y is H, halo, $Y^1$, $Y^2$, or $Y^3$;
  $Y^1$ is lower alkyl, optionally substituted with one or more substituents selected from the group consisting of lower haloalkyl, halogen, hydroxy, amino, cyano, and lower alkoxy;
  $Y^2$ is lower cycloalkyl, optionally substituted with one or more substituents selected from the group consisting of lower alkyl, lower haloalkyl, halogen, hydroxy, amino, cyano, and lower alkoxy; and
  $Y^3$ is amino, optionally substituted with one or more lower alkyl, alkoxy lower alkyl, or hydroxy lower alkyl;
or a pharmaceutically acceptable salt thereof.

The application provides a method for treating an inflammatory and/or autoimmune condition comprising administering to a patient in need thereof a therapeutically effective amount of the Btk inhibitor compound of Formula I.

The application provides a pharmaceutical composition comprising the Btk inhibitor compound of any one of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "- - -" drawn through a bond each refer to the point of attachment of a functional group or other chemical moiety to the rest of the molecule of which it is a part. Thus, for example:

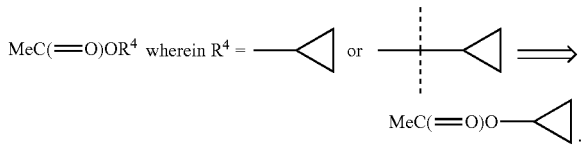

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of Formulae I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)₂R wherein R is "heteroalkyl" as defined herein.

The terms "alkylsulfonylamino" and "arylsulfonylamino" as used herein refers to a group of formula —NR'S(=O)₂R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO₂H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, 4,5,6,7-tetrahydro-pyrazolo[1,5-a]pyrazin-2-yl, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or S(O)₀₋₂), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of Btk

This application is related to U.S. patent application Ser. No. 12/316,343, filed Dec. 11, 2008, U.S. Pat. No. 7,902,194, filed on Jun. 24, 2009, U.S. patent application Ser. No. 12/460,226, filed Jul. 15, 2009, U.S. patent application Ser. No. 12/711,312, filed on Feb. 24, 2010, and U.S. patent application Ser. No. 12/978, 187, filed on Jan. 10, 2011, the disclosures of which are incorporated herein by reference in its entirety.

The application provides a compound of Formula I,

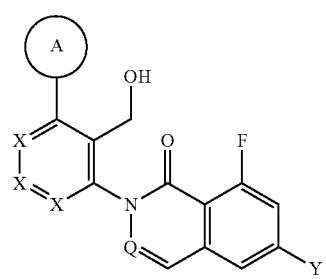

I wherein:
each X is CH or N;
Q is CH or N;
A is

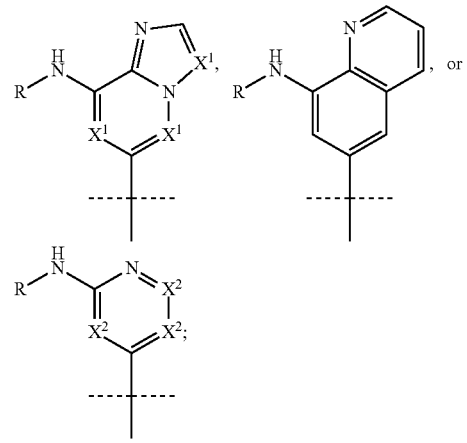

wherein:
one $X^1$ is N and the rest are CH, or each $X^1$ is CH;
one $X^2$ is N and the rest are CH, or each $X^2$ is CH, or one $X^2$ is N and the rest are CH or CNH₂;
R is H, —R¹, —R¹—R²—R³, —R¹—R³, or —R²—R³;
R¹ is aryl, heteroaryl, bicyclic heteroaryl, cycloalkyl, heterocycloalkyl, or bicyclic heterocycle, each of which is optionally substituted with one or more lower alkyl, hydroxy, hydroxy lower alkyl, lower alkoxy, halo, nitro, amino, amido, cyano, oxo, or lower haloalkyl;
R² is —C(=O), —C(=O)O, —C(=O)NR²', —NHC(=O)O, —C(R²')₂, —O, —S, —C(=NH)NR²', or —S(=O)₂;

each $R^{2'}$ is independently H or lower alkyl;

$R^3$ is H or $R^4$;

$R^4$ is lower alkyl, lower haloalkyl, lower alkoxy, amino, lower alkyl amino, cycloalkyl amino, lower dialkyl amino, aryl, arylalkyl, alkylaryl, heteroaryl, lower alkyl heteroaryl, heteroaryl lower alkyl, cycloalkyl, lower alkyl cycloalkyl, cycloalkyl lower alkyl, heterocycloalkyl, lower alkyl heterocycloalkyl, heterocycloalkyl lower alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;

Y is H, halo, $Y^1$, $Y^2$, or $Y^3$;

$Y^1$ is lower alkyl, optionally substituted with one or more substituents selected from the group consisting of lower haloalkyl, halogen, hydroxy, amino, cyano, and lower alkoxy;

$Y^2$ is lower cycloalkyl, optionally substituted with one or more substituents selected from the group consisting of lower alkyl, lower haloalkyl, halogen, hydroxy, amino, cyano, and lower alkoxy; and $Y^3$ is amino, optionally substituted with one or more lower alkyl, alkoxy lower alkyl, or hydroxy lower alkyl;

or a pharmaceutically acceptable salt thereof.

The application provides a compound of Formula I, wherein A is

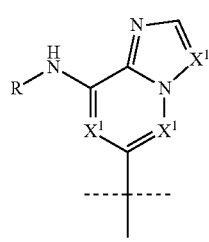

The application provides a compound of Formula I, wherein A is

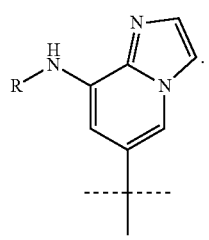

The application provides a compound of Formula I, wherein A is

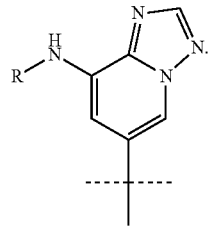

The application provides a compound of Formula I, wherein A is

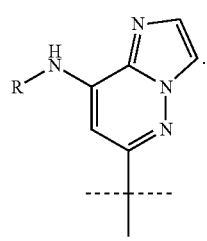

The application provides a compound of Formula I, wherein A is

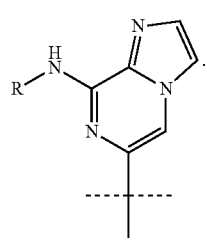

The application provides a compound of Formula I, wherein A is

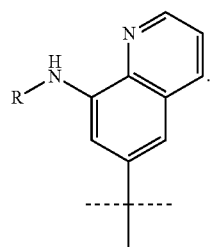

The application provides a compound of Formula I, wherein A is

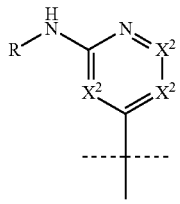

The application provides a compound of Formula I, wherein A is

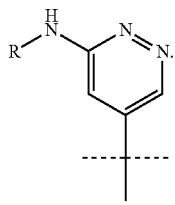

The application provides a compound of Formula I, wherein A is

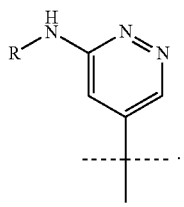

The application provides a compound of Formula I, wherein R is —$R^1$—$R^2$—$R^3$.

The application provides a compound of Formula I, wherein $R^1$ is pyridyl, each X is CH, and Q is N.

The application provides a compound of Formula I, wherein $R^1$ is pyridyl, one X is N, and Q is N.

The application provides a compound of Formula I, wherein $R^2$ is —C(=O) or $CH_2$.

The application provides a compound of Formula I, wherein R is —$R^1$—$R^3$, each X is CH, and Q is N.

The application provides a compound of Formula I selected from the group consisting of:

6-tert-Butyl-8-fluoro-2-(2-hydroxymethyl-3-{8-[5-(morpholine-4-carbonyl)-pyridin-2-ylamino]-[1,2,4]triazolo[1,5-c]pyridin-6-yl}-phenyl)-2H-phthalazin-1-one;

6-tert-Butyl-8-fluoro-2-(2-hydroxymethyl-3-{8-[5-(morpholine-4-carbonyl)-pyridin-2-ylamino]-imidazo[1,2-b]pyridazin-6-yl}-phenyl)-2H-phthalazin-1-one;

6-tert-Butyl-8-fluoro-2-(2-hydroxymethyl-3-{8-[5-(4-isopropyl-piperazin-1-yl)-pyridin-2-ylamino]-imidazo[1,2-b]pyridazin-6-yl}-phenyl)-2H-phthalazin-1-one;

6-tert-Butyl-8-fluoro-2-(2-hydroxymethyl-3-{8-[5-(4-methyl-piperazin-1-ylmethyl)-pyridin-2-ylamino]-imidazo[1,2-b]pyridazin-6-yl}-phenyl)-2H-phthalazin-1-one;

6-tert-Butyl-8-fluoro-2-(2-hydroxymethyl-3-{6-[5-(morpholine-4-carbonyl)-pyridin-2-ylamino]-pyridazin-4-yl}-phenyl)-2H-phthalazin-1-one;

6-tert-Butyl-8-fluoro-2-(2-hydroxymethyl-3-{2-[5-(morpholine-4-carbonyl)-pyridin-2-ylamino]-pyridin-4-yl}-phenyl)-2H-phthalazin-1-one;

6-tert-Butyl-8-fluoro-2-(2-hydroxymethyl-3-{8-[4-(morpholine-4-carbonyl)-phenylamino]-imidazo[1,2-c]pyrazin-6-yl}-phenyl)-2H-phthalazin-1-one;

6-tert-Butyl-8-fluoro-2-(2-hydroxymethyl-3-{8-[4-(1-methyl-piperidin-4-yl)-phenylamino]-imidazo[1,2-c]pyrazin-6-yl}-phenyl)-2H-phthalazin-1-one;

6-tert-Butyl-8-fluoro-2-(2-hydroxymethyl-3-{8-[4-(morpholine-4-carbonyl)-phenylamino]-imidazo[1,2-c]pyridin-6-yl}-phenyl)-2H-phthalazin-1-one;

6-tert-Butyl-8-fluoro-2-(2-hydroxymethyl-3-{8-[5-(morpholine-4-carbonyl)-pyridin-2-ylamino]-imidazo[1,2-c]pyridin-6-yl}-phenyl)-2H-phthalazin-1-one;

6-tert-Butyl-8-fluoro-2-{2-hydroxymethyl-3-[8-(1'-methyl-1',2',3',4',5',6'-hexahydro-[3,4']bipyridinyl-6-ylamino)-imidazo[1,2-c]pyridin-6-yl]-phenyl}-2H-phthalazin-1-one;

6-tert-Butyl-8-fluoro-2-(2-hydroxymethyl-3-{6-[5-(morpholine-4-carbonyl)-pyridin-2-ylamino]-pyrimidin-4-yl}-phenyl)-2H-phthalazin-1-one; and 6-tert-Butyl-8-fluoro-2-(2-hydroxymethyl-3-{8-[5-(morpholine-4-carbonyl)-pyridin-2-ylamino]-quinolin-6-yl}-phenyl)-2H-phthalazin-1-one.

The application provides a method for treating an inflammatory and/or autoimmune condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a pharmaceutical composition comprising the compound of Formula I.

The application provides a pharmaceutical composition comprising the compound of Formula I, admixed with at least one pharmaceutically acceptable carrier, excipient or diluent.

The application provides a use of the compound of formula I in the manufacture of a medicament for the treatment of an inflammatory disorder.

The application provides a use of the compound of formula I in the manufacture of a medicament for the treatment of an autoimmune disorder.

The application provides a use of the compound of formula I in the manufacture of a medicament for the treatment of rheumatoid arthritis.

The application provides a use of the compound of formula I in the manufacture of a medicament for the treatment of asthma.

The application provides a compound, method, or composition as described herein.

Btk Inhibitor Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridazinone compounds according to generic Formula I:

TABLE I

| Compound | Nomenclature | Structure |
| --- | --- | --- |
| I-1 | 6-tert-Butyl-8-fluoro-2-(2-hydroxymethyl-3-{8-[5-(morpholine-4-carbonyl)-pyridin-2-ylamino]-[1,2,4]triazolo[1,5-a]pyridin-6-yl}-phenyl)-2H-phthalazin-1-one | 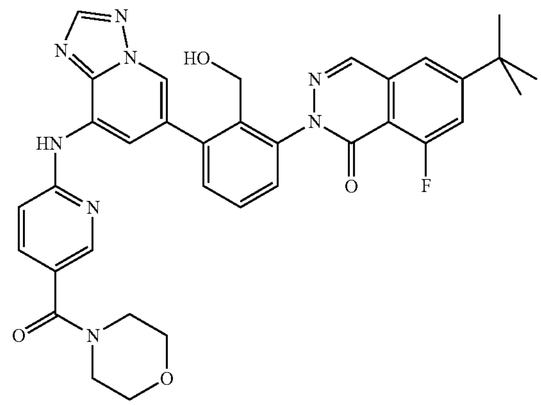 [SMILES: CC(C)(C)c1cc(F)c2c(=O)n(-c3cccc(-c4cc(Nc5ccc(C(=O)N6CCOCC6)cn5)c5ncnn5c4)c3CO)ncc2c1] |
| I-2 | 6-tert-Butyl-8-fluoro-2-(2-hydroxymethyl-3-{8-[5-(morpholine-4-carbonyl)-pyridin-2-ylamino]-imidazo[1,2-b]pyridazin-6-yl}-phenyl)-2H-phthalazin-1-one | 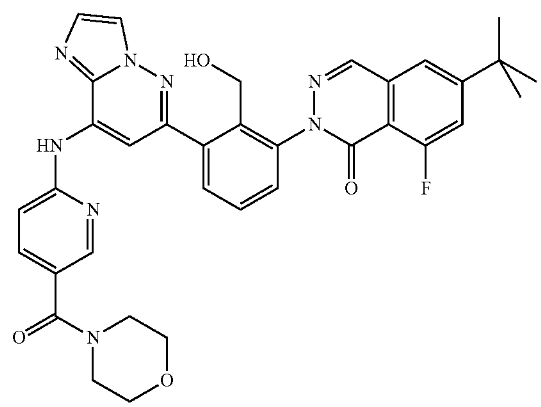 [SMILES: CC(C)(C)c1cc(F)c2c(=O)n(-c3cccc(-c4cc(Nc5ccc(C(=O)N6CCOCC6)cn5)c5nccn5n4)c3CO)ncc2c1] |
| I-3 | 6-tert-Butyl-8-fluoro-2-(2-hydroxymethyl-3-{8-[5-(4-isopropyl-piperazin-1-yl)-pyridin-2-ylamino]-imidazo[1,2-b]pyridazin-6-yl}-phenyl)-2H-phthalazin-1-one | 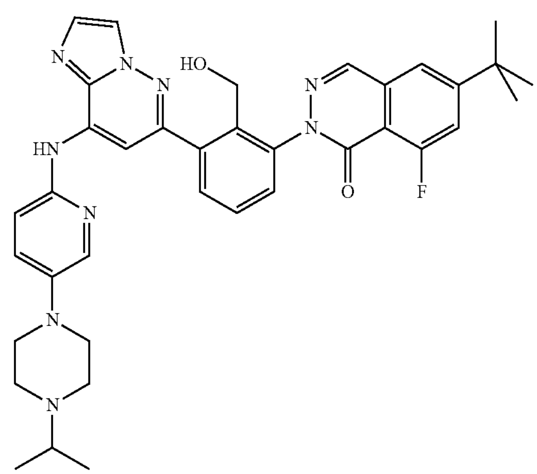 [SMILES: CC(C)N1CCN(c2ccc(Nc3cc(-c4cccc(-n5ncc6cc(C(C)(C)C)cc(F)c6c5=O)c4CO)nn4ccnc34)nc2)CC1] |

TABLE I-continued

| Compound | Nomenclature | Structure |
|---|---|---|
| I-4 | 6-tert-Butyl-8-fluoro-2-(2-hydroxymethyl-3-{8-[5-(4-methyl-piperazin-1-ylmethyl)-pyridin-2-ylamino]-imidazo[1,2-b]pyridazin-6-yl}-phenyl)-2H-phthalazin-1-one | 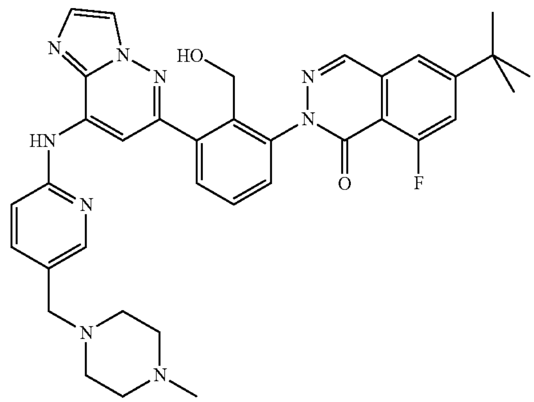 [SMILES: CN1CCN(Cc2ccc(Nc3cc(-c4cccc(-n5ncc6cc(C(C)(C)C)cc(F)c6c5=O)c4CO)nn4ccnc34)nc2)CC1] |
| I-5 | 6-tert-Butyl-8-fluoro-2-(2-hydroxymethyl-3-{6-[5-(morpholine-4-carbonyl)-pyridin-2-ylamino]-pyridazin-4-yl}-phenyl)-2H-phthalazin-1-one | 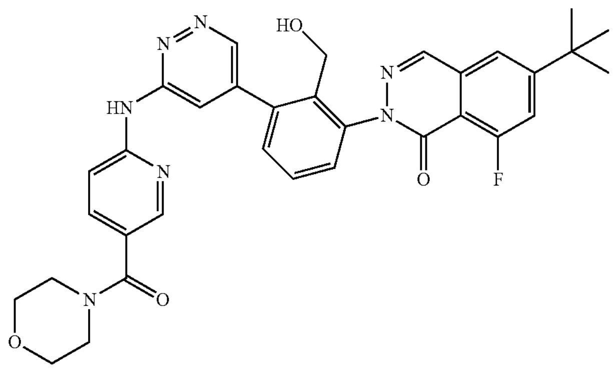 [SMILES: CC(C)(C)c1cc(F)c2c(=O)n(-c3cccc(-c4cnnc(Nc5ccc(C(=O)N6CCOCC6)cn5)c4)c3CO)ncc2c1] |
| I-6 | 6-tert-Butyl-8-fluoro-2-(2-hydroxymethyl-3-{2-[5-(morpholine-4-carbonyl)-pyridin-2-ylamino]-pyridin-4-yl}-phenyl)-2H-phthalazin-1-one | 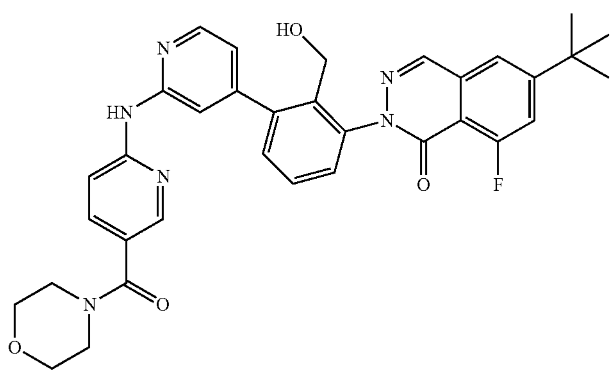 [SMILES: CC(C)(C)c1cc(F)c2c(=O)n(-c3cccc(-c4ccnc(Nc5ccc(C(=O)N6CCOCC6)cn5)c4)c3CO)ncc2c1] |
| I-7 | 6-tert-Butyl-8-fluoro-2-(2-hydroxymethyl-3-{8-[4-(morpholine-4-carbonyl)-phenylamino]-imidazo[1,2-a]pyrazin-6-yl}-phenyl)-2H-phthalazin-1-one | 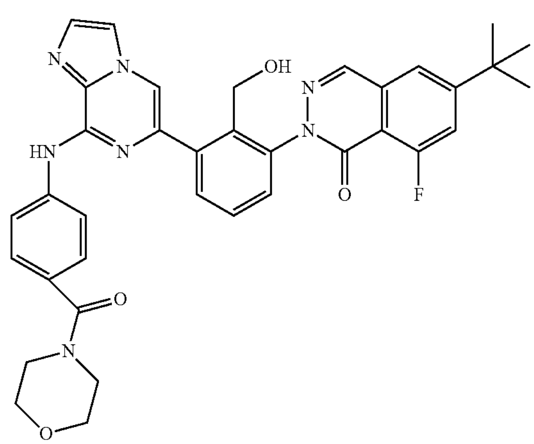 [SMILES: CC(C)(C)c1cc(F)c2c(=O)n(-c3cccc(-c4cn5ccnc5c(Nc5ccc(C(=O)N6CCOCC6)cc5)n4)c3CO)ncc2c1] |

TABLE I-continued

| Compound | Nomenclature | Structure |
|---|---|---|
| I-8 | 6-tert-Butyl-8-fluoro-2-(2-hydroxymethyl-3-{8-[4-(1-methyl-piperidin-4-yl)-phenylamino]-imidazo[1,2-a]pyrazin-6-yl}-phenyl)-2H-phthalazin-1-one | 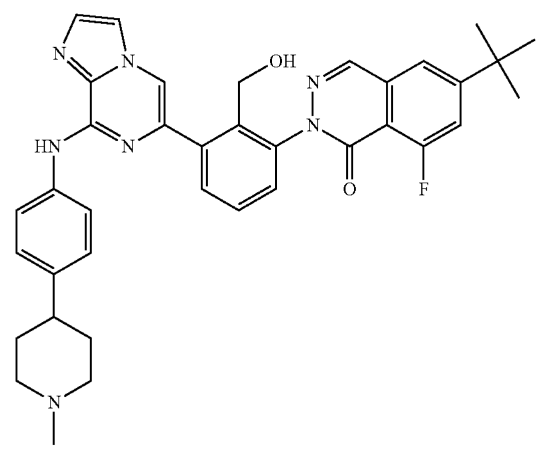 [SMILES: CN1CCC(c2ccc(Nc3nc(-c4cccc(-n5ncc6cc(C(C)(C)C)cc(F)c6c5=O)c4CO)cn4ccnc34)cc2)CC1] |
| I-9 | 6-tert-Butyl-8-fluoro-2-(2-hydroxymethyl-3-{8-[4-(morpholine-4-carbonyl)-phenylamino]-imidazo[1,2-a]pyridin-6-yl}-phenyl)-2H-phthalazin-1-one | 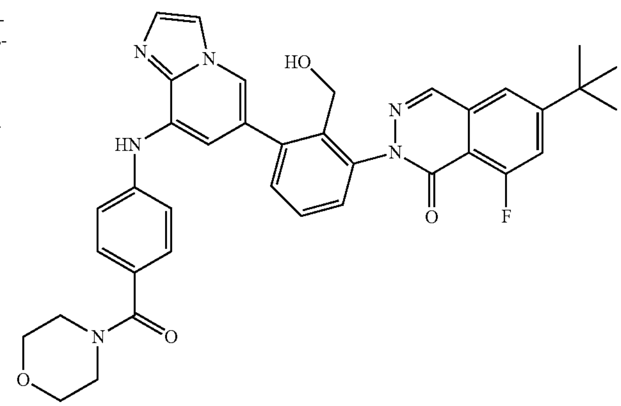 |
| I-10 | 6-tert-Butyl-8-fluoro-2-(2-hydroxymethyl-3-{8-[5-(morpholine-4-carbonyl)-pyridin-2-ylamino]-imidazo[1,2-a]pyridin-6-yl}-phenyl)-2H-phthalazin-1-one | 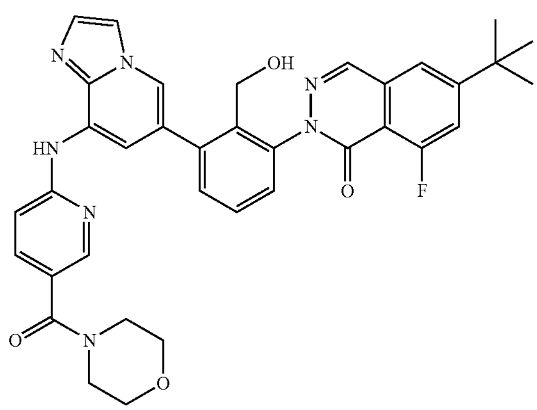 [SMILES: CC(C)(C)c1cc(F)c2c(=O)n(-c3cccc(-c4cc(Nc5ccc(C(=O)N6CCOCC6)cn5)c5nccn5c4)c3CO)ncc2c1] |

TABLE I-continued

| Compound | Nomenclature | Structure |
|---|---|---|
| I-11 | 6-tert-Butyl-8-fluoro-2-{2-hydroxymethyl-3-[8-(1'-methyl-1',2',3',4',5',6'-hexahydro-[3,4']bipyridinyl-6-ylamino)-imidazo[1,2-a]pyridin-6-yl]-phenyl}-2H-phthalazin-1-one WARNING 5: Please note: Alphabetic order of prefixes ignored while numbering a ring | 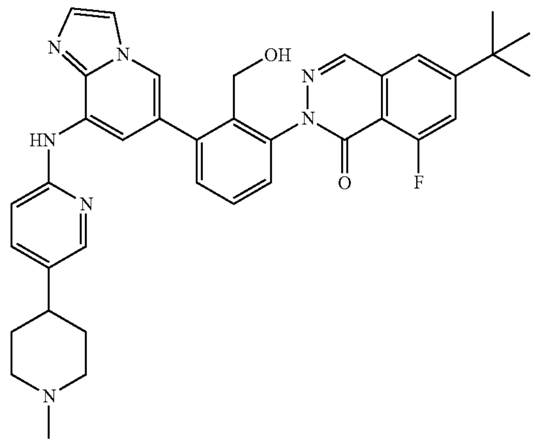 [SMILES: CN1CCC(c2ccc(Nc3cc(-c4cccc(-n5ncc6cc(C(C)(C)C)cc(F)c6c5=O)c4CO)cn4ccnc34)nc2)CC1] |
| I-12 | 6-tert-Butyl-8-fluoro-2-(2-hydroxymethyl-3-{6-[5-(morpholine-4-carbonyl)-pyridin-2-ylamino]-pyrimidin-4-yl}-phenyl)-2H-phthalazin-1-one | 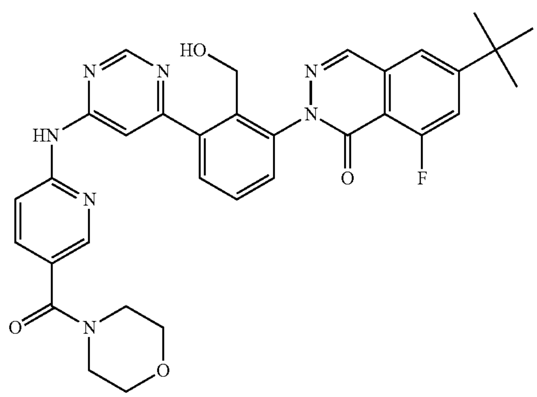 [SMILES: CC(C)(C)c1cc(F)c2c(=O)n(-c3cccc(-c4cc(Nc5ccc(C(=O)N6CCOCC6)cn5)ncn4)c3CO)ncc2c1] |
| I-13 | 6-tert-Butyl-8-fluoro-2-(2-hydroxymethyl-3-{8-[5-(morpholine-4-carbonyl)-pyridin-2-ylamino]-quinolin-6-yl}-phenyl)-2H-phthalazin-1-one | 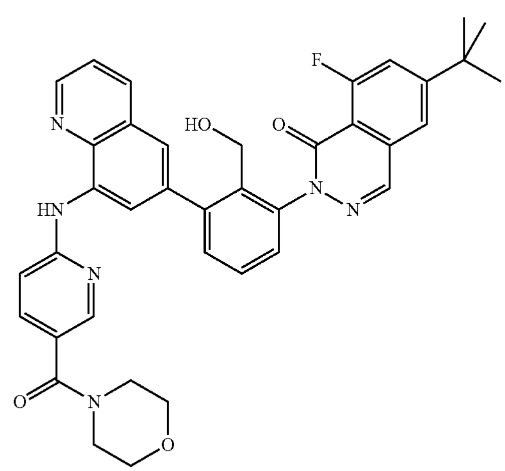 [SMILES: CC(C)(C)c1cc(F)c2c(=O)n(-c3cccc(-c4cc(Nc5ccc(C(=O)N6CCOCC6)cn5)c5ncccc5c4)c3CO)ncc2c1] |

Synthesis
General Synthetic Schemes
Scheme 1.
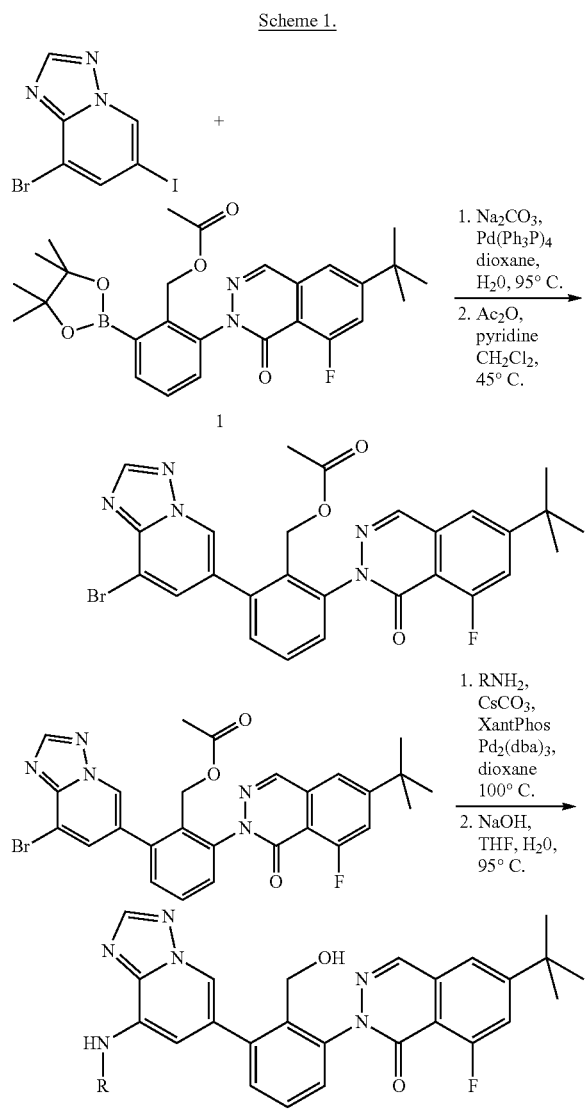
Scheme 2.
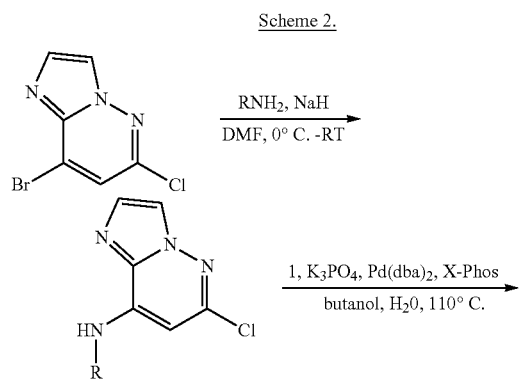
Scheme 3.
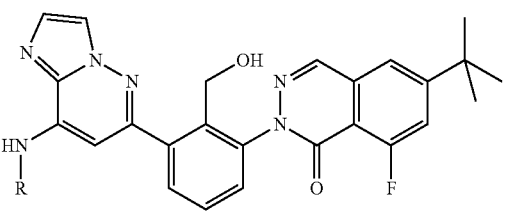
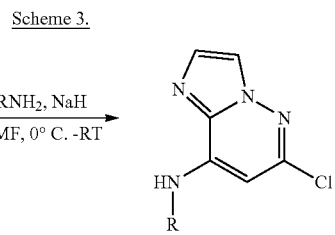
Scheme 4.
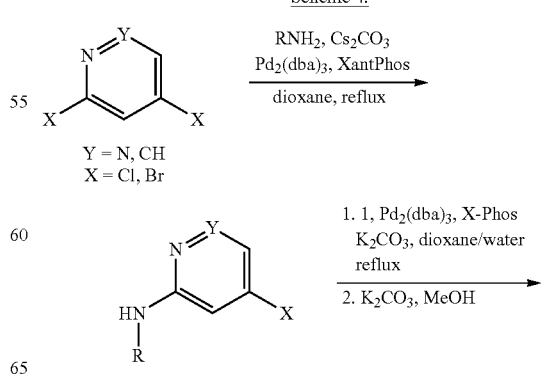
Y = N, CH
X = Cl, Br

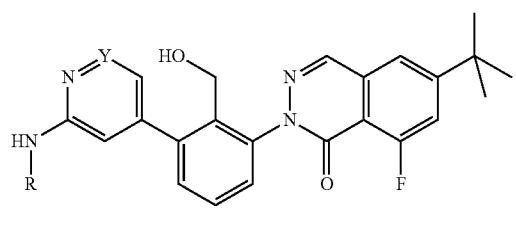
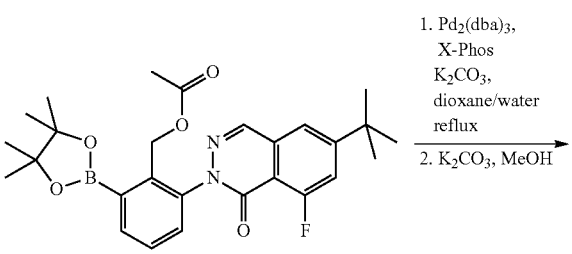
Scheme 5.
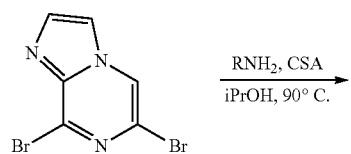
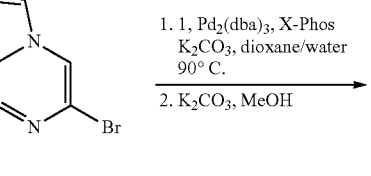
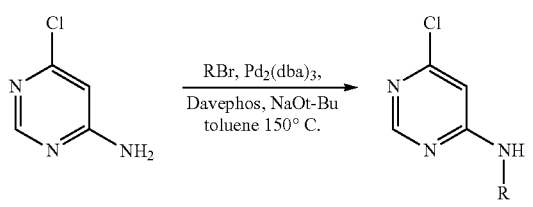
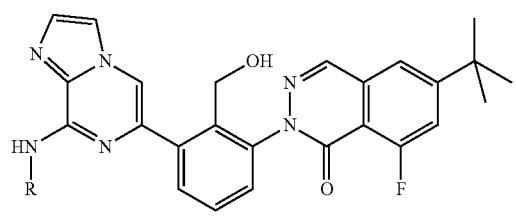
Scheme 7.
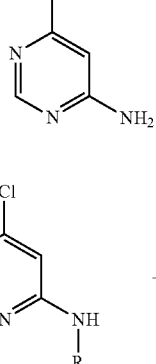
+
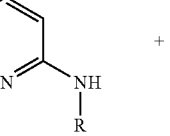
Scheme 6.
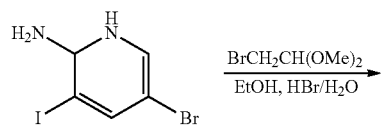
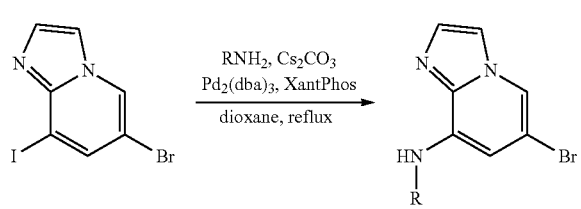
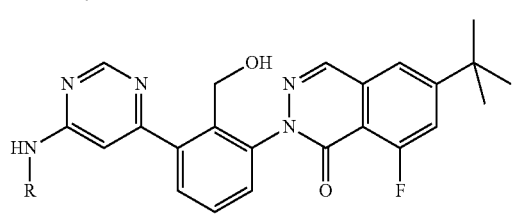
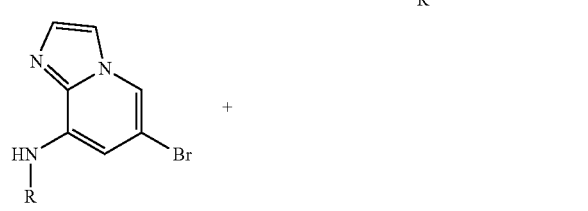
+
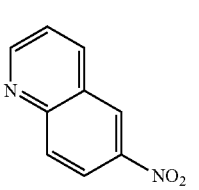
Scheme 8.

-continued

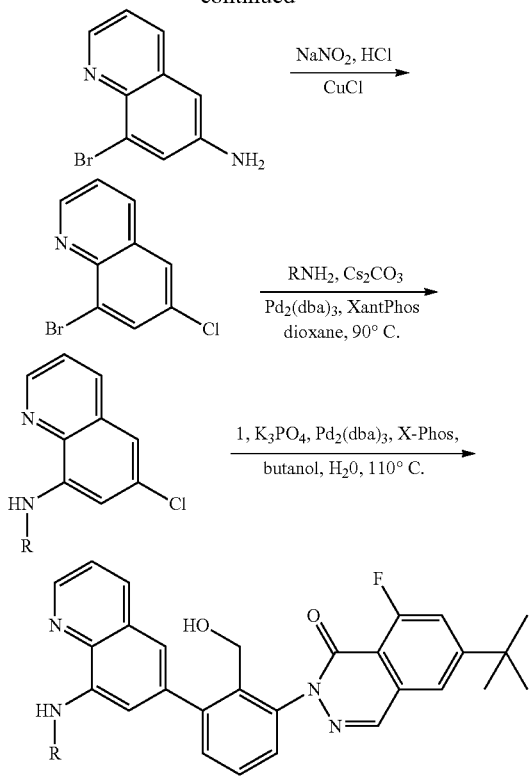

In the above schemes, R can be H, —R$^1$, —R$^1$—R$^2$—R$^3$, —R$^1$—R$^3$, or —R$^2$—R$^3$; R$^1$ can be aryl, heteroaryl, bicyclic heteroaryl, cycloalkyl, heterocycloalkyl, or bicyclic heterocycle, each of which is optionally substituted with one or more lower alkyl, hydroxy, hydroxy lower alkyl, lower alkoxy, halo, nitro, amino, amido, cyano, oxo, or lower haloalkyl; R$^2$ can be —C(=O), —C(=O)O, —C(=O)NR$^{2'}$, —NHC(=O)O, —C(R$^{2'}$)$_2$, —O, —S, —C(=NH)NR$^{2'}$, or —S(=O)$_2$; each R$^{2'}$ can be independently H or lower alkyl; R$^3$ can be H or R$^4$; R$^4$ can be lower alkyl, lower haloalkyl, lower alkoxy, amino, lower alkyl amino, cycloalkyl amino, lower dialkyl amino, aryl, arylalkyl, alkylaryl, heteroaryl, lower alkyl heteroaryl, heteroaryl lower alkyl, cycloalkyl, lower alkyl cycloalkyl, cycloalkyl lower alkyl, heterocycloalkyl, lower alkyl heterocycloalkyl, heterocycloalkyl lower alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring.

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Methods of Treatment

The pyridazinone derivatives described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11):1837-1852)

EXAMPLES

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et$_2$O), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) (Pd(dppf)Cl$_2$), palladium(II) acetate (Pd(OAc)$_2$), tris(dibenzylideneacetone)dipalladium(0) (Pd$_2$(dba)$_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA), and 2-Dicyclohexylphosphino-2',4',6'-triisopropylbiphenyl (XPHOS). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

Synthesis of Compound I-1
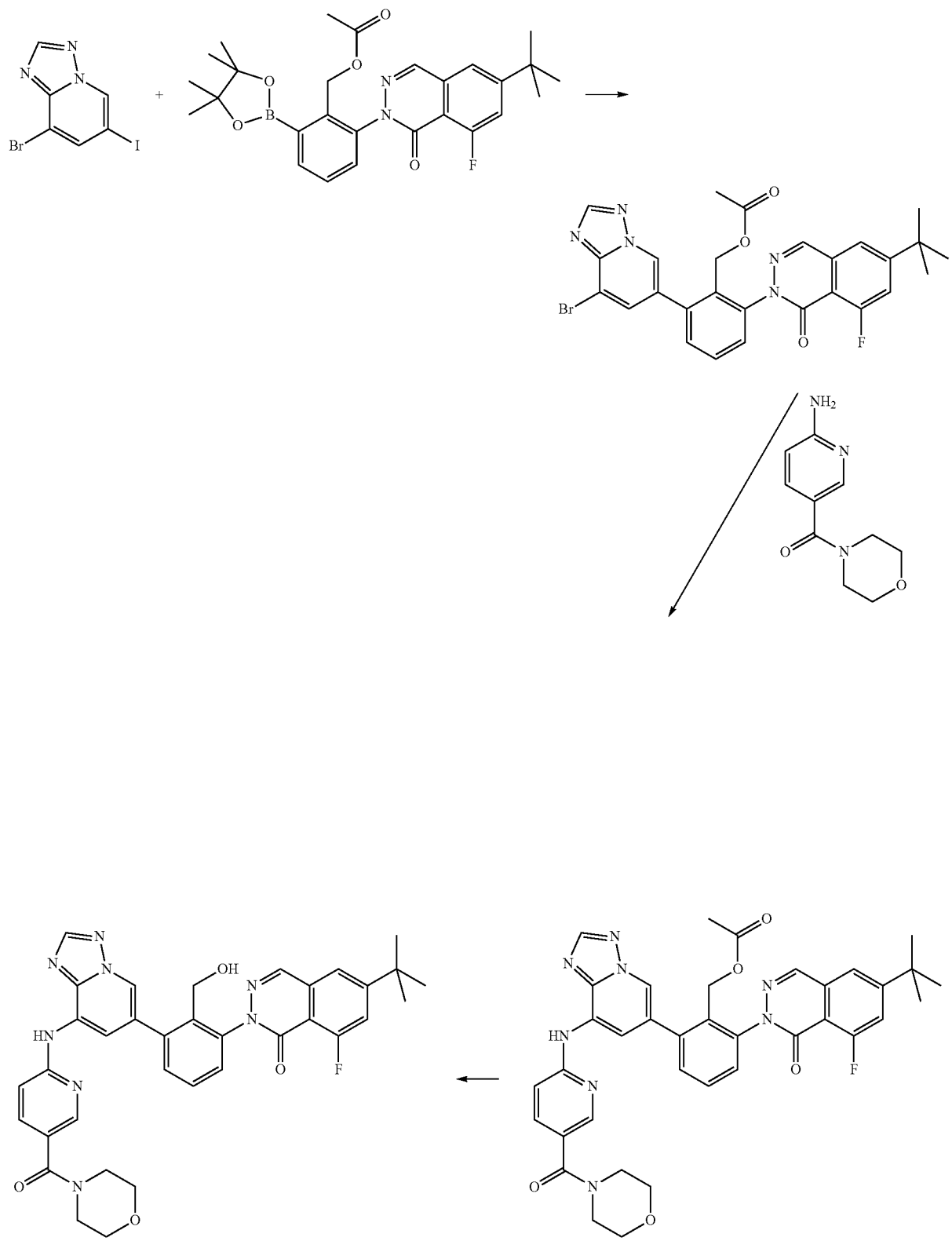
Scheme A

This example illustrates the synthesis of "6-tert-Butyl-8-fluoro-2-(2-hydroxymethyl-3-{8-[5-(morpholine-4-carbonyl)-pyridin-2-ylamino]-[1,2,4]triazolo[1,5-a]pyridin-6-yl}-phenyl)-2H-phthalazin-1-one"

Step 1. Preparation of acetic acid 2-(8-bromo-[1,2,4]triazolo[1,5-a]pyridin-6-yl)-6-(6-tert-butyl-8-fluoro-1-oxo-1H-phthalazin-2-yl)-benzyl ester

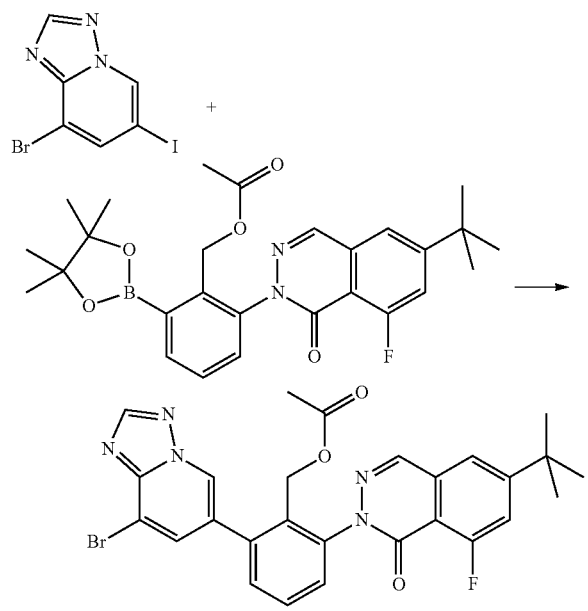

To 8-bromo-6-iodo-[1,2,4]triazolo[1,5-a]pyridine (500 mg, 1.54 mmol, Eq: 1.00) and 2-(6-tert-butyl-8-fluoro-1-oxophthalazin-2(1H)-yl)-6-(4,4,5,5-tetramethyl-1,3,2-dioxaborolan-2-yl)benzyl acetate (763 mg, 1.54 mmol, Eq: 1.00) in dioxanes (50.0 ml) and water (5.00 ml) was added sodium carbonate (654 mg, 6.17 mmol, Eq: 4.00) followed by tetrakis(triphenylphosphine)palladium(0) (178 mg, 154 µmol, Eq: 0.10). The reaction mixture was then heated to 95° C. under argon for 24 h. The reaction was cooled to room temperature. The solvent was evaporated. The residue was dissolved in DCM/water. The layers were separated. The organic layer was dried over MgSO$_4$ and concentrated in vacuo. The crude material was purified by flash chromatography (silica gel, 50 g, 25% to 50% EtOAc/Hex gradient) to give a mixture of acetic acid 2-(8-bromo-[1,2,4]triazolo[1,5-a]pyridin-6-yl)-6-(6-tert-butyl-8-fluoro-1-oxo-1H-phthalazin-2-yl)-benzyl ester and 2-[3-(8-bromo-[1,2,4]triazolo[1,5-a]pyridin-6-yl)-2-hydroxymethyl-phenyl]-6-tert-butyl-8-fluoro-2H-phthalazin-1-one. The mixture was placed under vacuum for 18 h. In a 100 mL round-bottomed flask, 2-(3-(8-bromo-[1,2,4]triazolo[1,5-a]pyridin-6-yl)-2-(hydroxymethyl)phenyl)-6-tert-butyl-8-fluorophthalazin-1(2H)-one (419 mg, 802 µmol, Eq: 1.00), was combined with 2-(8-bromo-[1,2,4]triazolo[1,5-a]pyridin-6-yl)-6-(6-tert-butyl-8-fluoro-1-oxophthalazin-2(1H)-yl)benzyl acetate (155 mg, 275 µmol, Eq: 0.342), acetic anhydride (409 mg, 378 µl, 4.01 mmol, Eq: 5.0) and pyridine (190 mg, 195 µl, 2.41 mmol, Eq: 3.0) in DCM (10.0 ml) to give a colorless solution. The reaction mixture was heated to 45° C. and stirred for 8 h. The reaction was cooled to room temperature and stirred for 12 h. The crude reaction mixture was concentrated in vacuo to obtain a tan oil. The residue was dissolved in DCM and washed once with water. The combined organic layers were dried over MgSO$_4$ and concentrated in vacuo. The crude material was purified by flash chromatography (silica gel, 50 g, 50% EtOAc/Hex) to give acetic acid 2-(8-bromo-[1,2,4]triazolo[1,5-a]pyridin-6-yl)-6-(6-tert-butyl-8-fluoro-1-oxo-1H-phthalazin-2-yl)-benzyl ester (480 mg, 70%). LC/MS-ESI observed [M+H]$^+$ 564, 566.

Step 2. Preparation of Acetic acid 2-(6-tert-butyl-8-fluoro-1-oxo-1H-phthalazin-2-yl)-6-{8-[5-(morpholine-4-carbonyl)-pyridin-2-ylamino]-[1,2,4]triazolo[1,5-a]pyridin-6-yl}-benzyl ester

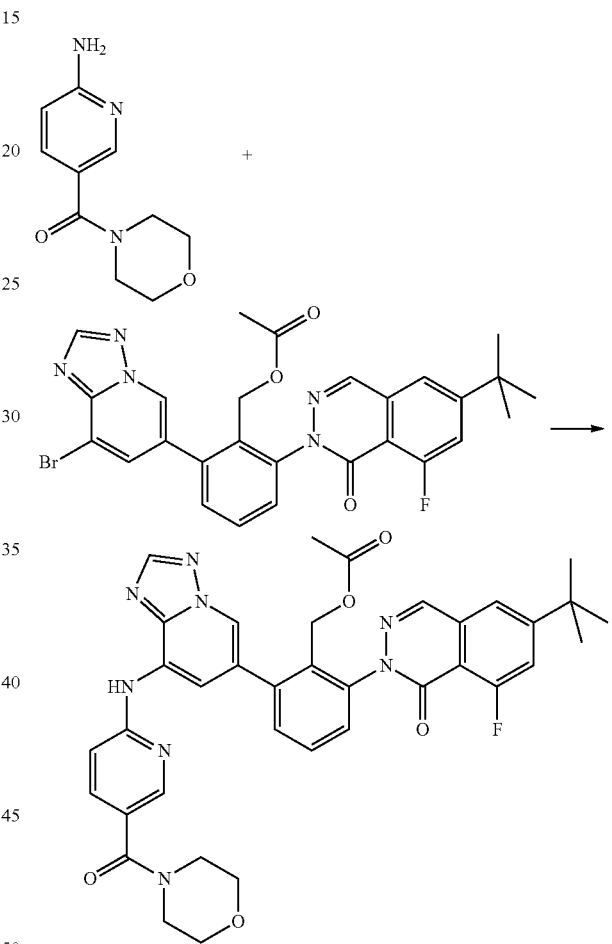

In a 100 ml flask, 2-(8-bromo-[1,2,4]triazolo[1,5-a]pyridin-6-yl)-6-(6-tert-butyl-8-fluoro-1-oxophthalazin-2(1H)-yl)benzyl acetate (250 mg, 443 µmol, Eq: 1.00), (6-aminopyridin-3-yl)(morpholino)methanone (110 mg, 532 µmol, Eq: 1.2) and cesium carbonate (722 mg, 2.21 mmol, Eq: 5.0) were combined with dioxane (31.3 ml) to give an orange suspension. 4,5-Bis(diphenylphosphino)-9,9-dimethylxanthene (38.4 mg, 66.4 µmol, Eq: 0.15) and tris(dibenzylideneacetone)dipalladium(0) (20.3 mg, 22.1 µmol, Eq: 0.05) were added. The solution was degassed with Ar for 10 min. The reaction was heated at 100° C. for 18 h. The reaction mixture was diluted with 200 ml DCM. MgSO$_4$ was added and the mixture was stirred. The solid was removed by filtration and washed several times with DCM. The combined filtrate and washes were concentrated in vacuo. The crude material was purified by flash chromatography (silica gel, 40 g, 5% to 10%

MeOH in DCM gradient). The resulting residue was triturated with Et₂O. The solid was filtered, and then washed with Et₂O. The solid was dried overnight at 50° C. to give acetic acid 2-(6-tert-butyl-8-fluoro-1-oxo-1H-phthalazin-2-yl)-6-{8-[5-(morpholine-4-carbonyl)-pyridin-2-ylamino]-[1,2,4]triazolo[1,5-a]pyridin-6-yl}-benzyl ester (289 mg, 95%). LC/MS-ESI observed [M+H]⁺ 691.

Example 1

Step 3. Preparation of 6-tert-Butyl-8-fluoro-2-(2-hydroxymethyl-3-{8-[5-(morpholine-4-carbonyl)-pyridin-2-ylamino]-[1,2,4]triazolo[1,5-a]pyridin-6-yl}-phenyl)-2H-phthalazin-1-one

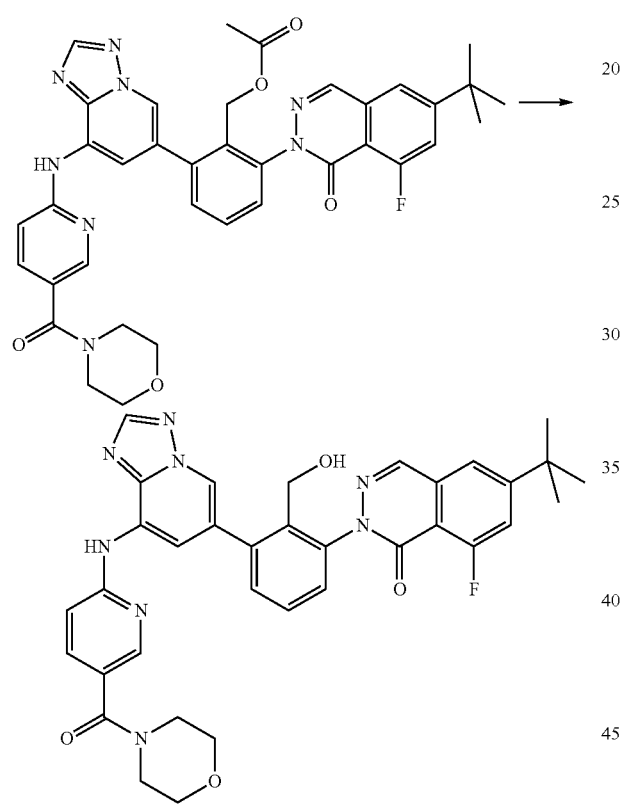

To a solution of 2-(6-tert-butyl-8-fluoro-1-oxophthalazin-2(1H)-yl)-6-(8-(5-(morpholine-4-carbonyl)pyridin-2-ylamino)-[1,2,4]triazolo[1,5-a]pyridin-6-yl)benzyl acetate (289 mg, 418 µmol, Eq: 1.00) in THF (5.0 ml) was added NaOH (1.0 N, 5.0 ml, 5.00 mmol, Eq: 12.0). The solution was heated to 60° C. for 18 h. The reaction was cooled to room temperature. The reaction was diluted with sat NaHCO₃ (aq) and DCM. The layers were separated. The aqueous layer was extracted three times with DCM, and then dried over MgSO₄. The solid was removed by filtration. The filtrate was concentrated in vacuo. The crude material was purified by flash chromatography (silica gel, 0% to 10% MeOH/DCM gradient) to give a residue. The residue was triturated with Et₂O to give 6-tert-butyl-8-fluoro-2-(2-hydroxymethyl-3-{8-[5-(morpholine-4-carbonyl)-pyridin-2-ylamino]-[1,2,4]triazolo[1,5-a]pyridin-6-yl}-phenyl)-2H-phthalazin-1-one (61 mg, 23%). ¹H NMR (300 MHz, CHLOROFORM-d) d ppm 1.36-1.49 (m, 9H) 3.51-3.95 (m, 8H) 4.40 (s, 2H) 7.20 (dd, J=18.13, 7.18 Hz, 1H) 7.41-7.67 (m, 6H) 7.76 (dd, J=8.31, 2.27 Hz, 1H) 8.31 (d, J=2.64 Hz, 1H) 8.36-8.48 (m, 2H) 8.66 (s, 1H) 8.95 (s, 1H) LC/MS-ESI observed [M+H]⁺ 649.

Synthesis of Compound I-2

Scheme B

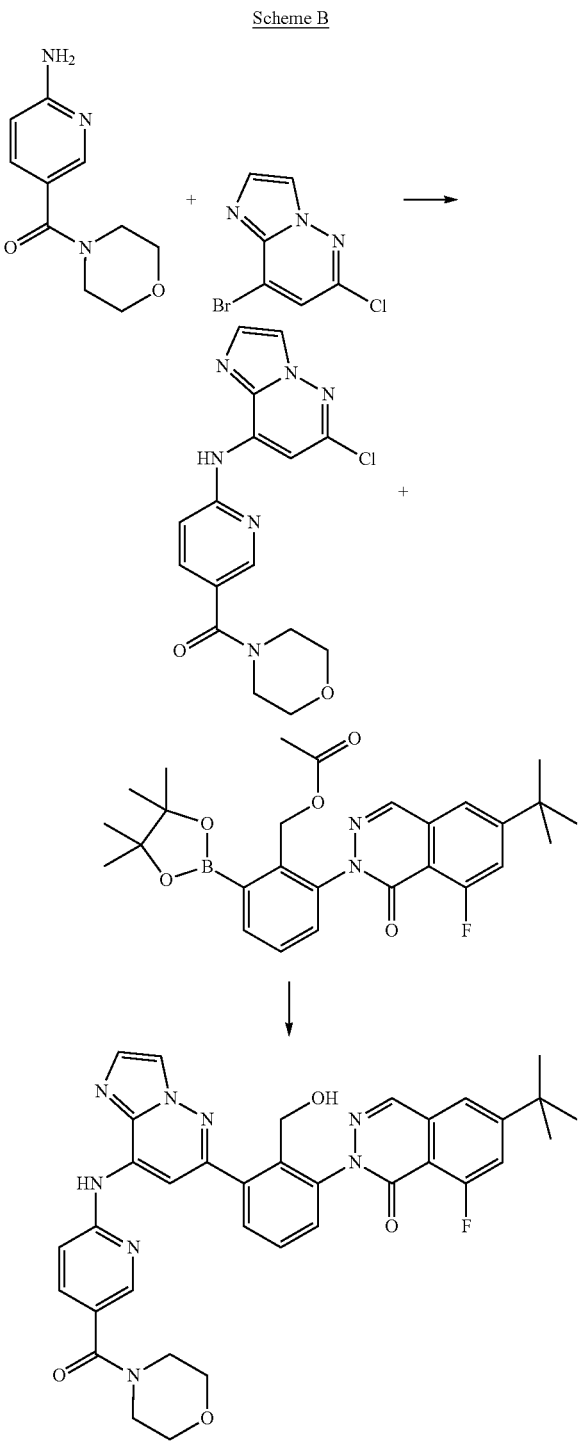

This example illustrates the synthesis of "6-tert-Butyl-8-fluoro-2-(2-hydroxymethyl-3-{8-[5-(morpholine-4-carbonyl)-pyridin-2-ylamino]-imidazo[1,2-b]pyridazin-6-yl}-phenyl)-2H-phthalazin-1-one"

Step 1. Preparation of [6-(6-Chloro-imidazo[1,2-b]pyridazin-8-ylamino)-pyridin-3-yl]-morpholin-4-yl-methanone

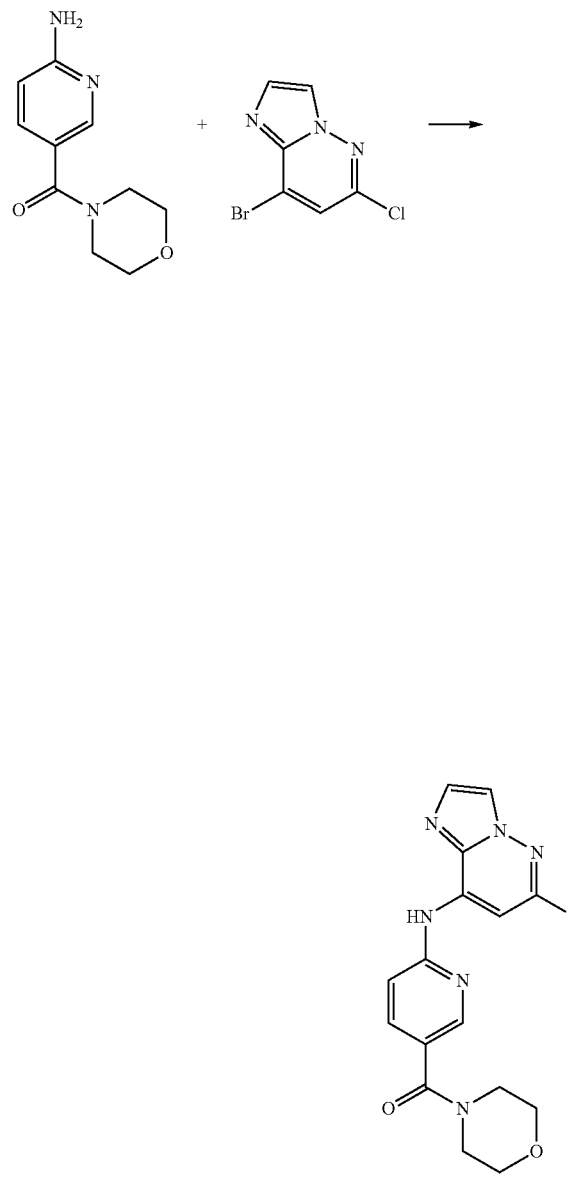

A mixture of 8-bromo-6-chloroimidazo[1,2-b]pyridazine (272 mg, 1.17 mmol, Eq: 1.00) and (6-aminopyridin-3-yl)(morpholino)methanone (255 mg, 1.23 mmol, Eq: 1.05) in DMF (10.0 ml) was cooled to 0° C. To this reaction mixture was added sodium hydride (150 mg, (60% in mineral oil), 3.74 mmol, Eq: 3.2). The reaction was allowed to stir at 0° C. for 10 minutes and then allowed to warm to room temperature and stir 18 h. The reaction mixture was quenched with sat. NaHCO$_3$ (aq) and diluted with water and EtOAc. An insoluble solid was collected by filtration to give [6-(6-chloro-imidazo[1,2-b]pyridazin-8-ylamino)-pyridin-3-yl]-morpholin-4-yl-methanone (420 mg, 99%). LC/MS-ESI observed [M+H]$^+$ 358.

Example 2

Step 2. Preparation of 6-tert-Butyl-8-fluoro-2-(2-hydroxymethyl-3-{8-[5-(morpholine-4-carbonyl)-pyridin-2-ylamino]-imidazo[1,2-b]pyridazin-6-yl}-phenyl)-2H-phthalazin-1-one

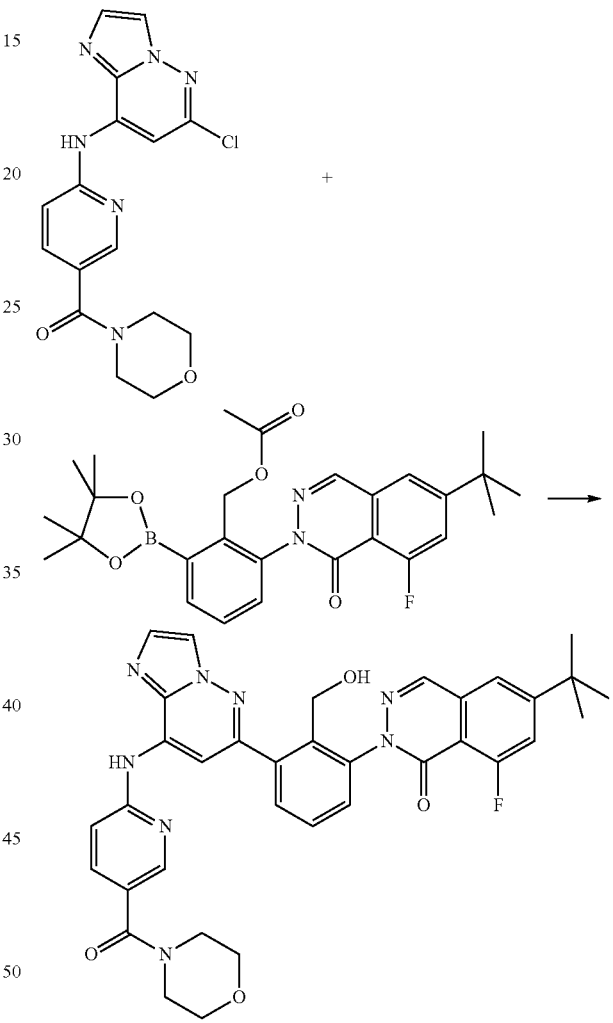

In a 50 mL test tube, (6-(6-chloroimidazo[1,2-b]pyridazin-8-ylamino)pyridin-3-yl)(morpholino)methanone (150 mg, 418 µmol, Eq: 1.00) and 2-(6-tert-butyl-8-fluoro-1-oxophthalazin-2(1H)-yl)-6-(4,4,5,5-tetramethyl-1,3,2-dioxaborolan-2-yl)benzyl acetate (354 mg, 502 µmol, Eq: 1.2) were combined with BuOH (4 ml) to give an orange solution. Water (1.0 ml) was added. The reaction mixture was purged with argon. X-PHOS (19.9 mg, 41.8 µmol, Eq: 0.1) and potassium phosphate tribasic (177 mg, 836 µmol, Eq: 2) were added. Argon was bubbled through the reaction mixture for 2 min. Bis(dibenzylideneacetone)palladium (12.0 mg, 20.9 µmol, Eq: 0.05) was added. The reaction mixture was purged with argon. The reaction heated in an oil bath at 110° C. for 1.5 hours. The reaction mixture was allowed to cool to room temperature. The reaction mixture was poured into 75 mL H₂O and EtOAc was added. A solid formed. DCM was added. The solid remained. The solid collected by filtration and dried to give 6-tert-butyl-8-fluoro-2-(2-hydroxymethyl-3-{8-[5-(morpholine-4-carbonyl)-pyridin-2-ylamino]-imidazo[1,2b]pyridazin-6-yl}-phenyl)-2H-phthalazin-1-one (149 mg, 55%). ¹H NMR (300 MHz, DMSO-d₆) d ppm 1.37 (s, 9H) 3.41-3.70 (m, 9H) 4.42 (br. s., 2H) 7.33-7.63 (m, 5H) 7.64-7.96 (m, 4H) 8.22 (s, 1H) 8.31-8.46 (m, 2H) 8.52 (d, J=2.64 Hz, 1H). LC/MS-ESI observed [M+H]⁺ 649.

Synthesis of compound I-3

Scheme C

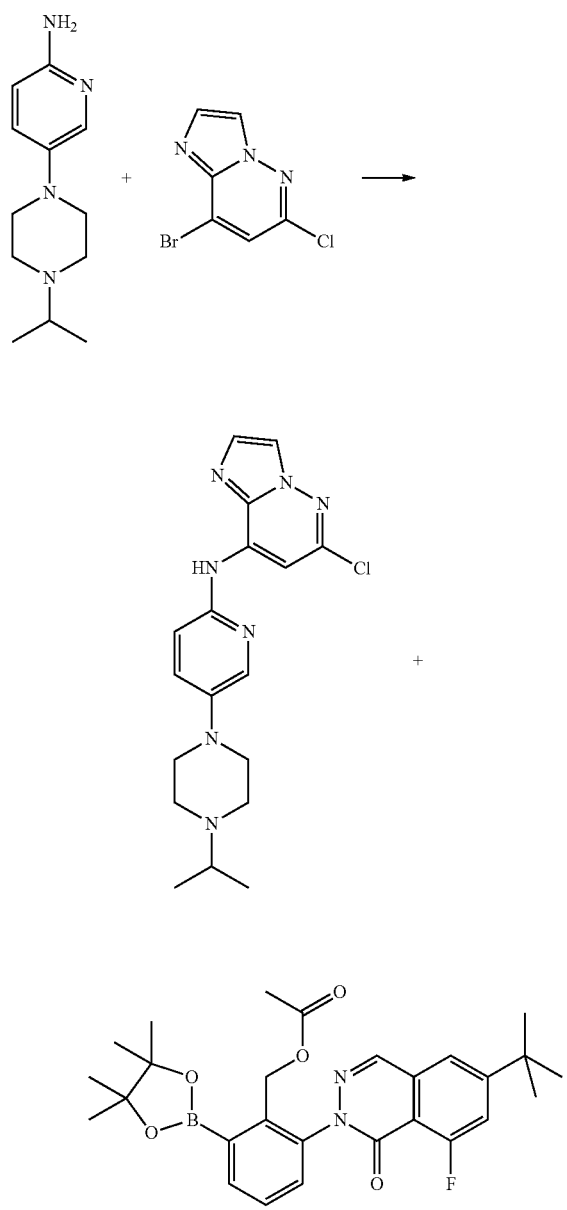

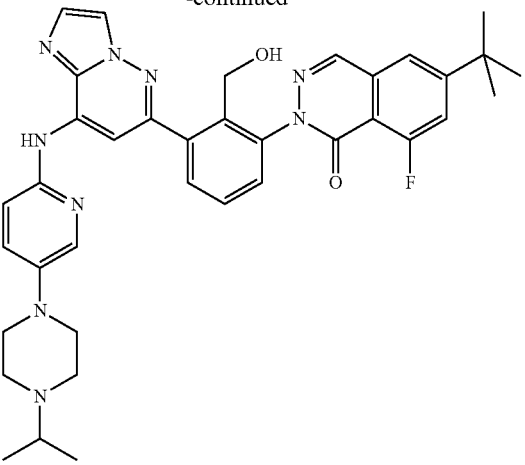

This example illustrates the synthesis of "6-tert-Butyl-8-fluoro-2-(2-hydroxymethyl-3-{8-[5-(4-isopropyl-piperazin-1-yl)-pyridin-2-ylamino]-imidazo[1,2-b]pyridazin-6-yl}-phenyl)-2H-phthalazin-1-one"

Step 1. Preparation of (6-Chloro-imidazo[1,2-b]pyridazin-8-yl)-[5-(4-isopropyl-piperazin-1-yl)-pyridin-2-yl]-amine

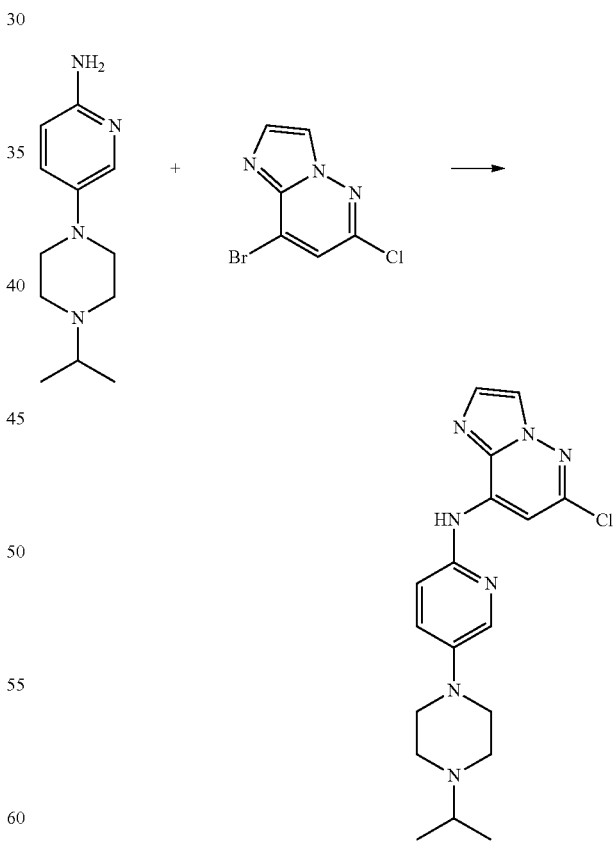

A mixture of 8-bromo-6-chloroimidazo[1,2-b]pyridazine (200 mg, 862 μmol, Eq: 0.95) and 5-(4-isopropylpiperazin-1-yl)pyridin-2-amine (200 mg, 908 μmol, Eq: 1.00) in DMF (10.0 ml) was cooled to 0° C. To this reaction mixture was added sodium hydride (116 mg, (60% in mineral oil), 2.9 mmol, Eq: 3.2). The reaction was allowed to stir at 0° C. for 10 min then allowed to warm to room temperature and stir 18 h. The reaction mixture was quenched with sat. NaHCO₃ (aq) and diluted with water and EtOAc. The organic layer was separated and the aqueous phase was extracted with EtOAc. The organic layers were combined, dried over MgSO₄ and concentrated in vacuo. The crude material was purified by flash chromatography (silica gel, 0% to 20% (60:10:1 DCM:MeOH:NH₄OH)/DCM gradient) to give a residue that was placed under high vacuum for 18 h to afford (6-chloro-imidazo[1,2-b]pyridazin-8-yl)-[5-(4-isopropyl-piperazin-1-yl)-pyridin-2-yl]-amine (78 mg, 23%). LC/MS-ESI observed [M+H]⁺ 372.

Example 3

Step 2. Preparation of 6-tert-Butyl-8-fluoro-2-(2-hydroxymethyl-3-{8-[5-(4-isopropyl-piperazin-1-yl)-pyridin-2-ylamino]-imidazo[1,2-b]pyridazin-6-yl}-phenyl)-2H-phthalazin-1-one

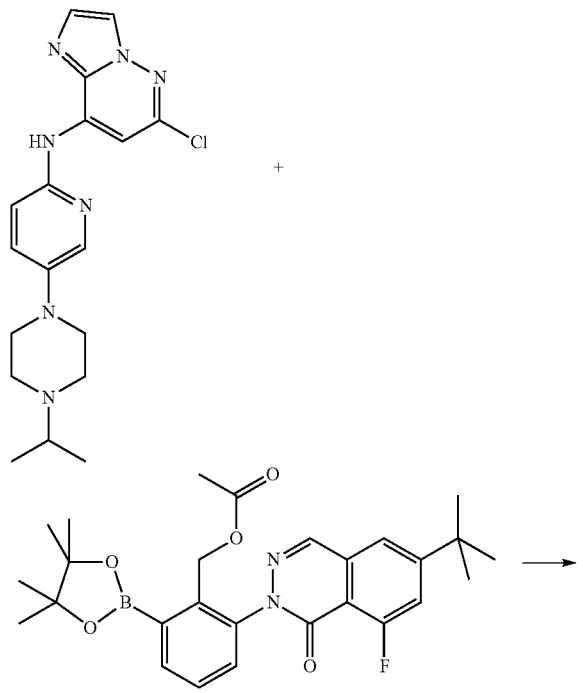

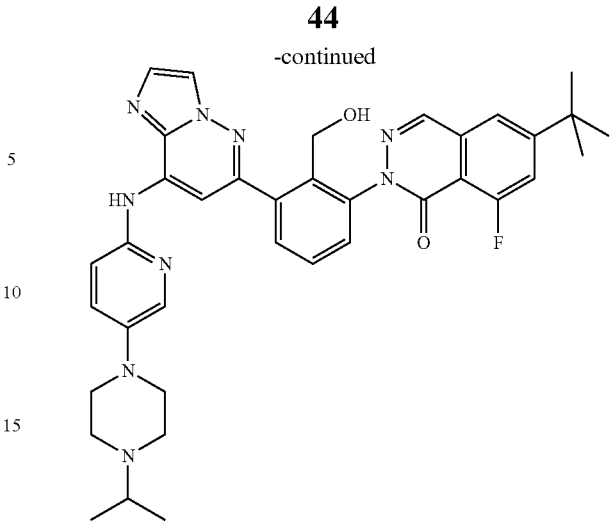

In a 50 mL test tube, 6-chloro-N-(5-(4-isopropylpiperazin-1-yl)pyridin-2-yl)imidazo[1,2-b]pyridazin-8-amine (77.5 mg, 208 µmol, Eq: 1.00) and 2-(6-tert-butyl-8-fluoro-1-oxophthalazin-2(1H)-yl)-6-(4,4,5,5-tetramethyl-1,3,2-dioxaborolan-2-yl)benzyl acetate (177 mg, 250 µmol, Eq: 1.2) were combined with BuOH (4 ml) to give an orange solution. Water (1.0 ml) was added. X-PHOS (9.94 mg, 20.8 µmol, Eq: 0.1) and potassium phosphate tribasic (88.5 mg, 417 µmol, Eq: 2) were added. Bis(dibenzylideneacetone)palladium (5.99 mg, 10.4 µmol, Eq: 0.05) was added.

The reaction mixture was purged with argon. The reaction was heated at 110° C. for 1.5 hours. The reaction mixture was allowed to cool to room temperature. The reaction mixture was poured into 75 mL H₂O and extracted with EtOAc. The layers were separated. The aqueous layer was extracted twice with EtOAc. The organic layers were combined, washed with brine, dried over MgSO₄ and concentrated in vacuo. The crude material was purified by flash chromatography (silica gel, 24 g, 50% to 75% (60:10:1 DCM:MeOH:NH4OH)/DCM gradient) to give a residue. The residue was triturated with Et₂O and allowed to sit for 24 h to give 6-tert-butyl-8-fluoro-2-(2-hydroxymethyl-3-{8-[5-(4-isopropyl-piperazin-1-yl)-pyridin-2-ylamino]-imidazo[1,2-b]pyridazin-6-yl}-phenyl)-2H-phthalazin-1-one (75 mg, 55%) as a white solid. ¹H NMR (300 MHz, CHLOROFORM-d) d ppm 1.17 (d, J=14.35 Hz, 6H) 1.43 (s, 9H) 2.74 (br. s., 5H) 3.24 (br. s., 4H) 3.95-4.17 (m, 1H) 4.45 (d, J=7.18 Hz, 2H) 7.01 (d, J=9.06 Hz, 1H) 7.28-7.35 (m, 1H) 7.40-7.66 (m, 5H) 7.74 (d, J=6.80 Hz, 1H) 7.87 (d, J=1.13 Hz, 1H) 8.01-8.15 (m, 2H) 8.23 (s, 1H) 8.30 (d, J=2.64 Hz, 1H). LC/MS-ESI observed [M+H]⁺ 662.

Synthesis of Compound I-4

Scheme D
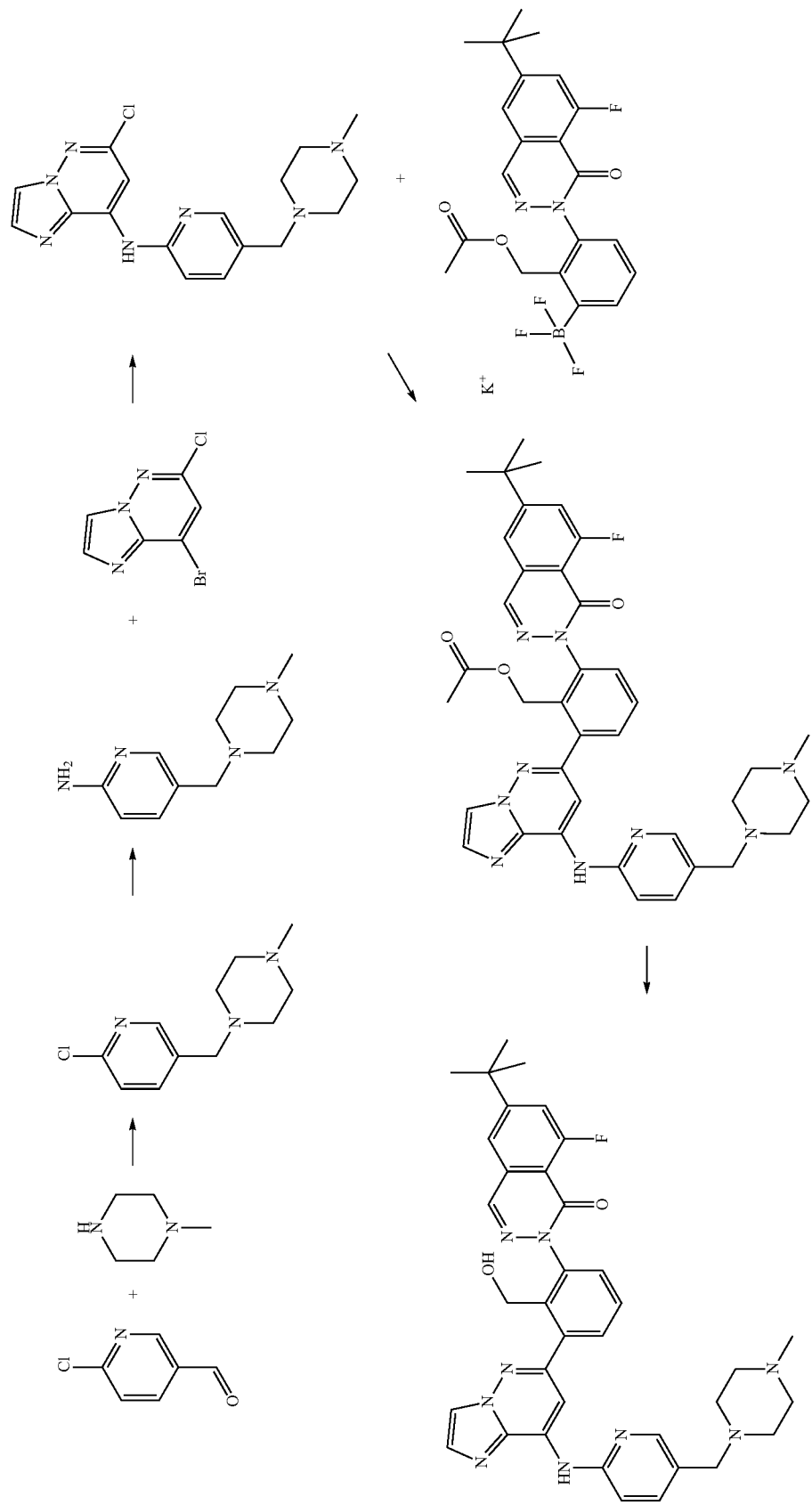

This example illustrates the synthesis of "6-tert-Butyl-8-fluoro-2-(2-hydroxymethyl-3-{8-[5-(4-methyl-piperazin-1-ylmethyl)-pyridin-2-ylamino]-imidazo[1,2-b]pyridazin-6-yl}-phenyl)-2H-phthalazin-1-one"

Step 1. Preparation of 1-(6-Chloro-pyridin-3-ylmethyl)-4-methyl-piperazine

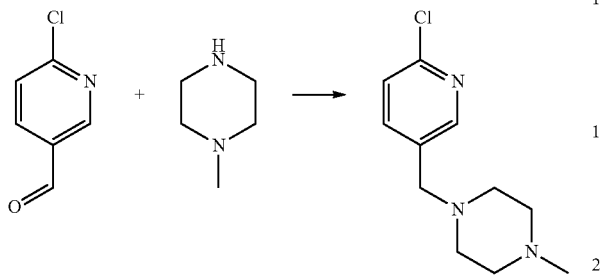

In a 500 ml round bottom flask 6-chloronicotinaldehyde (5 g, 35.3 mmol, Eq: 1.00) was suspended in DCM (350 ml). 1-Methylpiperazine (4.42 g, 4.9 ml, 44.2 mmol, Eq: 1.25) was added, followed by acetic acid (4.24 g, 4.04 ml, 70.6 mmol, eq: 2.0). Sodium triacetoxyborohydride (11.2 g, 53.0 mmol, Eq: 1.5) was added by portions over several minutes. The reaction stirred at room temperature for three hours. Water and DCM were added and the layers were separated. The aqueous layer was brought to pH 10 with 1M NaOH. The aqueous layer was extracted three times with DCM. The combined extract was dried over $Na_2SO_4$ and concentrated in vacuo to give 1-(6-chloro-pyridin-3-ylmethyl)-4-methyl-piperazine (6.8 g, 85%) LC/MS-ESI observed $[M+H]^+$ 226. The crude material was used "as is" in the next reaction.

Step 2. Preparation of 5-(4-Methyl-piperazin-1-ylmethyl)-pyridin-2-ylamine

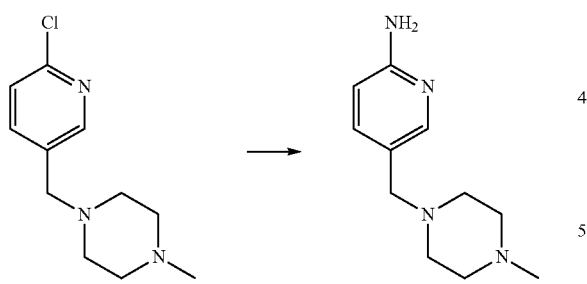

To 1-((6-chloropyridin-3-yl)methyl)-4-methylpiperazine (6.79 g, 30.1 mmol, Eq: 1.00), 2-(dicyclohexylphosphino) biphenyl (2.11 g, 6.02 mmol, Eq: 0.20) and tris(dibenzylideneacetone)dipalladium (0) (2.75 g, 3.01 mmol, Eq: 0.10) in a sealed tube was added THF (75 ml). The solution was placed under nitrogen. Lithium bis(trimethylsilyl)amide (75.2 ml, 75.2 mmol, Eq: 2.50) was added. The solution was degassed with argon and the tube was sealed and heated at 100° C. for 18 h. The solution was filtered through Celite™. The solvent was evaporated under reduced pressure. The residue was taken up in DCM. HCl (1N, 10 ml) was added slowly to adjust to pH=1 by adding 6 N HCl and water (as needed). The layers were separated. The organic layer was extracted once with water. The aqueous layers were combined and were brought to pH 10 by a slow addition of solid NaOH. Dichloromethane was added. The layers were separated. The aqueous layer was extracted three times with DCM. The organic layers were combined and dried over $Na_2SO4$. The solvent was evaporated. The residue was triturated with $Et_2O$. The solid was collected by filtration and dried to give 5-(4-methyl-piperazin-1-ylmethyl)-pyridin-2-ylamine (2.3 g, 37%). LC/MS-ESI observed $[M+H]^+$ 207.

Step 3a. Preparation of (6-Chloro-imidazo[1,2-b]pyridazin-8-yl)-[5-(4-methyl-piperazin-1-ylmethyl)-pyridin-2-yl]-amine

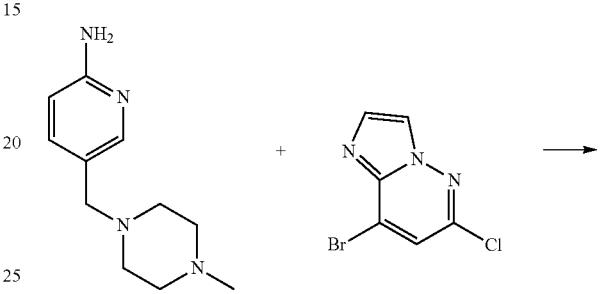

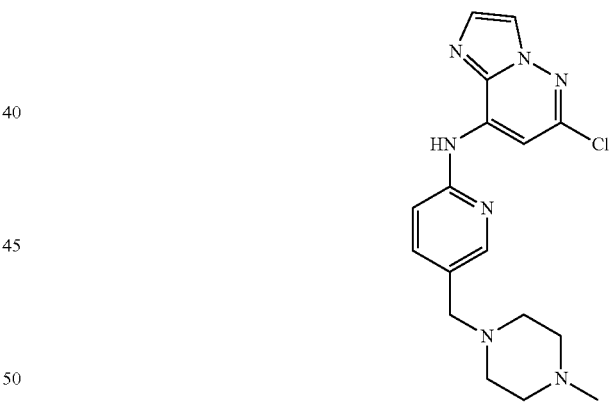

A mixture of 8-bromo-6-chloroimidazo[1,2-b]pyridazine (214 mg, 921 μmol, Eq: 0.95) and 5-((4-methylpiperazin-1-yl)methyl)pyridin-2-amine (200 mg, 970 μmol, Eq: 1.00) in DMF (10.0 ml) was cooled to 0° C. To this was added sodium hydride (60% in mineral oil, 124 mg, 3.1 mmol, Eq: 3.2). The reaction was allowed to stir at 0° C. for 10 min and then allowed to warm to room temperature and stirred for 72 h. The reaction was quenched with saturated $NaHCO_3$ (aq) and then diluted with water and EtOAc. The organic layer was separated and the aqueous phase was washed with EtOAc. The organic layers were combined, dried over $MgSO_4$ and concentrated in vacuo. The residue was dissolved in $Et_2O$. The organic layer was washed with water and dried over $MgSO_4$. The drying agent was removed by filtration. The resulting solution was concentrated in vacuo to give (6-chloro-imidazo

[1,2-b]pyridazin-8-yl)-[5-(4-methyl-piperazin-1-ylmethyl)-pyridin-2-yl]-amine (170 mg, 49%) as a solid. LC/MS-ESI observed [M+H]+ 358.

Step 3b. Preparation of potassium (2-(acetoxymethyl)-3-(6-tert-butyl-8-fluoro-1-oxophthalazin-2(1H)-yl)phenyl)trifluoroborate

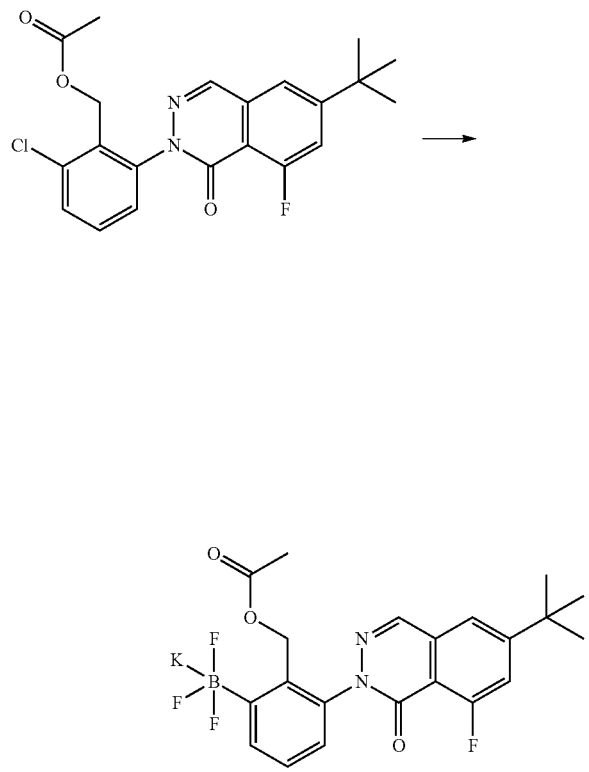

A round-bottomed flask equipped with a bubbler, a thermometer, and a magnetic stirrer was charged with 2-(6-tert-butyl-8-fluoro-1-oxophthalazin-2(1H)-yl)-6-chlorobenzyl acetate (10 g, 24.8 mmol, Eq: 1.00), 4,4,4',4',5,5,5',5'-octamethyl-2,2'-bi(1,3,2-dioxaborolane) (9.46 g, 37.2 mmol, Eq: 1.5), Pd(OAc)₂ (69.7 mg, 310 μmol, Eq: 0.0125), X-PHOS (296 mg, 621 μmol, Eq: 0.025), and potassium acetate (5.29 g, 53.9 mmol, Eq: 2.17). The reaction mixture was degassed (3 times). Added MeTHF, then again degassed (3 times). Mixture was heated at 60° C. over night. Reaction was not finished. Reaction temperature was increased to 65° C. and stirred for 3 hours. HPLC showed that the reaction was completed. The reaction was cooled and 2 N HCl (31.0 ml, 62.1 mmol, Eq: 2.5) was added. The mixture was stirred for half an hour, then was passed through a celite plug to remove a black material. The layers were separated. The organic layer was washed with water (60.0 g, 60.0 ml) and then concentrated to a heavy oil. The oil was dissolved in MeOH (79.2 g, 100 ml) and treated with potassium hydrogen fluoride, 3M solution (20.7 ml, 62.1 mmol, Eq: 2.5). LC showed reaction was not finished overnight. Another 0.5 equivalent of KHF2 was added. The resultant slurry was warmed at 45° C. for 3 hours. The mixture was stirred over night at room temperature. Product was isolated by filtration. Cake was washed with methanol.

After drying by vacuum, potassium (2-(acetoxymethyl)-3-(6-tert-butyl-8-fluoro-1-oxophthalazin-2(1H)-yl)phenyl)trifluoroborate (11.26 g, 23.7 mmol, 95.6% yield) was obtained.

Step 4. Preparation of acetic acid 2-(6-tert-butyl-8-fluoro-1-oxo-1H-phthalazin-2-yl)-6-{8-[5-(4-methyl-piperazin-1-ylmethyl)-pyridin-2-ylamino]-imidazo[1,2-b]pyridazin-6-yl}-benzyl ester

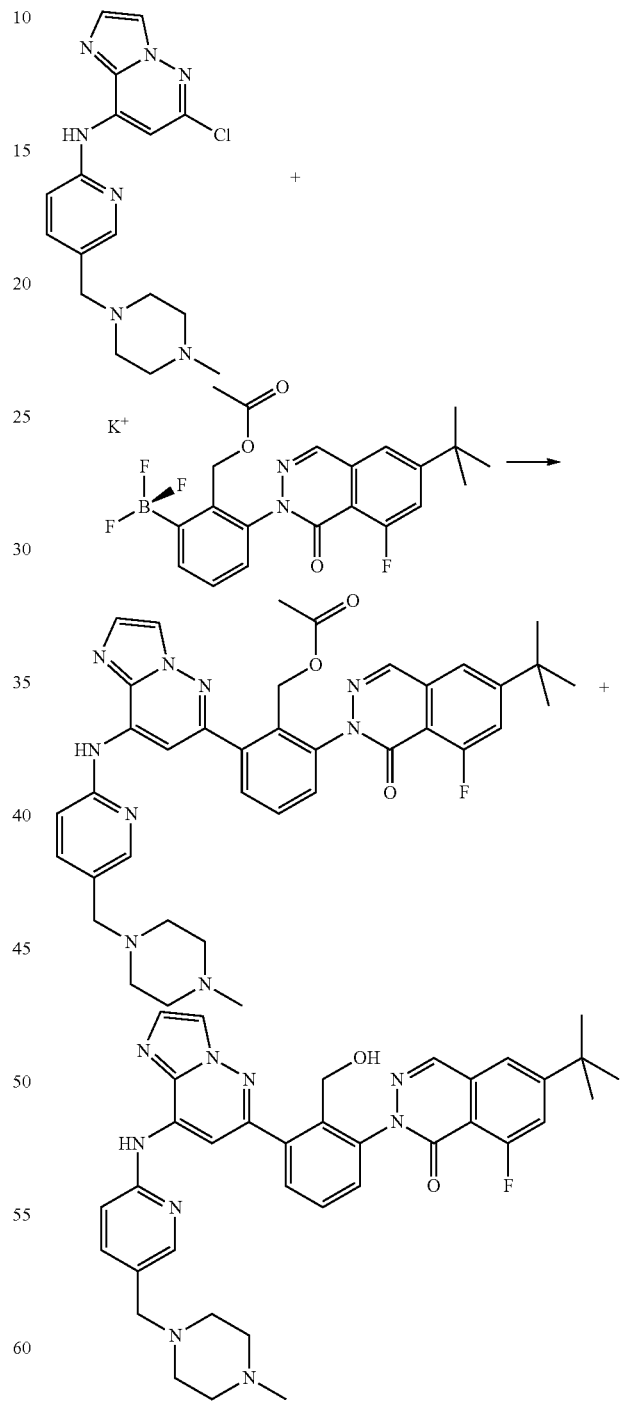

In a 50 mL test tube, 6-chloro-N-(5((4-methylpiperazin-1-yl)methyl)pyridin-2-yl)imidazo[1,2-b]pyridazin-8-amine (170 mg, 475 μmol, Eq: 1.00) and potassium (2-(acetoxymethyl)-3-(6-tert-butyl-8-fluoro-1-oxophthalazin-2(1H)-yl)phenyl)trifluoroborate (225 mg, 475 μmol, Eq: 1.00) were combined with BuOH (10 ml) to give an orange solution. Water (2.5 ml) was added. X-PHOS (22.6 mg, 47.5 μmol, Eq: 0.1) and potassium phosphate tribasic (202 mg, 950 μmol, eq: 2) were added. Bis(dibenzylideneacetone)palladium (13.7 mg, 23.8 μmol, Eq: 0.05) was added. The tube was purged with argon and sealed. The solution was warmed in an oil bath at 100° C. for 1.5 hours. The solution was cooled to room temperature. The reaction mixture was poured into 75 mL H₂O and extracted with EtOAc. The organic layer was dried over Na₂SO₄ and concentrated in vacuo. The crude material was purified by flash chromatography (silica gel, 24 g, 50% to 100% (60:10:1 DCM:MeOH:NH₄OH)/DCM gradient) to give a residue. The residue was triturated with Et₂O. LC/MS analysis showed that the crude material was a mix of products: 12% 6-tert-butyl-8-fluoro-2-(2-hydroxymethyl-3-{8-[5-(4-methyl-piperazin-1-ylmethyl)-pyridin-2-ylamino]-imidazo[1,2-b]pyridazin-6-yl}-phenyl)-2H-phthalazin-1-one and 88% acetic acid 2-(6-tert-butyl-8-fluoro-1-oxo-1H-phthalazin-2-yl)-6-{8-[5-(4-methyl-piperazin-1-ylmethyl)-pyridin-2-ylamino]-imidazo[1,2-b]pyridazin-6-yl}-benzyl ester by UV. (157 mg, 48%). The mixture was taken into the next reaction "as is." LC/MS-ESI observed [M+H]⁺ 648 and 690.

Example 4

Step 5. Preparation of 6-tert-Butyl-8-fluoro-2-(2-hydroxymethyl-3-{8-[5-(4-methyl-piperazin-1-ylmethyl)-pyridin-2-ylamino]-imidazo[1,2-b]pyridazin-6-yl}-phenyl)-2H-phthalazin-1-one

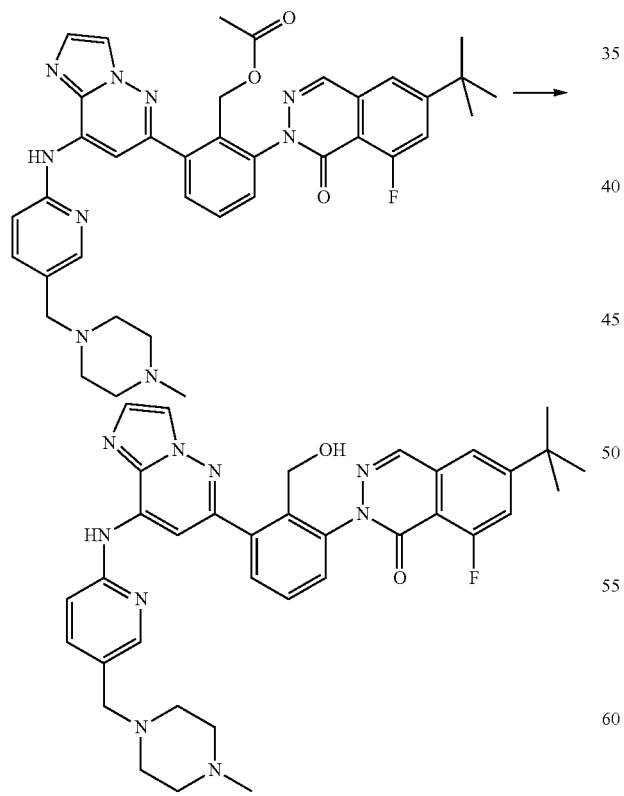

To a solution of a mixture of 2-(6-tert-butyl-8-fluoro-1-oxophthalazin-2(1H)-yl)-6-(8-(5-((4-methylpiperazin-1-yl)methyl)pyridin-2-ylamino)imidazo[1,2-b]pyridazin-6-yl) benzyl acetate and 6-tert-butyl-8-fluoro-2-(2-hydroxymethyl-3-{8-[5-(4-methyl-piperazin-1-ylmethyl)-pyridin-2-ylamino]-imidazo[1,2-b]pyridazin-6-yl}-phenyl)-2H-phthalazin-1-one (157 mg, 228 μmol, Eq: 1.00) in THF (3.0 ml) was added NaOH (1.0 N, 3.0 ml, 3.00 mmol, Eq: 13.2). The solution was heated to 60° C. for 18 h. The reaction was cooled to room temperature. The reaction mixture was diluted with sat. NaHCO₃ (aq) and DCM. The layers were separated. The aqueous layer was extracted three times with DCM. The combined organic extracts were dried over Na₂SO₄ and concentrated in vacuo. The resulting solid was triturated with Et₂O and collected by filtration to give 6-tert-butyl-8-fluoro-2-(2-hydroxymethyl-3-{8-[5-(4-methyl-piperazin-1-ylmethyl)-pyridin-2-ylamino]-imidazo[1,2-b]pyridazin-6-yl}-phenyl)-2H-phthalazin-1-one (101 mg, 68%). ¹H NMR (300 MHz, CHLOROFORM-d) δ ppm 1.43 (s, 9H) 2.36 (br. s., 2H) 2.56 (br. s., 8H) 3.51 (s, 3H) 4.02 (br. s., 1H) 4.46 (br. s., 2H) 7.02 (d, J=8.31 Hz, 1H) 7.40-7.70 (m, 6H) 7.75 (d, J=7.18 Hz, 1H) 7.90 (s, 1H) 8.23 (s, 1H) 8.30 (d, J=2.27 Hz, 2H) 8.44 (s, 1H). LC/MS-ESI observed [M+H]⁺ 648.

Synthesis of compound I-5

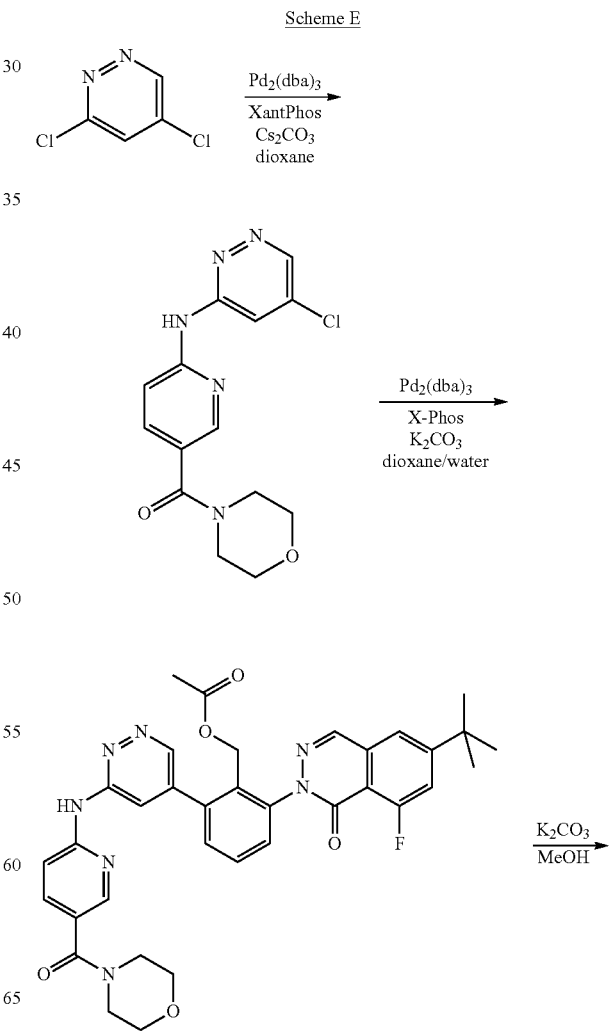

Scheme E

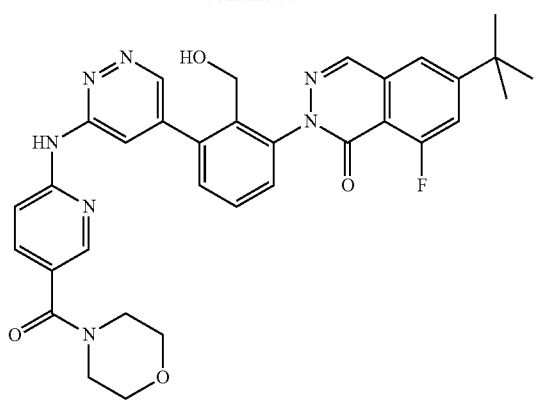

This example illustrates the synthesis of "6-tert-Butyl-8-fluoro-2-(2-hydroxymethyl-3-{6-[5-(morpholine-4-carbonyl)-pyridin-2-ylamino]pyridazin-4-yl}-phenyl)-2H-phthalazin-1-one"

Step 1. Preparation of [6-(5-chloro-pyridazin-3-ylamino)-pyridin-3-yl]-morpholin-4-yl-methanone

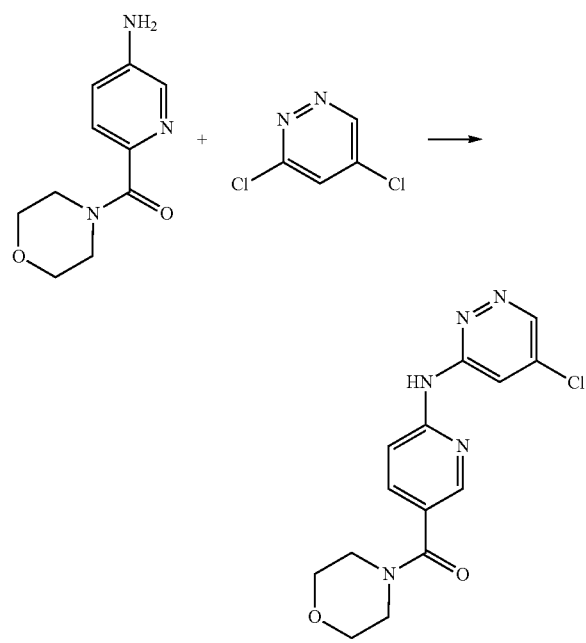

3,5-Dichloropyridazine (1.0 g, 4.83 mmol), (4-aminophenyl)(morpholino)methanone (864 mg, 5.80 mmol), Cs$_2$CO$_3$ (3.15 g, 9.66 mmol) were dissolved in dioxane (20 ml). Under N$_2$ atmosphere, Pd$_2$(dba)$_3$ (221 mg, 0.24 mmol) and Xantphos (280 mg, 0.48 mmol) were added and the mixture was stirred at reflux temperature overnight. After the completion of the reaction, the mixture was cooled to room temperature, poured into water (100 ml), and extracted by DCM (100 ml). The combined organic phases were washed with saturated aqueous solution of sodium chloride (100 ml), dried over sodium sulfate and concentrated. The residue was purified by silica gel column (petroleum ether:ethyl acetate=1:5). The desired product was obtained as a yellow solid (715 mg, yield 46%). LC-MS: 320[M+1]$^+$, t$_R$=1.208 min.

Step 2. Preparation of acetic acid 2-(6-tert-butyl-8-fluoro-1-oxo-1H-phthalazin-2-yl)-6-{6-[5-(morpholine-4-carbonyl)-pyridin-2-ylamino]-pyridazin-4-yl}-benzyl ester

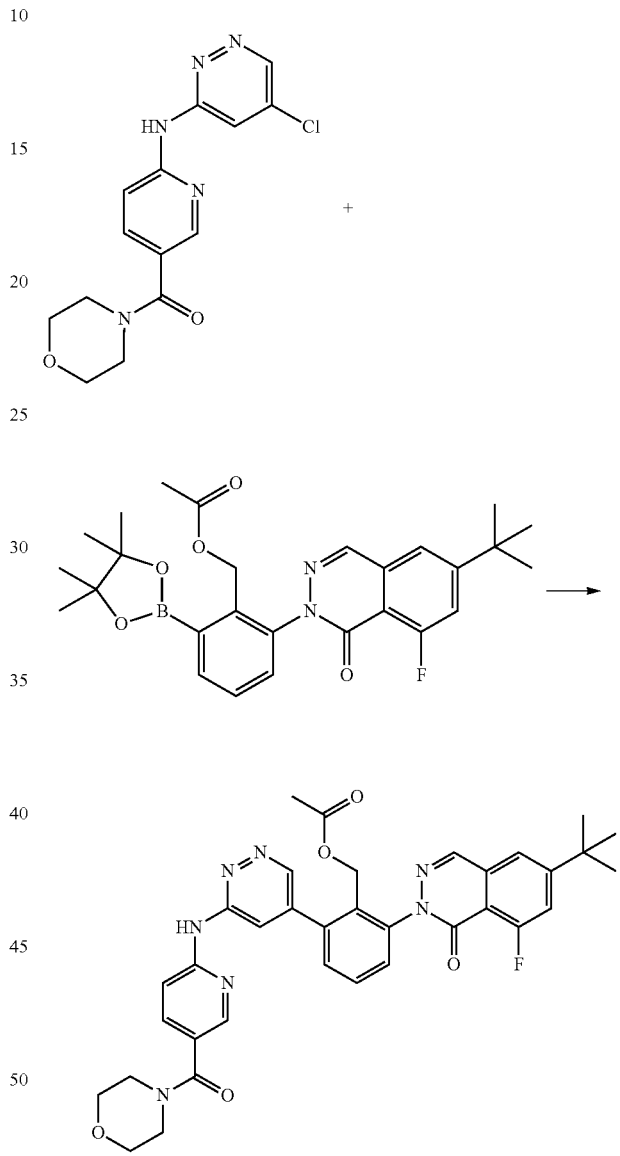

[6-(5-Chloro-pyridazin-3-ylamino)-pyridin-3-yl]-morpholin-4-yl-methanone (200 mg, 0.63 mmol), acetic acid 2-(6-tert-butyl-8-fluoro-1-oxo-1H-phthalazin-2-yl)-6-(4,4,5,5-tetramethyl[1,3,2]dioxaborolan-2-yl)-benzyl ester (470 mg, 1.25 mmol) and K$_2$CO$_3$ (173 mg, 1.25 mmol) were dissolved in dioxane/H$_2$O (10:1, 11 ml). Under N$_2$ atmosphere, Pd$_2$(dba)$_3$ (58 mg, 0.063 mmol) and X-phos (120 mg, 0.25 mmol) were added and the mixture was stirred at reflux temperature overnight. After the completion of the reaction, the mixture was cooled to room temperature and filtered. The organic layer was washed with saturated brine, dried over sodium sulfate and concentrated. The residue was purified by silica gel column (petroleum ether:ethyl acetate=2:1). The desired product was obtained as a yellow solid (240 mg, yield 59%). LC-MS: 652[M+1]⁺, $t_R$=1.459 min.

Example 5

Step 3. 6-tert-Butyl-8-fluoro-2-(2-hydroxymethyl-3-{6-[5-(morpholine-4-carbonyl)-pyridin-2-ylamino]-pyridazin-4-yl}-phenyl)-2H-phthalazin-1-one

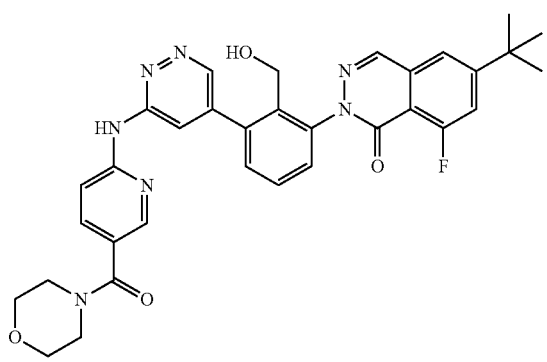 [SMILES: CC(C)(C)c1cc(F)c2c(=O)n(-c3cccc(-c4cnnc(Nc5ccc(C(=O)N6CCOCC6)cn5)c4)c3CO)ncc2c1]

Acetic acid 2-(6-tert-butyl-8-fluoro-1-oxo-1H-phthalazin-2-yl)-6-{6-[5-(morpholine-4-carbonyl)-pyridin-2-ylamino]-pyridazin-4-yl}-benzyl ester (240 mg, 0.37 mmol) was dissolved in methanol (10 ml). K₂CO₃ (102 mg, 0.74 mmol) was added at room temperature and the mixture was stirred at that temperature for 2 hours. After the completion of the reaction, the mixture was filtered. The filtrate was washed with water, dried over sodium sulfate and concentrated. The desired product was obtained as a yellow solid (150 mg, yield 67%). ¹H NMR (300 MHz, DMSO): δ 10.56 (s, 1H), 8.96 (d, J=1.9 Hz, 1H), 8.55-8.51 (m, 1H), 8.34 (d, J=2.2 Hz, 1H), 8.23 (d, J=1.9 Hz, 1H), 7.88 (d, J=1.6 Hz, 1H), 7.85-7.73 (m, 3H), 7.65-7.47 (m, 3H), 4.88-4.80 (m, 1H), 4.28 (ddd, J=4.3, 3.1, 2.0 Hz, 2H), 3.65-3.46 (m, 8H), 1.38 (s, 9H). LC-MS: 610[M+1]⁺, $t_R$=1.389 min. HPLC: 97.93% at 214 nm, 98.77% at 254 nm, $t_R$=3.532 min.

Synthesis of Compound I-6

Scheme F

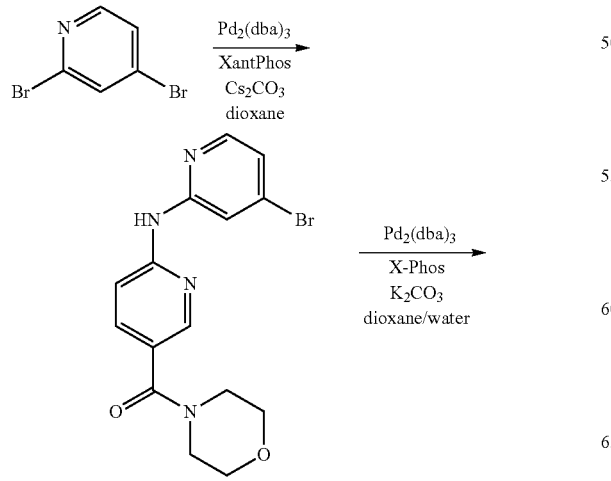

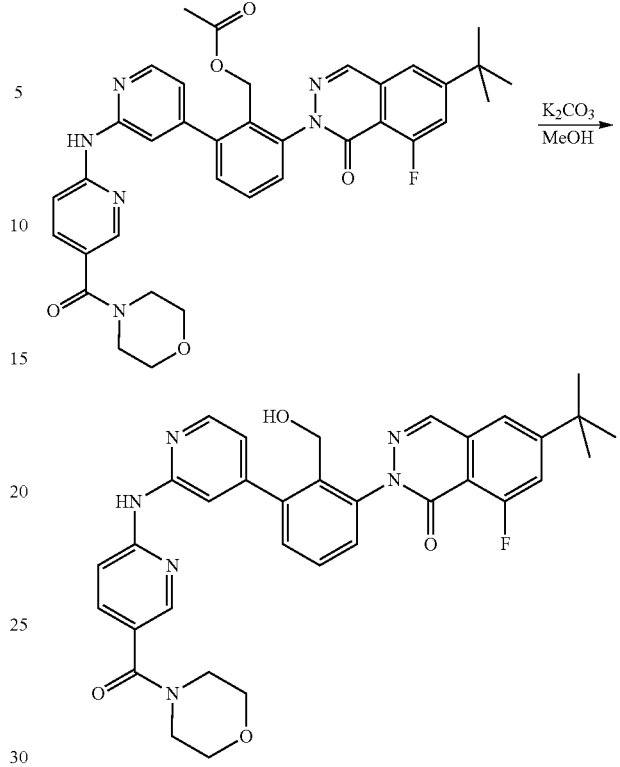

This example illustrates the synthesis of "6-tert-Butyl-8-fluoro-2-(2-hydroxymethyl-3-{2-[5-(morpholine-4-carbonyl)-pyridin-2-ylamino]pyridin-4-yl}-phenyl)-2H-phthalazin-1-one"

Step 1. Preparation of [6-(4-Bromo-pyridin-2-ylamino)-pyridin-3-yl]-morpholin-4-yl-methanone

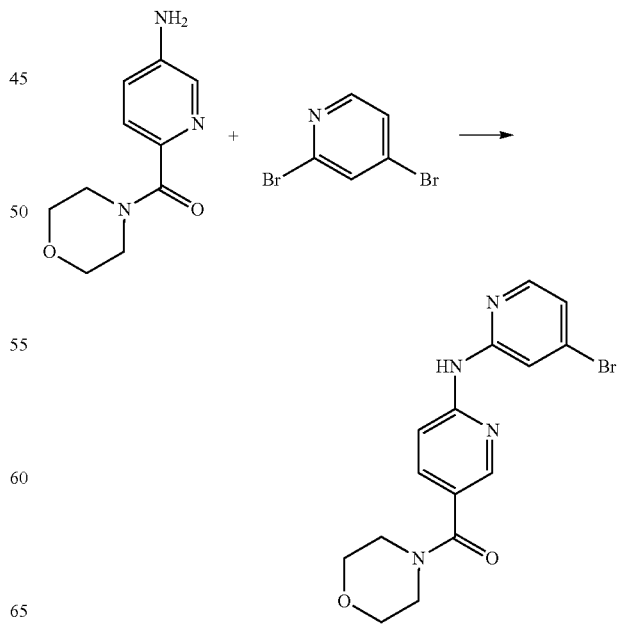

2,4-dibromopyridine (0.7 g, 3.34 mmol), (4-aminophenyl)(morpholino)methanone (733 mg, 3.54 mmol) and Cs$_2$CO$_3$ (1.92 g, 5.90 mmol) were dissolved in dioxane (10 ml). Under N$_2$ atmosphere, Pd$_2$(dba)$_3$ (135 mg, 0.15 mmol) and Xantphos (171 mg, 0.30 mmol) were added and the mixture was stirred at reflux temperature overnight. After the completion of the reaction, the mixture was cooled to room temperature, poured into water (100 ml), extracted with DCM (100 ml) and then washed with saturated aqueous solution of sodium chloride (100 ml). The organic layer was dried over sodium sulfate and concentrated. The residue was purified by silica gel column (petroleum ether:ethyl acetate=2:1). The desired product was obtained as a yellow solid (426 mg, yield 40%). $^1$H NMR (300 MHz, MeOD): δ 10.19 (s, 1H), 8.34 (d, J=2.3 Hz, 1H), 8.18-8.09 (m, 2H), 7.75 (dd, J=8.6, 2.3 Hz, 1H), 7.65 (d, J=8.7 Hz, 1H), 7.19-7.09 (m, 1H), 3.55 (d, J=23.3 Hz, 8H). LC-MS: 363[M+1]$^+$, t$_R$=1.210 min.

Step 2. Preparation of acetic acid 2-(6-tert-butyl-8-fluoro-1-oxo-1H-phthalazin-2-yl)-6-{2-[5-(morpholine-4-carbonyl)-pyridin-2-ylamino]-pyridin-4-yl}-benzyl ester

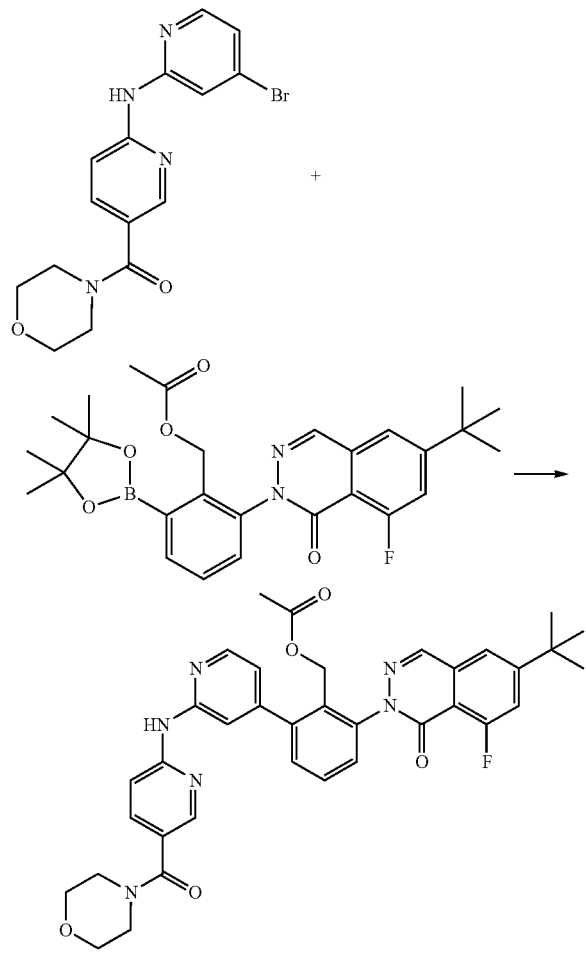

[6-(4-Bromo-pyridin-2-ylamino)-pyridin-3-yl]-morpholin-4-yl-methanone (200 mg, 0.55 mmol), acetic acid 2-(6-tert-butyl-8-fluoro-1-oxo-1H-phthalazin-2-yl)-6-(4,4,5,5-tetramethyl[1,3,2]dioxaborolan-2-yl)-benzyl ester (410 mg, 0.83 mmol) and K$_2$CO$_3$ (152 mg, 1.10 mmol) were dissolved in dioxane/H$_2$O (10:1, 11 ml). Under N$_2$ atmosphere, Pd$_2$(dba)$_3$ (50 mg, 0.055 mmol) and X-phos (105 mg, 0.22 mmol) was added and the mixture was stirred at reflux temperature overnight. After the completion of the reaction, the mixture was cooled to room temperature and filtered. The organic layer was washed with saturated brine, dried over sodium sulfate and concentrated. The residue was purified by silica gel column (petroleum ether:ethyl acetate=2:1). The desired product was obtained as a yellow solid (200 mg, yield 56%). LC-MS: 651[M+1]$^+$, t$_R$=1.397 min.

Example 6

Step 3. 6-tert-Butyl-8-fluoro-2-(2-hydroxymethyl-3-{2-[5-(morpholine-4-carbonyl)-pyridin-2-ylamino]-pyridin-4-yl}-phenyl)-2H-phthalazin-1-one

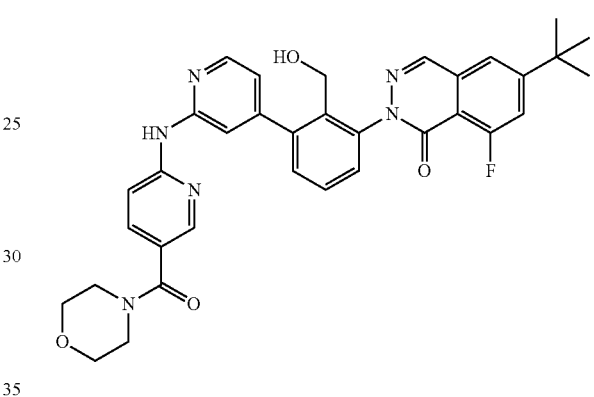

Acetic acid 2-(6-tert-butyl-8-fluoro-1-oxo-1H-phthalazin-2-yl)-6-{2-[5-(morpholine-4-carbonyl)-pyridin-2-ylamino]-pyridin-4-yl}-benzyl ester (200 mg, 0.31 mmol) was dissolved in methanol (10 ml). K$_2$CO$_3$ (86 mg, 0.62 mmol) was added at room temperature, and the mixture was stirred at that temperature for 2 hours. The mixture was poured into water (10 ml), extracted with DCM (100 ml) and then washed with saturated aqueous solution of sodium chloride (100 ml). The combined organic extract was dried over sodium sulfate and concentrated. The residue was purified by silica gel column (petroleum ether:ethyl acetate=1:2). The desired product was obtained as a white solid (130 mg, yield 69%). $^1$H NMR (300 MHz, MeOD): δ 8.36 (d, J=2.6 Hz, 1H), 8.22-8.18 (m, 2H), 7.73 (d, J=1.5 Hz, 2H), 7.65-7.60 (m, 2H), 7.57-7.51 (m, 1H), 7.50-7.46 (m, 1H), 7.38 (d, J=7.6 Hz, 2H), 7.00 (dd, J=5.2, 1.5 Hz, 1H), 4.36 (s, 2H), 3.59 (s, 8H), 1.36 (d, J=5.7 Hz, 9H). LC-MS: 609[M+1]$^+$, t$_R$=1.407 min. HPLC: 97.79% at 214 nm, 99.31% at 254 nm, t$_R$=3.479 min.

Synthesis of Compound I-7

Scheme G

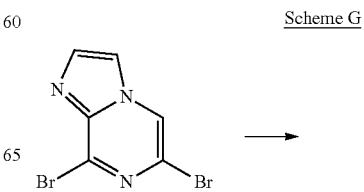

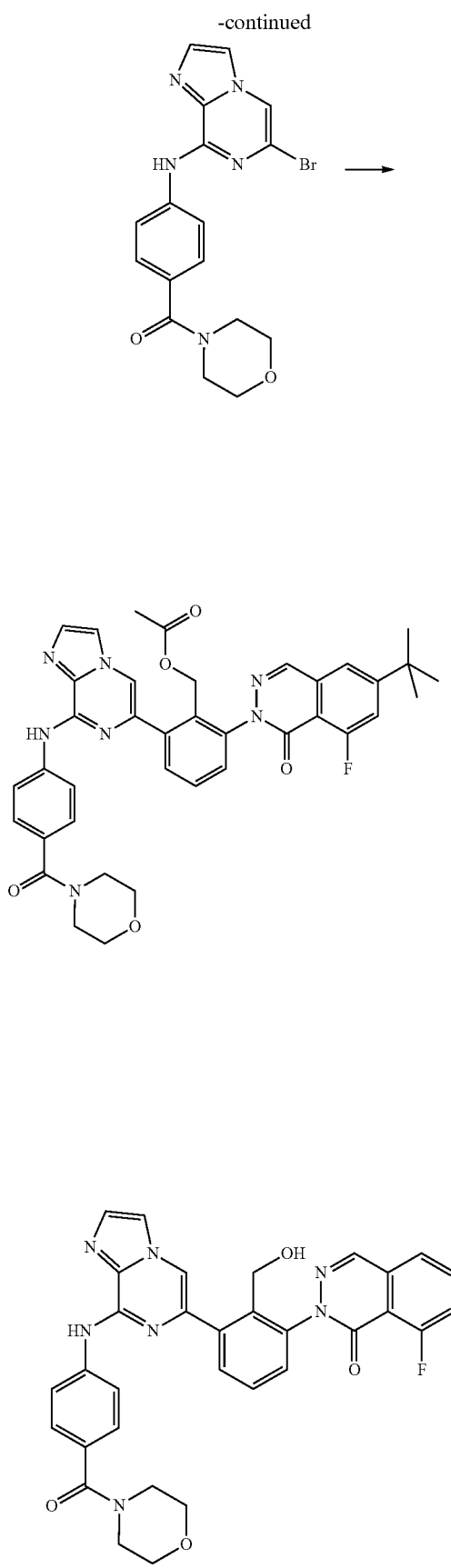

This example illustrates the synthesis of "6-tert-Butyl-8-fluoro-2-(2-hydroxymethyl-3-{8-[4-(morpholine-4-carbonyl)-phenylamino]-imidazo[1,2-c]pyrazin-6-yl}-phenyl)-2H-phthalazin-1-one"

Step 1. Preparation of [4-(6-bromo-imidazo[1,2-a]pyrazin-8-ylamino)-phenyl]-morpholin-4-yl-methanone A solution of 6,8-dibromoimidazo[1,2-a]pyrazine (500 mg, 1.8 mmol), (4-aminophenyl)(morpholino)-methanone (408 mg, 1.98 mmol) and CSA (356 mg, 1.53 mmol) in iPrOH (30 mL) was stirred at 90° C. overnight. The solvent was evaporated. The residue was dissolved in DCM (30 mL). A NaHCO$_3$ solution (10 mL) was added to adjust to pH=8. The organic layer was separated and dried over Na$_2$SO$_4$. The drying agent was removed by filtration and the resultant solution was concentrated in vacuo. The residue was purified through a silica-gel column (ethyl acetate:petroleum ether=1:1) to give the desired product as a yellow solid (500 mg, 69% yield)

LC-MS: 404 [M+1]$^+$, t$_R$=1.409 min. .

Step 2. Preparation of acetic acid 2-(6-tert-butyl-8-fluoro-1-oxo-1H-phthalazin-2-yl)-6-{8-[4-(morpholine-4-carbonyl)-phenylamino]-imidazo[1,2-a]pyrazin-6-yl}-benzyl ester Example 7

Step 3. 6-tert-Butyl-8-fluoro-2-(2-hydroxymethyl-3-{8-[4-(morpholine-4-carbonyl)-phenylamino]-imidazo[1,2-a]pyrazin-6-yl}-phenyl)-2H-phthalazin-1-one

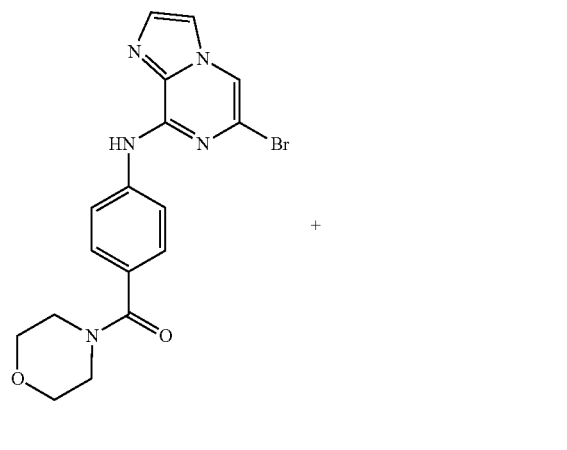

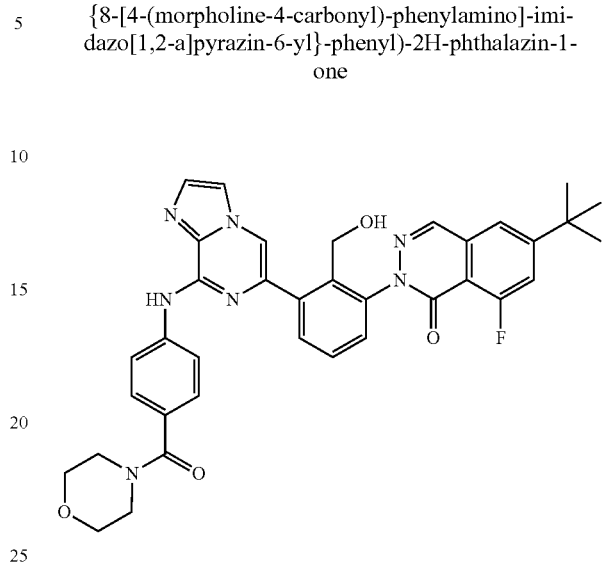

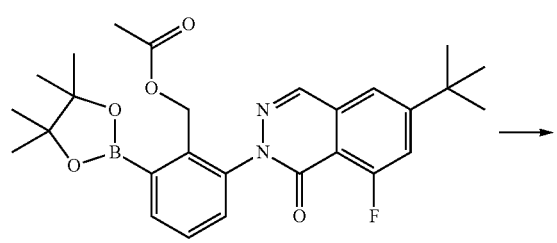

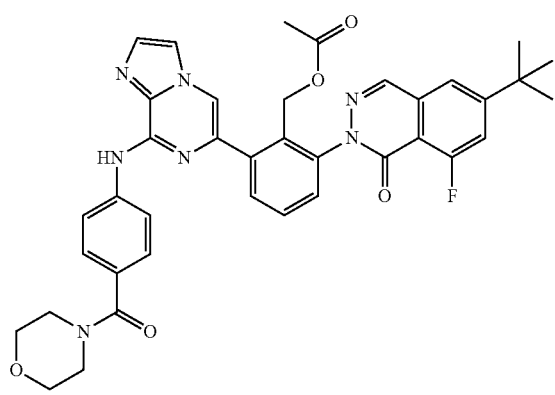

A solution of acetic acid 2-(6-tert-butyl-8-fluoro-1-oxo-1H-phthalazin-2-yl)-6-{8-[4-(morpholine-4-carbonyl)-phenylamino]-imidazo[1,2-a]pyrazin-6-yl}-benzyl ester (320 mg, 0.47 mmol) and $K_2CO_3$ (130 mg, 0.95 mmol) in MeOH (15 mL) was stirred at room temperature for 2 hours. The crude reaction mixture was filtered. The filter cake was washed with MeOH (5 mL) and dried to provide the desired product as a yellow solid (50 mg, 16% yield).

$^1$H NMR (301 MHz, DMSO) δ 9.95 (s, 1H), 8.51 (d, J=2.5 Hz, 1H), 8.31 (s, 1H), 8.20-8.04 (m, 3H), 7.86 (s, 1H), 7.71 (dd, J=16.3, 11.9 Hz, 3H), 7.55 (t, J=7.7 Hz, 1H), 7.40 (dd, J=27.6, 8.2 Hz, 3H), 4.65 (t, J=5.5 Hz, 1H), 4.45 (s, 3H), 3.58 (s, 5H), 3.49 (s, 4H), 1.37 (s, 9H).

LC-MS: 649 [M+1]$^+$, $t_R$=1.582 min.

Synthesis of compound I-8

Step 1. Preparation of (6-Bromo-imidazo[1,2-a]pyrazin-8-yl)-[4-(1-methyl-piperidin-4-yl)-phenyl]-amine

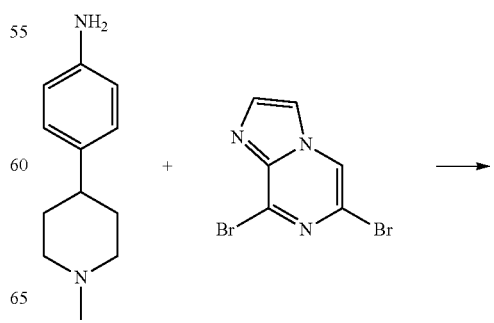

A solution of acetic acid 2-(6-tert-butyl-8-fluoro-1-oxo-1H-phthalazin-2-yl)-6-(4,4,5,5-tetramethyl[1,3,2]dioxaborolan-2-yl)-benzyl ester (491.3 mg, 1 mmol), [4-(6-bromo-imidazo[1,2-a]pyrazin-8-ylamino)-phenyl]-morpholin-4-yl-methanone (200 mg, 0.5 mmol), $K_2CO_3$ (137 mg, 1 mmol), $Pd_2(dba)_3$ (45.4 mg, 0.05 mmol) and X-Phos (94.5 mg, 0.2 mmol) in 30 mL dioxane and 10 mL water was stirred at 90° C. overnight. The crude reaction mixture was filtered. The filtrate was evaporated and the resulting residue was purified through a silica-gel column (ethyl acetate:petroleum ether=1:2) to give compound the desired product as a yellow oil (320 mg, 93% yield).

LC-MS: 690 [M+1]$^+$, $t_R$=1.618 min.

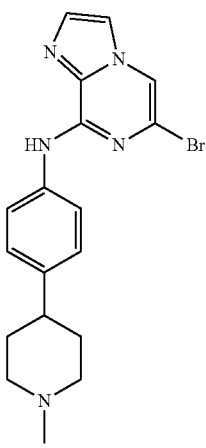

A solution of 6,8-dibromoimidazo[1,2-a]pyrazine (500 mg, 1.8 mmol), 4-(1-methylpiperidin-4-yl)benzenamine (376 mg, 1.98 mmol) and CSA (356 mg, 1.53 mmol) in iPrOH (30 mL) was stirred at 90° C. overnight. The solvent was evaporated. The residue was dissolved in DCM (30 mL), NaHCO$_3$ solution (10 mL) was added to adjust pH=8. The organic layer was dried over Na$_2$SO$_4$ and evaporated. The residue was purified through a silica-gel column (ethyl acetate:petroleum ether=1:1) to afford the desired product as a yellow solid (400 mg, 58% yield).

LC-MS: 388 [M+1]$^+$, t$_R$=1.402 min.

Step 2. Preparation of acetic acid 2-(6-tert-butyl-8-fluoro-1-oxo-1H-phthalazin-2-yl)-6-{8-[4-(1-methyl-piperidin-4-yl)-phenylamino]-imidazo[1,2-a]pyrazin-6-yl}-benzyl ester

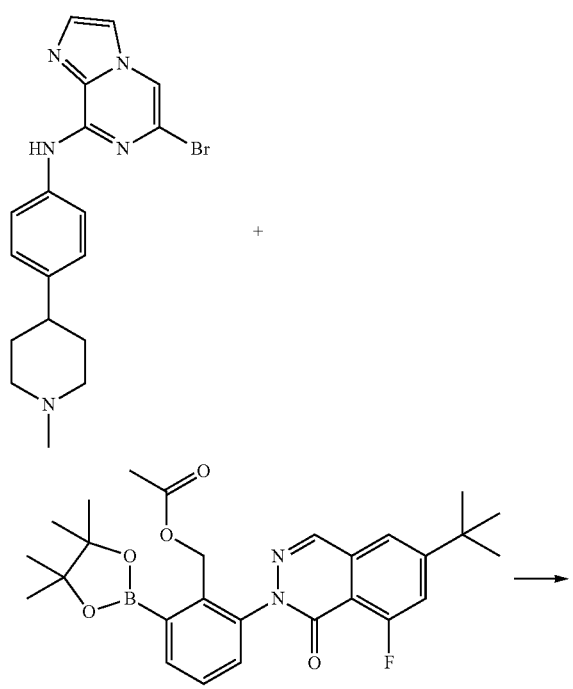

A solution of 2-(6-tert-butyl-8-fluoro-1-oxophthalazin-2(1H)-yl)-6-(4,4,5,5-tetramethyl-1,3,2-dioxaborolan-2-yl) benzyl acetate (491.3 mg, 1 mmol), (6-bromo-imidazo[1,2-a]pyrazin-8-yl)-[4-(1-methyl-piperidin-4-yl)-phenyl]-amine (200 mg, 0.52 mmol), K$_2$CO$_3$ (137 mg, 1 mmol), Pd$_2$(dba)$_3$ (45.4 mg, 0.05 mmol), X-phos (94.5 mg, 0.2 mmol) in 30 mL dioxane and 10 mL water was stirred at 90° C. overnight. The reaction mixture was filtered. The filtrate was evaporated and the residue was purified through a silica-gel column (ethyl acetate:petroleum ether=1:2) to give the desired product as a yellow oil (320 mg, 92% yield).

LC-MS: 674 [M+1]$^+$, t$_R$=1.539 min.

Example 8

Step 3. 6-tert-Butyl-8-fluoro-2-(2-hydroxymethyl-3-{8-[4-(1-methyl-piperidin-4-yl)-phenylamino]-imidazo[1,2-a]pyrazin-6-yl}-phenyl)-2H-phthalazin-1-one

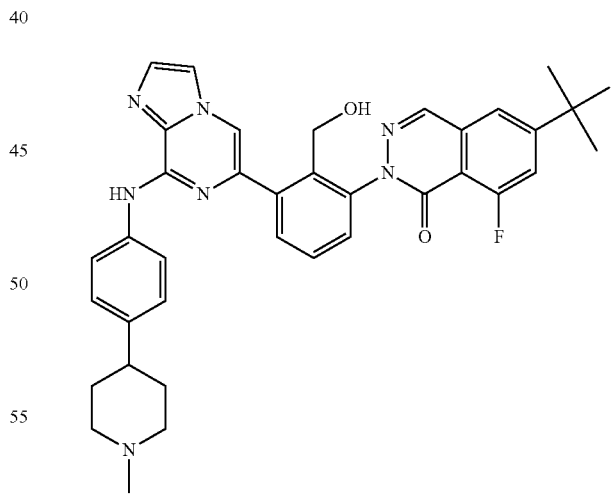

A solution of acetic acid 2-(6-tert-butyl-8-fluoro-1-oxo-1H-phthalazin-2-yl)-6-{8-[4-(1-methyl-piperidin-4-yl)-phenylamino]-imidazo[1,2-a]pyrazin-6-yl}-benzyl ester (150 mg, 0.22 mmol) and K$_2$CO$_3$ (62 mg, 0.44 mmol) in MeOH (15 mL) was stirred at room temperature for 2 hours. The reaction mixture was filtered. The filter cake was washed by MeOH (5 mL) and dried to afford 50 mg of the desired product as a yellow solid (36% yield).

$^1$H NMR (300 MHz, DMSO-$d_6$) δ ppm 0.91 (d, J=6.42 Hz, 3H) 1.09-1.30 (m, 2H) 1.37 (s and overlapping multiplet, 11H) 1.66 (d, J=12.09 Hz, 2H) 2.55 (d, J=12.09 Hz, 2H) 3.31 (s, 3H) 3.57 (d, J=12.09 Hz, 2H) 4.39 (br. s., 2H) 4.64 (br. s., 1H) 6.86 (d, J=9.07 Hz, 2H) 7.42 (d, J=7.55 Hz, 1H) 7.53 (t, J=7.74 Hz, 1H) 7.59-7.91 (m, 6H) 8.01 (s, 1H) 8.18 (s, 1H) 8.51 (d, J=2.27 Hz, 1H) 9.45 (s, 1H).

LC-MS: 632 [M+1]$^+$, $t_R$=1.560 min.

Synthesis of Compound I-9

Scheme H

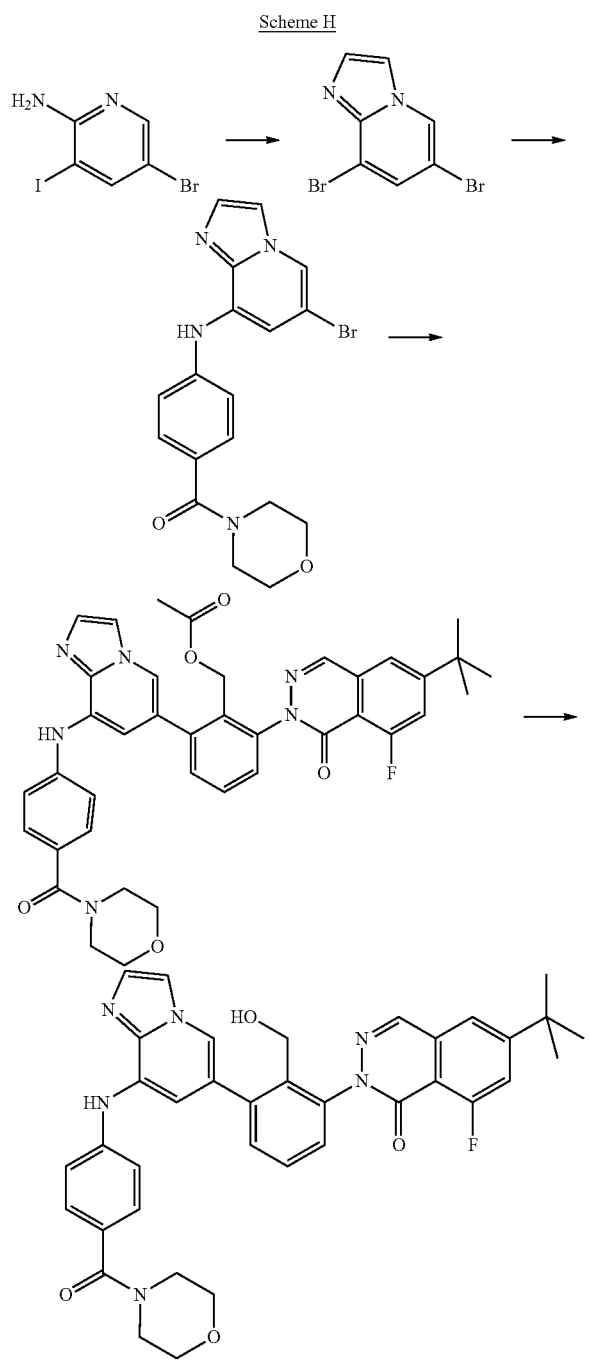

This example illustrates the synthesis of "6-tert-Butyl-8-fluoro-2-(2-hydroxymethyl-3-{8-[4-(morpholine-4-carbonyl)-phenylamino]-imidazo[1,2-c]pyridin-6-yl}-phenyl)-2H-phthalazin-1-one"

Step 1. Preparation of 6-Bromo-8-iodo-imidazo[1,2-a]pyridine

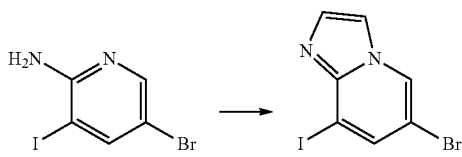 [SMILES: Nc1ncc(Br)cc1I ; Brc1cc(I)c2nccn2c1]

5-bromo-3-iodopyridin-2-amine (1.0 g, 3.34 mmol) and 2-bromo-1,1-dimethoxyethane were dissolved in ethanol (20 ml). To this solution was added a 50% mixture of HBr in water (4 ml). The mixture was stirred at reflux temperature overnight. After the completion of the reaction, the mixture was cooled to room temperature and filtered. The residue was suspended in DCM (10 ml) and stirred with the saturated aqueous solution of Na$_2$CO$_3$. The organic layer was separated and washed with saturated brine, dried over sodium sulfate and concentrated. The desired product was obtained as a yellow solid (950 mg, yield 88%). LC-MS: 323 [M+1]$^+$, $t_R$=1.299 min.

Step 2. Preparation of [4-(6-Bromo-imidazo[1,2-a]pyridin-8-ylamino)-phenyl]-morpholin-4-yl-methanone

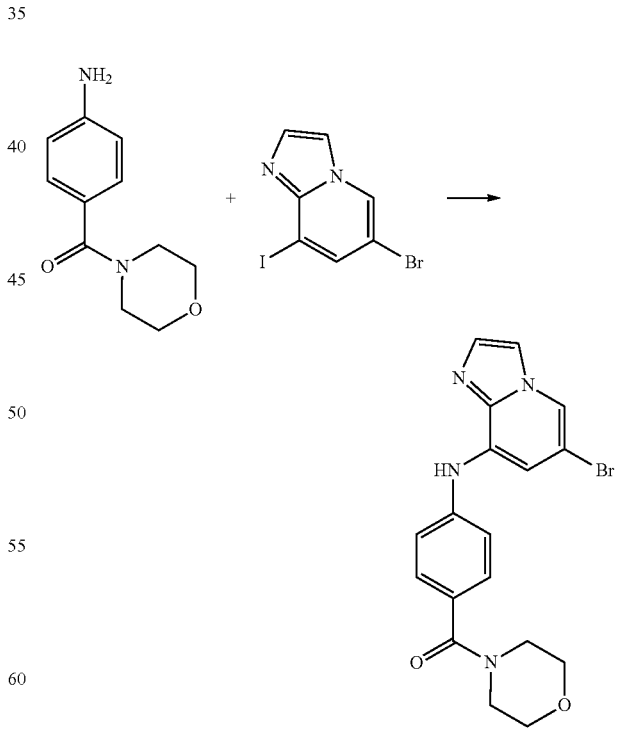

6-Bromo-8-iodo-imidazo[1,2-a]pyridine (500 mg, 1.53 mmol), (4-aminophenyl)(morpholino)-methanone (348 mg, 1.69 mmol) and CsCO$_3$ (998 mg, 3.06 mmol) were dissolved in dioxane (10 ml). Under N$_2$ atmosphere, Pd$_2$(dba)$_3$ (70 mg, 0.077 mmol) and Xantphos (89 mg, 0.153 mmol) were added and the mixture was stirred at reflux temperature overnight. After the completion of the reaction, the mixture was cooled to room temperature, poured into water (100 mL) and extracted with DCM (100 ml). The organic extracts were washed with saturated aqueous solution of sodium chloride (100 ml), dried over sodium sulfate and concentrated. The residue was purified by silica gel column (petroleum ether: ethyl acetate 1:2) to afford the desired product as a yellow solid (270 mg, yield 44%). LC-MS: 401[M+1]$^+$, $t_R$=1.257 min.

Step 3. Preparation of acetic acid 2-(6-tert-butyl-8-fluoro-1-oxo-1H-phthalazin-2-yl)-6-{8-[4-(morpholine-4-carbonyl)-phenylamino]-imidazo[1,2-a]pyridin-6-yl}-benzyl ester

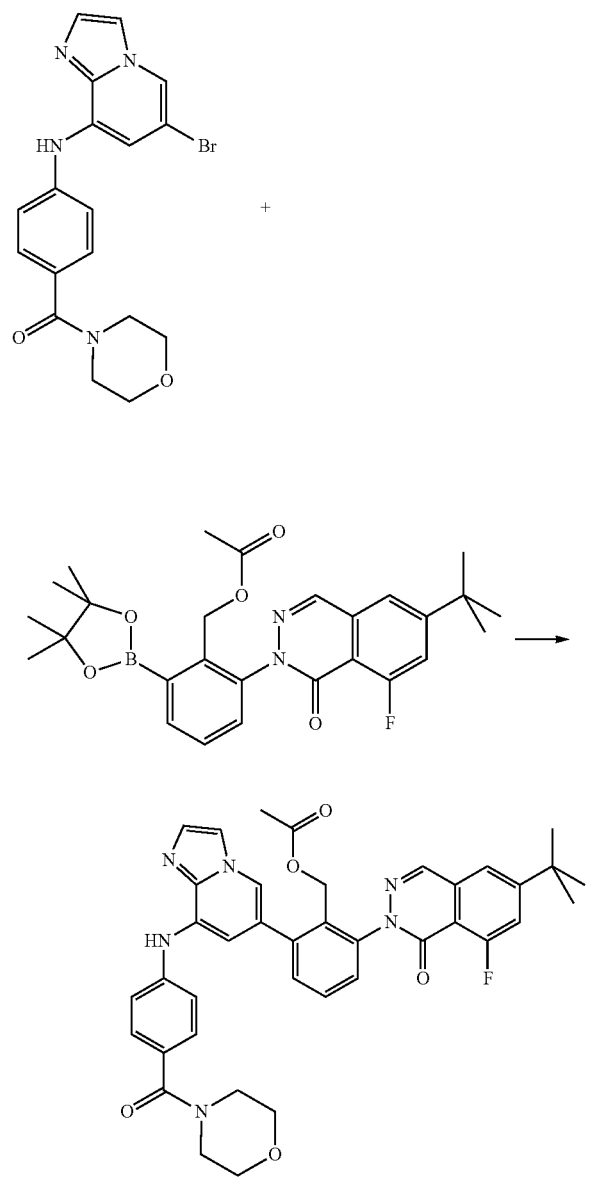

[4-(6-Bromo-imidazo[1,2-a]pyridin-8-ylamino)-phenyl]-morpholin-4-yl-methanone (270 mg, 0.68 mmol), 2-(6-tert-butyl-8-fluoro-1-oxophthalazin-2(1H)-yl)-6-(4,4,5,5-tetramethyl-1,3,2-dioxaborolan-2-yl)benzyl acetate (670 mg, 1.35 mmol) and $K_2CO_3$ (188 mg, 1.36 mmol) were dissolved in a 10:1 mixture of dioxane in $H_2O$ (11 ml). Under $N_2$ atmosphere, $Pd_2(dba)_3$ (62 mg, 0.068 mmol) and X-phos (129 mg, 0.27 mmol) were added and the mixture was stirred at reflux temperature overnight. After the completion of the reaction, the mixture was cooled to room temperature, poured into water (100 mL) and extracted by DCM (100 ml). The organic extracts were washed with saturated aqueous solution of sodium chloride (100 ml), dried over sodium sulfate and concentrated. The residue was purified by silica gel column (petroleum ether:ethyl acetate 2:1) to afford the desired product as a yellow solid (60 mg, yield 25%). LC-MS: 689[M+1]$^+$, $t_R$=1.506 min.

Example 9

Step 4. 6-tert-Butyl-8-fluoro-2-(2-hydroxymethyl-3-{8-[4-(morpholine-4-carbonyl)-phenylamino]-imidazo[1,2-a]pyridin-6-yl}-phenyl)-2H-phthalazin-1-one

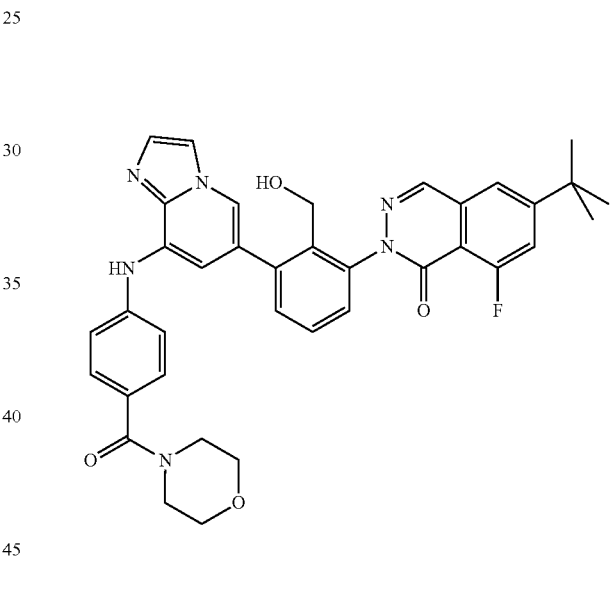

Acetic acid 2-(6-tert-butyl-8-fluoro-1-oxo-1H-phthalazin-2-yl)-6-{8-[4-(morpholine-4-carbonyl)-phenylamino]-imidazo[1,2-a]pyridin-6-yl}-benzyl ester (200 mg, 0.29 mmol) was dissolved in methanol (10 ml). To this solution was added $K_2CO_3$ (80 mg, 0.58 mmol) and the mixture was stirred at room temperature for 2 hours. After the completion of the reaction, the mixture was poured into water (10 ml), extracted by DCM (100 ml). The organic extracts were washed with saturated aqueous solution of sodium chloride (100 ml), dried over sodium sulfate and concentrated. The residue was purified by silica gel column (petroleum ether:ethyl acetate 1:3) to afford the desired product as a yellow solid (30 mg, yield 16%). $^1$H NMR (300 MHz, CDCl$_3$): δ 8.37 (d, J=2.7 Hz, 1H), 8.04 (d, J=1.3 Hz, 1H), 7.78 (s, 1H), 7.73 (d, J=1.7 Hz, 1H), 7.61 (d, J=1.7 Hz, 1H), 7.57 (d, J=1.6 Hz, 1H), 7.45 (dd, J=7.7, 5.7 Hz, 3H), 7.36 (dd, J=6.6, 2.7 Hz, 1H), 7.32 (s, 3H), 7.19 (d, J=1.4 Hz, 1H), 4.38 (s, 2H), 3.57 (s, 8H), 1.35 (s, 9H).

LC-MS: 647[M+1]$^+$, $t_R$=1.407 min. HPLC: 97.75% at 214 nm, 98.27% at 254 nm, $t_R$=3.633 min.

Synthesis of compound I-10

Example 10

6-tert-Butyl-8-fluoro-2-(2-hydroxymethyl-3-{8-[5-(morpholine-4-carbonyl)-pyridin-2-ylamino]imidazo[1,2-a]pyridin-6-yl}-phenyl)-2H-phthalazin-1-one

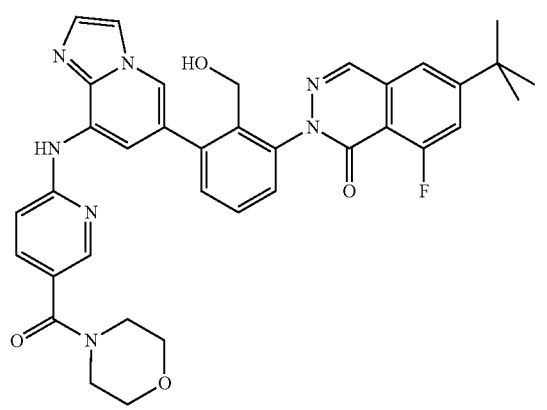

Preparation by a similar procedure to example 9 except substituting (6-amino-pyridin-3-yl)-morpholin-4-yl-methanone for (4-amino-phenyl)-morpholin-4-yl-methanone afforded the title compound as yellow solid (270 mg, 64%). $^1$H NMR (300 MHz, CDCl$_3$): δ 9.54 (s, 1H), 8.51 (d, J=2.7 Hz, 1H), 8.40 (d, J=1.5 Hz, 1H), 8.31 (d, J=2.1 Hz, 1H), 8.24 (d, J=1.5 Hz, 1H), 7.98 (d, J=1.2 Hz, 1H), 7.86 (d, J=1.8 Hz, 1H), 7.76-7.68 (m, 2H), 7.60-7.45 (m, 5H), 4.64 (t, J=5.1 Hz, 1H), 4.37-4.35 (m, 2H), 3.60-3.51 (m, 8H), 1.38 (s, 9H). LC-MS: 648 [M+1]$^+$, $t_R$=1.418 min. HPLC: 99.82% at 214 nm, 99.88% at 254 nm, $t_R$=3.510 min.

Synthesis of Compound I-11

Scheme I

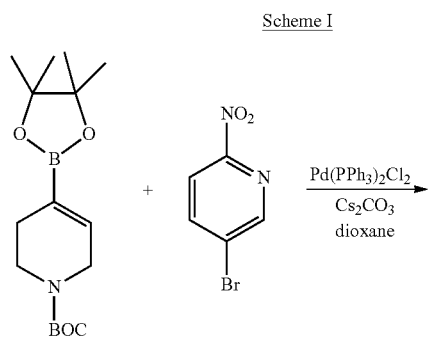

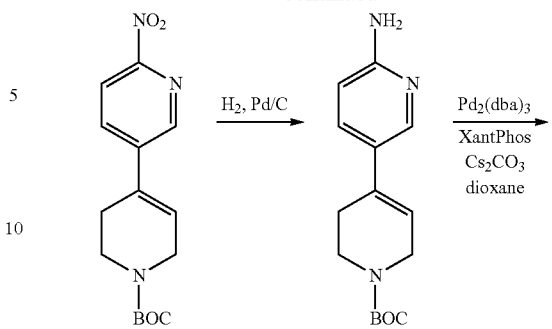

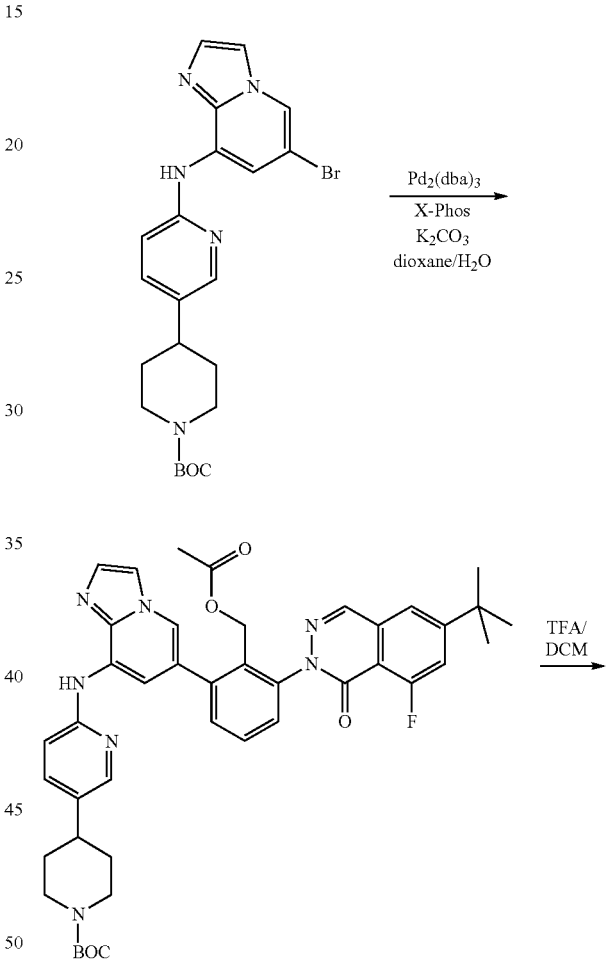

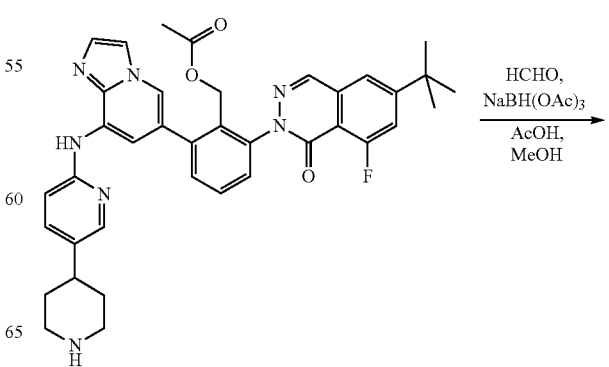

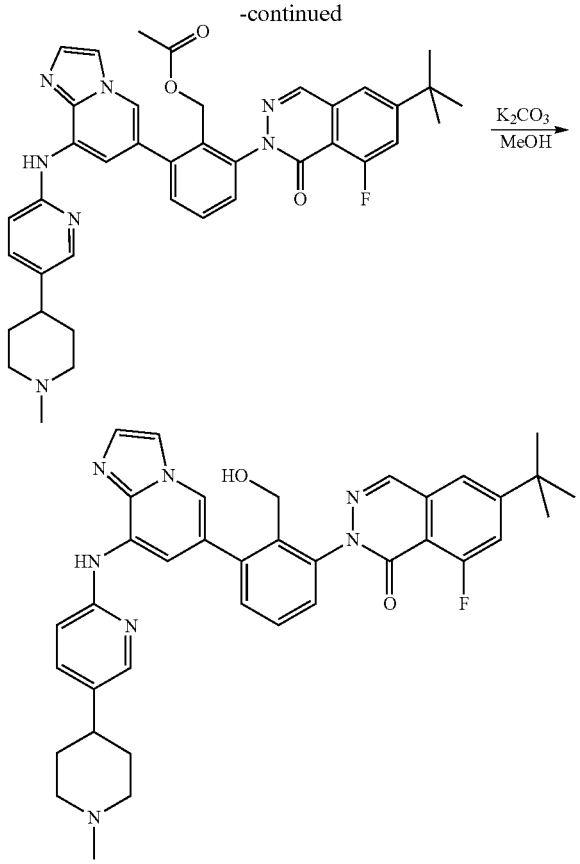

This example illustrates the synthesis of "6-tert-Butyl-8-fluoro-2-{2-hydroxymethyl-3-[8-(1'-methyl-1',2',3',4',5',6'-hexahydro-[3,4']bipyridinyl-6-ylamino)-imidazo[1,2-a]pyridin-6-yl]-phenyl}-2H-phthalazin-1-one".

Step 1. Preparation of 6-nitro-3',6'-dihydro-2'H-[3,4'] bipyridinyl-1'-carboxylic acid tert-butyl ester

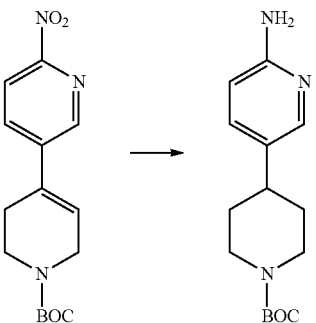

A solution of 4-(4,4,5,5-tetramethyl-[1,3,2]dioxaborolan-2-yl)-3,6-dihydro-2H-pyridine-1-carboxylic acid tert-butyl ester (5.38 g, 17.40 mmol), 5-bromo-2-nitro-pyridine (3.52 g, 17.40 mmol), $Cs_2CO_3$ (11.34 g, 34.8 mmol), and $Pd(PPh_3)_2Cl_2$ (1.27 g, 1.74 mmol) in dioxane (50 mL) was stirred at 85° C. under $N_2$ atmosphere overnight. TLC showed a complete reaction. The solution was poured onto water and extracted with ethyl acetate. The combined organic layers were washed with brine, dried over $Na_2SO_4$, and concentrated. Purification by column chromatography on silica gel (petroleum ether: ethyl acetate, 2:1 eluent) afforded the desired product as yellow solid (3.37 g, 64%). $^1$H NMR (300 MHz, $CDCl_3$): δ 8.63 (d, J=2.4 Hz, 1H), 8.20 (d, J=8.4 Hz, 1H), 7.93 (dd, J=8.4, 2.4 Hz, 1H), 6.31 (s, 1H), 4.17-4.14 (m, 2H), 3.68 (t, J=5.7 Hz, 1H), 2.57-2.54 (m, 2H), 1.49 (s, 9H).

Step 2. Preparation of 6-amino-3',4',5',6'-tetrahydro-2'H-[3,4']bipyridinyl-1'-carboxylic acid tert-butyl ester

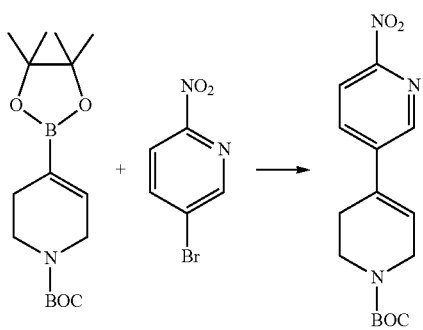

To a solution of 6-nitro-3',6'-dihydro-2'H-[3,4']bipyridinyl-1'-carboxylic acid tert-butyl ester (3 g, 9.84 mmol) in $CH_3OH$: DCM (40 mL, v/v=3:1) was added Pd/C (600 mg) and the mixture was stirred at room temperature under a hydrogen atmosphere overnight. TLC showed a complete reaction. The solution was filtered and the resulting filtrate was evaporated to dryness to give the crude product, which used directly in the next step (2.6 g, 96%). $^1$H NMR (300 MHz, $CDCl_3$): δ 7.89 (d, J=2.4 Hz, 1H), 7.26 (dd, J=8.4, 2.4 Hz, 1H), 6.46 (d, J=8.4 Hz, 1H), 4.36 (bs, 2H), 4.23-4.19 (m, 2H), 2.81-2.73 (m, 2H), 2.58-2.47 (m, 1H), 1.78-1.73 (m, 2H), 1.61-1.51 (m, 2H), 1.47 (s, 9H).

Step 3. Preparation of 6-(6-Bromo-imidazo[1,2-a]pyridin-8-ylamino)-3',4',5',6'-tetrahydro-2'H-[3,4']bipyridinyl-1'-carboxylic acid tert-butyl ester

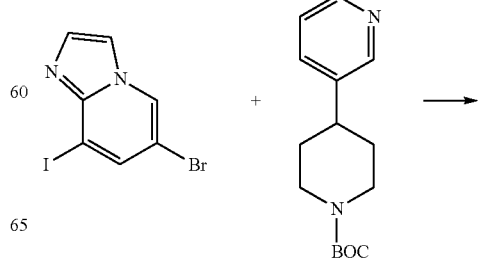

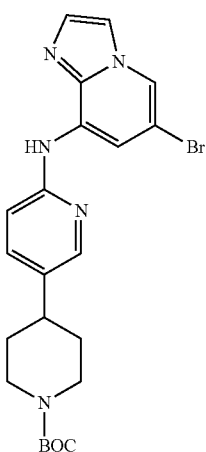

A mixture of 6-amino-3',4',5',6'-tetrahydro-2'H-[3,4']bipyridinyl-1'-carboxylic acid tert-butyl ester (971 mg, 3.0063 mmol), 6-bromo-8-iodo-imidazo[1,2-a]pyridine (1 g, 3.6075 mmol), Pd$_2$(dba)$_3$ (138 mg, 0.1503 mmol), XantPhos (174 mg, 0.3006 mmol), and Cs$_2$CO$_3$ (2 g, 6.0126 mmol) were combined in dioxane (20 mL) and the solution was stirred at 90° C. under N$_2$ atmosphere for 5 h at which point the TLC showed little starting material remained. The solution was poured onto water and extracted with ethyl acetate. The combined organic layers were washed with brine, dried over Na$_2$SO$_4$, and concentrated. Purification by column chromatography on silica gel (DCM: MeOH, 60:1 eluent) afforded the desired product as yellow solid (1.15 g, 81%). $^1$H NMR (300 MHz, CDCl$_3$): δ 8.44 (d, J=1.5 Hz, 1H), 8.20 (d, J=2.1 Hz, 1H), 7.92 (s, 1H), 7.84 (d, J=1.5 Hz, 1H), 7.49 (s, 2H), 7.42 (dd, J=8.4, 2.4 Hz, 1H), 6.84 (d, J=8.4 Hz, 1H), 4.27-4.23 (m, 2H), 2.85-2.77 (m, 2H), 2.68-2.58 (m, 1H), 1.84-1.79 (m, 2H), 1.67-1.57 (m, 2H), 1.48 (s, 9H).

Step 4. Preparation of 6-{6-[2-acetoxymethyl-3-(6-tert-butyl-8-fluoro-1-oxo-1H-phthalazin-2-yl)-phenyl]-imidazo[1,2-a]pyridin-8-ylamino}-3',4',5',6'-tetrahydro-2'H-[3,4']pyridinyl-1'-carboxylic acid tert-butyl ester

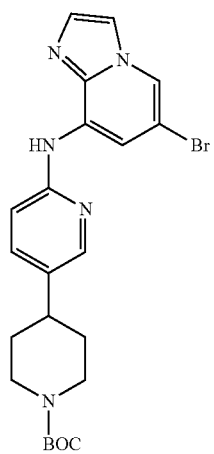

+

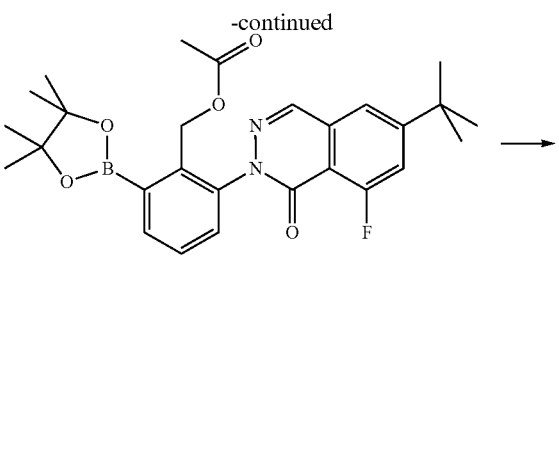

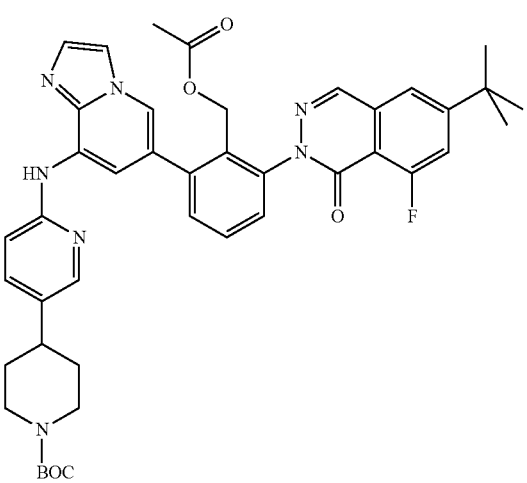

A mixture of 6-(6-Bromo-imidazo[1,2-a]pyridin-8-ylamino)-3',4',5',6'-tetrahydro-2'H-[3,4']bipyridinyl-1'-carboxylic acid tert-butyl ester (471 mg, 1 mmol), 2-(6-tert-butyl-8-fluoro-1-oxophthalazin-2(1H)-yl)-6-(4,4,5,5-tetramethyl-1,3,2-dioxaborolan-2-yl)benzyl acetate (990 mg, 2 mmol), Pd$_2$(dba)$_3$ (92 mg, 0.1 mmol), X-Phos (191 mg, 0.4 mmol) and K$_2$CO$_3$ (2 g, 6.01 mmol) in dioxane (15 mL) and H$_2$O (1.5 mL) was stirred at 100° C. under N$_2$ atmosphere. After stirring for 3 h, TLC showed a complete reaction. The solution was poured onto water and extracted with ethyl acetate. The combined organic layers were washed with brine, dried over Na$_2$SO$_4$, and concentrated. Purification by column chromatography on silica gel (petroleum ether:ethyl acetate, 3:5 eluent) afforded the desired product as yellow solid (310 mg, 41%). $^1$H NMR (300 MHz, CDCl$_3$): δ 9.13 (s, 1H), 8.52-8.51 (m, 1H), 8.36-8.35 (m, 1H), 8.14-8.12 (m, 2H), 7.96 (s, 1H), 7.86 (s, 1H), 7.75 (d, J=13.2 Hz, 1H), 7.67-7.50 (m, 5H), 7.35 (d, J=8.4 Hz, 1H), 4.92 (s, 2H), 2.80-2.72 (m, 2H), 2.64-2.56 (m, 1H), 1.74-1.69 (m, 2H), 1.63-1.62 (m, 2H), 1.54-1.44 (m, 2H), 1.41 (s, 9H), 1.38 (s, 9H).

Step 5. Preparation of acetic acid 2-(6-tert-butyl-8-fluoro-1-oxo-1H-phthalazin-2-yl)-6-[8-(1',2',3',4',5',6'-hexahydro-[3,4']bipyridinyl-6-ylamino)-imidazo[1,2-a]pyridin-6-yl]-benzyl ester

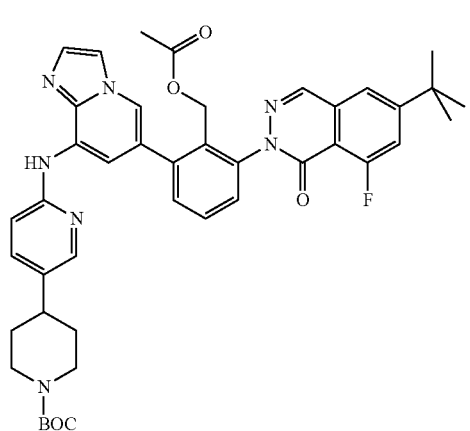

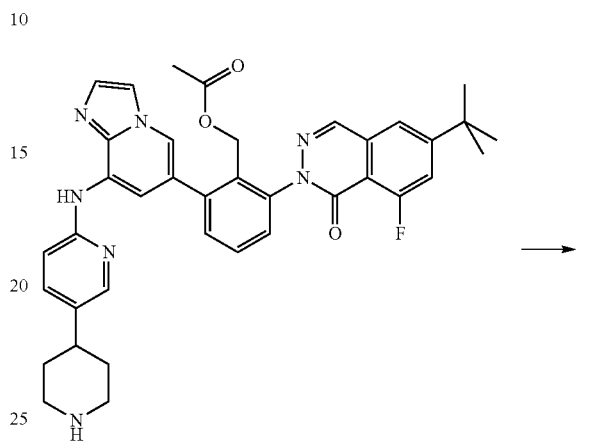

To the solution of 6-{6-[2-acetoxymethyl-3-(6-tert-butyl-8-fluoro-1-oxo-1H-phthalazin-2-yl)phenyl]-imidazo[1,2-a]pyridin-8-ylamino}-3',4',5',6'-tetrahydro-2'H-[3,4']bipyridinyl-1'-carboxylic acid tert-butyl ester (280 mg, 0.3689 mmol) in DCM (8 mL) was added TFA (1.4 mL) and the solution was stirred at room temperature for one hour. TLC showed a complete reaction. The solution was poured onto water and extracted with ethyl acetate. The combined organic layers were washed with brine, dried over Na$_2$SO$_4$, and concentrated to give the crude product used directly to the next step (260 mg). LC-MS: 660 [M+1]$^+$, t$_R$=1.270 min.

Step 6. Preparation of acetic acid 2-(6-tert-butyl-8-fluoro-1-oxo-1H-phthalazin-2-yl)-6-[8-(1'-methyl-1',2',3',4',5',6'-hexahydro-[3,4']pyridinyl-6-ylamino)-imidazo[1,2-a]pyridin-6-yl]-benzyl ester

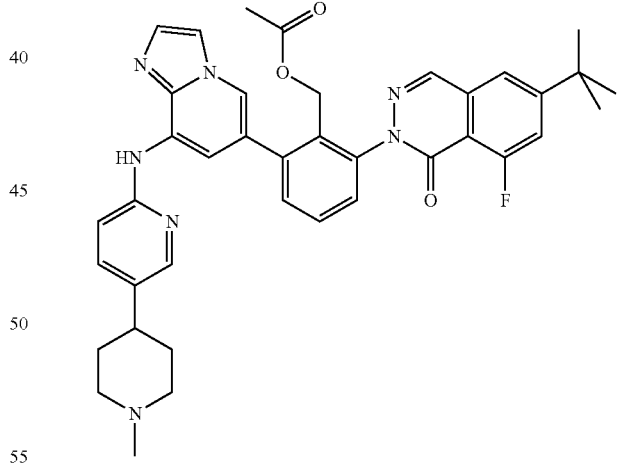

To a solution of acetic acid 2-(6-tert-butyl-8-fluoro-1-oxo-1H-phthalazin-2-yl)-6-[8-(1',2',3',4',5',6'-hexahydro-[3,4']bipyridinyl-6-ylamino)-imidazo[1,2-a]pyridin-6-yl]-benzyl ester (260 mg, 0.3945 mmol) in CH$_3$OH (10 mL) was added formaldehyde (163 mg of 37%). After stirring for 10 minutes at room temperature, two drops of acetic acid were added followed by NaBH(OAc)$_3$ (418 mg, 1.9727 mmol). The mixture was stirred at room temperature for 1 h. TLC showed a complete reaction. The solution was washed with water and extracted with ethyl acetate. The combined organic layers

Example 11

Step 7. 6-tert-Butyl-8-fluoro-2-{2-hydroxymethyl-3-[8-(1'-methyl-1',2',3',4',5',6'-hexahydro-[3,4']bipyridinyl-6-ylamino)-imidazo[1,2-a]pyridin-6-yl]-phenyl}-2H-phthalazin-1-one

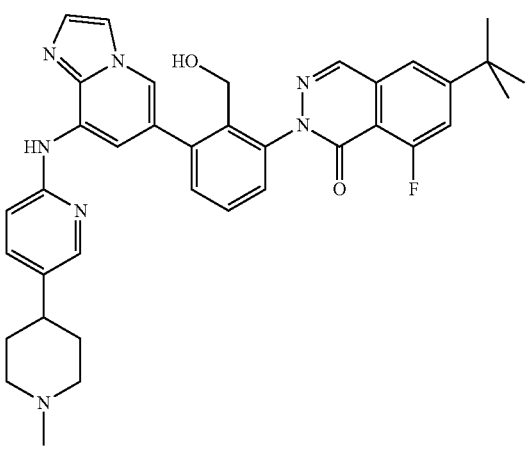 [SMILES: CN1CCC(c2ccc(Nc3cc(-c4cccc(-n5ncc6cc(C(C)(C)C)cc(F)c6c5=O)c4CO)cn4ccnc34)nc2)CC1]

A solution of acetic acid 2-(6-tert-butyl-8-fluoro-1-oxo-1H-phthalazin-2-yl)-6-[8-(1'-methyl-1',2',3',4',5',6'-hexahydro-[3,4']bipyridinyl-6-ylamino)-imidazo[1,2-a]pyridin-6-yl]-benzyl ester (270 mg, 0.4012 mmol) and K₂CO₃ (166 mg, 1.2036 mmol) in CH₃OH (15 mL) was stirred at room temperature for 3 h. TLC showed a complete reaction. The solution was poured onto water and extracted with ethyl acetate. The combined organic layers were washed with brine, dried over Na₂SO₄, and concentrated to give the desired product (200 mg) with high purity.

$^1$H NMR (300 MHz, CDCl₃): δ 9.07 (s, 1H), 8.50 (d, J=2.4 Hz, 1H), 8.33 (s, 1H), 8.15 (s, 1H), 8.09 (d, J=2.4 Hz, 1H), 7.95 (s, 1H), 7.86 (d, J=1.5 Hz, 1H), 7.73 (dd, J=13.2, 1.8 Hz, 1H), 7.57-7.43 (m, 5H), 7.35 (d, J=8.4 Hz, 1H), 4.63 (bs, 1H), 2.85-2.81 (m, 2H), 2.43-2.32 (m, 2H), 2.17 (s, 3H), 1.97-1.88 (m, 2H), 1.71-1.60 (m, 4H), 1.38 (s, 9H). LC-MS: 632 [M+1]⁺, t$_R$=1.392 min. HPLC: 95.50% at 214 nm, 96.03% at 254 nm, t$_R$=3.198 min.

Synthesis of Compound I-12

Step 1. Preparation of (6-Bromo-pyridin-3-yl)-morpholin-4-yl-methanone

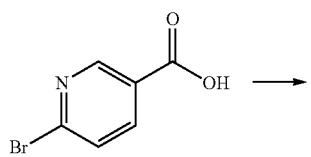
→
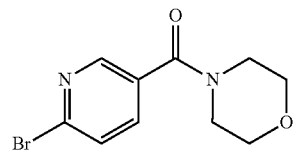

The mixture of 6-bromonicotinic acid (700 mg, 3.5 mmol), morpholine (391 mg, 4.5 mmol), HATU (220 mg, 0.59 mmol) and DIPEA (0.3 mL) in 10 mL of dry THF was stirred at room temperature for 14 hours. The reaction solution was evaporated to dryness. To the residue was added 20 mL of 0.5N hydrochloride, and the mixture was extracted with ethyl acetate (50 mL×3). The organic layer was dried over sodium sulfate and concentrated to give (6-bromopyridin-3-yl)(morpholino)methanone (750 mg, 79%). LC-MS: 271, 273 [M+H]⁺, t$_R$=1.290 min.

Step 2. Preparation of [6-(6-chloro-pyrimidin-4-ylamino)-pyridin-3-yl]-morpholin-4-yl-methanone

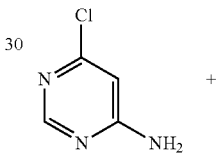
+

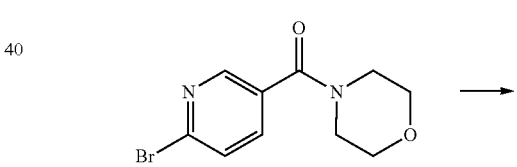
→

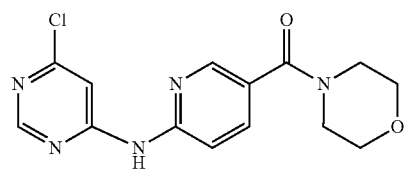

To a stirred solution of (6-bromopyridin-3-yl)(morpholino)methanone (0.75 g, 2.78 mmol) in toluene (5 mL) was added 6-chloropyrimidin-4-amine (0.43 g, 3.33 mmol), Pd₂(dba)₃ (100 mg, 0.3 mmol), Davephos (157 mg, 0.4 mmol) and NaOt-Bu (848 mg, 8 mmol). The mixture was stirred at 150° C. for 13 hrs under N₂. The mixture was evaporated and the residue was taken up in ethyl acetate (50 mL) and H₂O (20 mL). The organic phase was washed with H₂O (2×20 mL) and then brine (2×20 mL) and dried over Na$_2$SO$_4$. After filtration and concentration, the final product (350 mg, 40%) was obtained as yellow solid. LC-MS: 320.1 [M+H]$^+$, t$_R$=1.306 min.

Step 3. Preparation of acetic acid 2-(6-tert-butyl-8-fluoro-1-oxo-1H-phthalazin-2-yl)-6-{6-[5-(morpholine-4-carbonyl)-pyridin-2-ylamino]-pyrimidin-4-yl}-benzyl ester

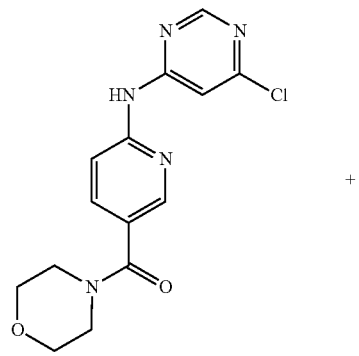

+

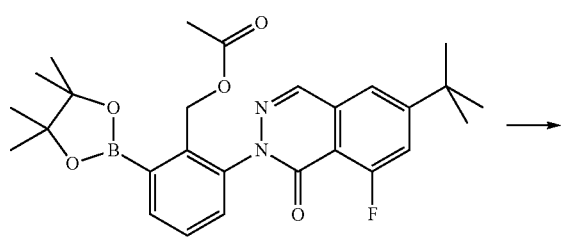

→

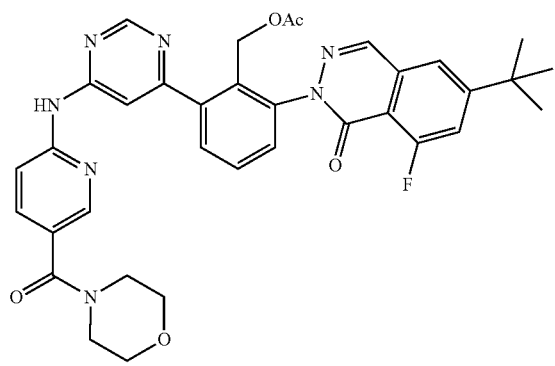 [SMILES: CC(=O)OCc1c(-c2cc(Nc3ccc(C(=O)N4CCOCC4)cn3)ncn2)cccc1-n1ncc2cc(C(C)(C)C)cc(F)c2c1=O]

To a stirred solution of (6-(6-chloropyrimidin-4-ylamino)pyridin-3-yl)(morpholino)methanone (0.15 g, 0.45 mmol) in 1,4-dioxane (5 mL) was added 2-(6-tert-butyl-8-fluoro-1-oxophthalazin-2(1H)-yl)-6-(4,4,5,5-tetramethyl-1,3,2-dioxaborolan-2-yl)benzyl acetate (0.250 g, 0.5 mmol), Pd(PPh$_3$)$_4$ (30 mg, 0.08 mmol), Na$_2$CO$_3$ (212 mg, 2 mmol) and H$_2$O (2 mL). The mixture was stirred at 80° C. for 13 hrs under N$_2$. The mixture was evaporated and ethyl acetate (50 mL) and H$_2$O (20 mL) were added to the resulting residue. The organic phase was washed with H$_2$O (2×20 mL), brine (2×20 mL) and dried over Na$_2$SO$_4$. After filtration and concentration, the final product (90 mg, 30%) was obtained as yellow solid. LC-MS: 652.2 [M+H]$^+$, t$_R$=1.499 min.

Example 12

Step 5. Preparation of 6-tert-butyl-8-fluoro-2-(2-hydroxymethyl-3-{6-[5-(morpholine-4-carbonyl)-pyridin-2-ylamino]-pyrimidin-4-yl}-phenyl)-2H-phthalazin-1-one

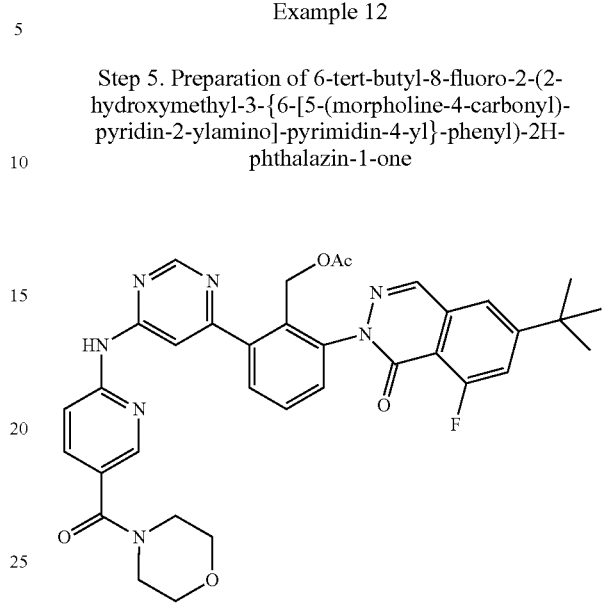

To a solution of 2-(6-tert-butyl-8-fluoro-1-oxophthalazin-2(1H)-yl)-6-(6-(5-(morpholine-4-carbonyl)pyridin-2-ylamino)pyrimidin-4-yl)benzyl acetate (90 mg, 0.14 mmol) in 1,4-dioxane (5 mL) was added 1N NaOH (10 mL). The mixture was stirred at room temperature for 2 hrs. The mixture was acidified to pH=2, followed by addition of ethyl acetate (50 mL) and H$_2$O (20 mL). The organic phase was washed with H$_2$O (2×20 mL), then brine (2×20 mL) and dried over Na$_2$SO$_4$. After filtration and concentration, the residue was purified by prep-HPLC to afford 6-tert-butyl-8-fluoro-2-(2-(hydroxymethyl)-3-(6-(5-(morpholine-4-carbonyl)pyridin-2-ylamino)pyrimidin-4-yl)phenyl)-phthalazin-1(2H)-one (30 mg, 36%). $^1$H NMR (300 MHz, CD3OD): δ 8.98 (s, 1H), 8.52-8.48 (m, 2H), 8.39 (s, 1H), 7.99-7.95 (m, 1H), 7.85 (s, 1H), 7.73-7.68 (m, 5H), 4.55 (s, 2H), 3.72 (brs, 8H), 1.46 (s, 9H). LC-MS (ESI): 610.3, [M+1]$^+$ HPLC: 97.17% at 214 nm, 99.01% at 254 nm, t$_R$=5.761 min.

Preparation of I-13

Scheme J

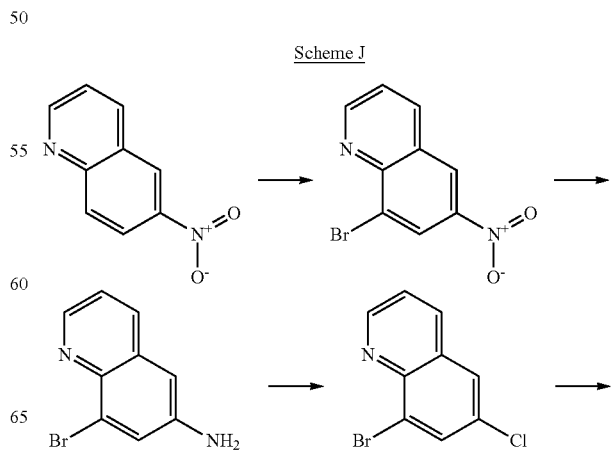

-continued

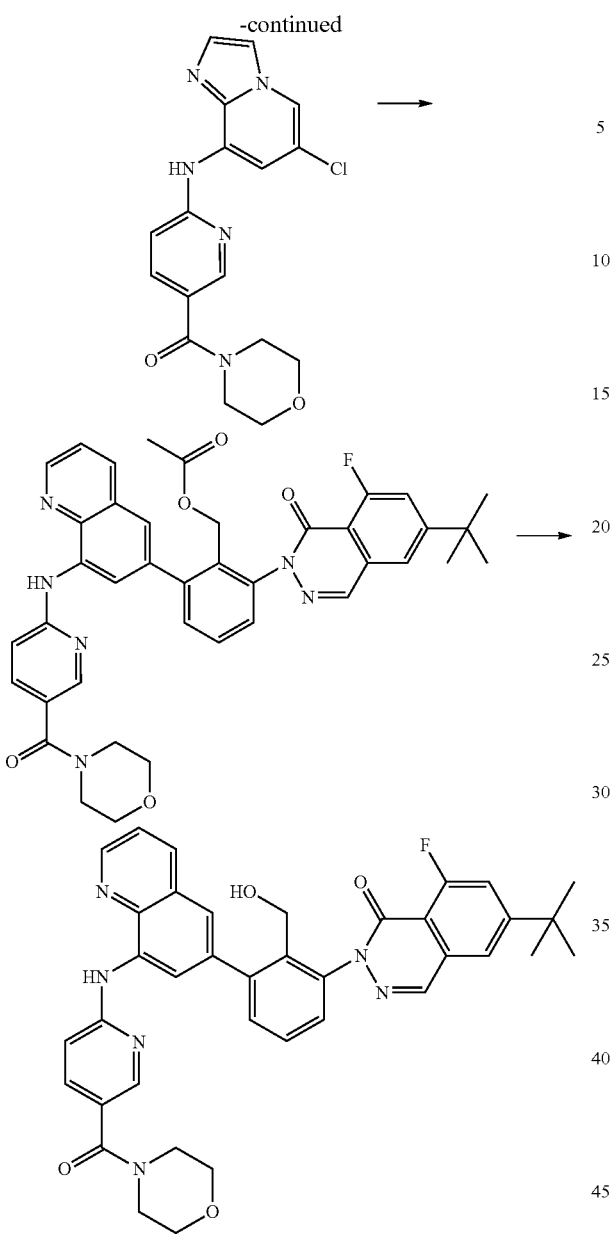

This example illustrates the synthesis of "6-tert-butyl-8-fluoro-2-(2-hydroxymethyl-3-{8-[5-(morpholine-4-carbonyl)-pyridin-2-ylamino]-quinolin-6-yl}-phenyl)-2H-phthalazin-1-one"

Step 1. Preparation of 8-bromo-6-nitroquinoline

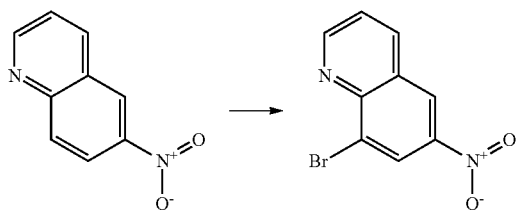 [SMILES: O=[N+]([O-])c1ccc2ncccc2c1 ; O=[N+]([O-])c1cc(Br)c2ncccc2c1]

To a flask containing 6-nitroquinoline (4 g, 23 mmol) in sulfuric acid (20 ml) was added N-bromo-succinimide (5.31 g, 29.9 mmol). The mixture was heated to 60° C. (oil bath) for 6 hours and then stored in a freezer overnight. The crude reaction mixture was poured into a beaker containing ice (250 ml). The material was basified by adding first solid sodium bicarbonate and then a saturated solution of sodium bicarbonate (to a pH of about 10). During this procedure ethyl acetate (60 ml) was also added. The material was filtered to remove insoluble material and the filtrate transferred to a reparatory funnel. Ethyl acetate (100 ml) was added and the biphasic material shaken. The organic phase was collected and shaken with an equal volume of brine solution. The ethyl acetate phase was collected and the aqueous phases were back extracted with ethyl acetate (2×100 ml). The combined organic phase was stripped to provide a solid. The solid from the above filtration was taken up in hot ethyl acetate (60 ml). The material was cooled to ambient, dried over magnesium sulfate and filtered. The solvent was stripped and the crude solid product was combined with the material obtained from aqueous work up. This material was crystallized from hot ethyl acetate/hexane to provide the desired product as a yellow powder (2.05 g).

$(M+H)^+$=253/255 m/e.

Step 2. Preparation of 8-bromoquinolin-6-amine

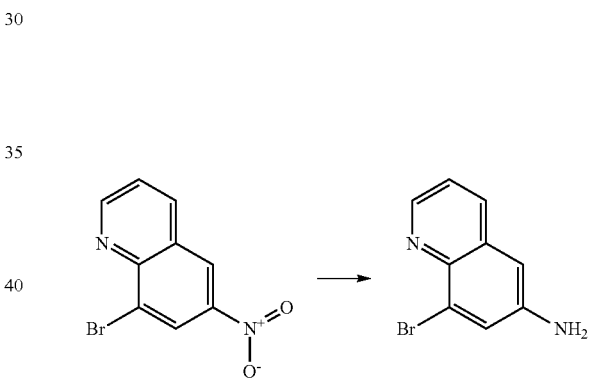

To a flask containing 8-bromo-6-nitroquinoline (2.05 g, 8.1 mmol), electrolytic iron (2.26 g, 40.5 mmol) and ammonium chloride (2.25 g, 42.1 mmol) was added ethanol (20 ml) and water (10 ml). The flask was fitted with an efficient reflux condenser and then heated to near reflux (oil bath) for 3 hours. The hot material was then filtered through a plug of celite and rinsed well with hot methanol (100 ml). The solvent was removed. The residue was taken up in ethyl acetate (60 ml) and water (60 ml) and transferred to a separatory funnel, agitated and the organic phase collected. The organic phase was washed with an equal volume of brine. The aqueous phases were back extracted with ethyl acetate (2×50 ml). The combined ethyl acetate extracts were dried over $MgSO_4$, and concentrated in vacuo. The resulting residue was crystallized from hot dichloromethane/hexanes to provide the desired product as a brown powder (860 mg)

$(M+H)^+$=223/225 m/e.

Step 3. Preparation of 8-bromo-6-chloroquinoline

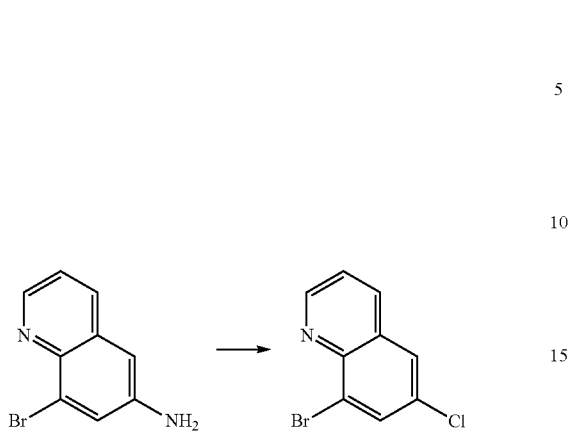

8-Bromoquinolin-6-amine (300 mg, 1.34 mmol) was taken up in concentrated hydrochloric acid (8 ml) and cooled to 0° C. (ice bath). Sodium nitrite (1.86 gm, 26.9 mmol) was added in three equal portions over 10 minutes. The mixture was removed from the cooling bath and copper (I) chloride (3.33 g, 33.6 mmol) was added in 3 portions, over about 6 minutes. On stirring a green-black rising foam developed. Stirring was continued for 45 minutes and then the reaction mixture was cooled to 0° C. (ice bath). A mixture of ice water (75 ml) and ammonium hydroxide (75 ml) was added with vigorous stirring. Dichloromethane (150 ml) was added and the material was shaken in a reparatory funnel. The organic phase was collected and shaken with an equal volume of brine. The aqueous phases were back extracted with dichloromethane (2×120 ml). The organics were combined, dried over magnesium sulfate, filtered and concentrated in vacuo. The crude product was purified by preparative thin layer chromatography (2 plates), eluting first with 1% methanol/dichloromethane and then re-developing the plate with 25% ethyl acetate/hexane. The product band was collected, providing the desired product as a light yellow-white solid (287 mg). (M+H)$^+$=242/244 m/e.

Step 4. Preparation of [6-(6-Chloro-quinolin-8-ylamino)-pyridin-3-yl]-morpholin-4-yl-methanone

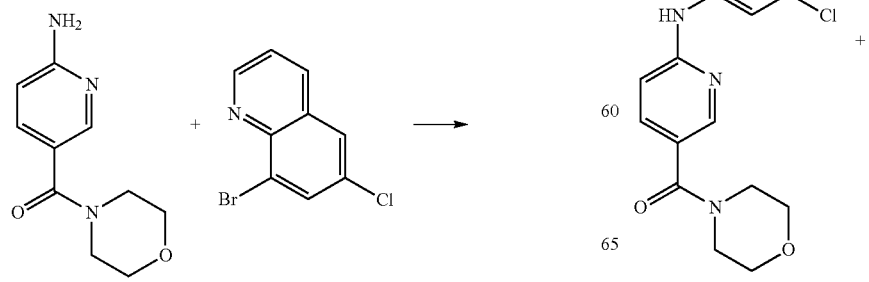

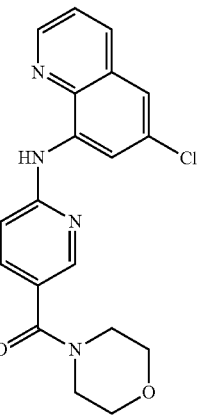

A mixture of 8-bromo-6-chlorquinoline (140 mg, 0.56 mmol), (6-aminopyrdin-3-yl)(morpholino)methanone (92 mg, 0.44 mmol), xantphos (38.5 mg, 0.067 mmol) and cesium carbonate was taken up in dry dioxane (6.5 ml). The reaction flask is evacuated and back-filled with argon (repeated 5 times). Tris(dibenzylidenacetone)palladium (0) (31 mg, 0.033 mmol) was added and the flask was evacuated and back-filled with argon (repeated 3 times). The material was heated to 90° C. (oil bath) under argon for 14 hours. The reaction mixture was cooled to ambient temperature and filtered through a short plug of celite, rinsing well with dioxane. The solvent was removed and the resulting residue loaded onto 2 preparative thin layer chromatography plates. The plates were eluted with 75% ethyl acetate/hexane and the product band collected. This provided the desired product as a light brown viscous oil (180 mg).

(M+H)$^+$=369 m/e.

Step 5. Preparation of acetic acid 2-(6-tert-butyl-8-fluoro-1-oxo-1H-phthalazin-2-yl)-6-{8-[5-(morpholine-4-carbonyl)-pyridin-2-ylamino]-quinolin-6-yl}-benzyl ester

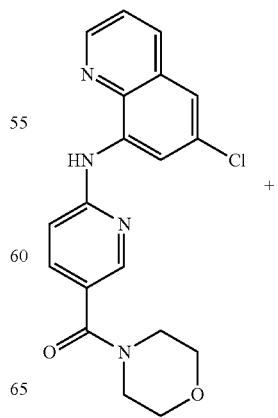
+

85

-continued

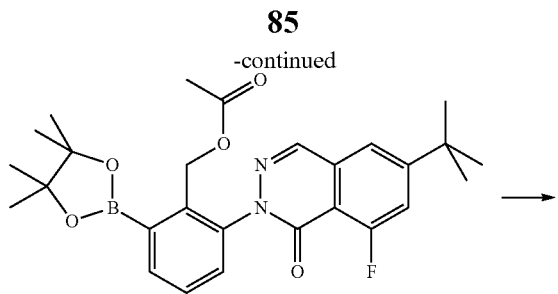

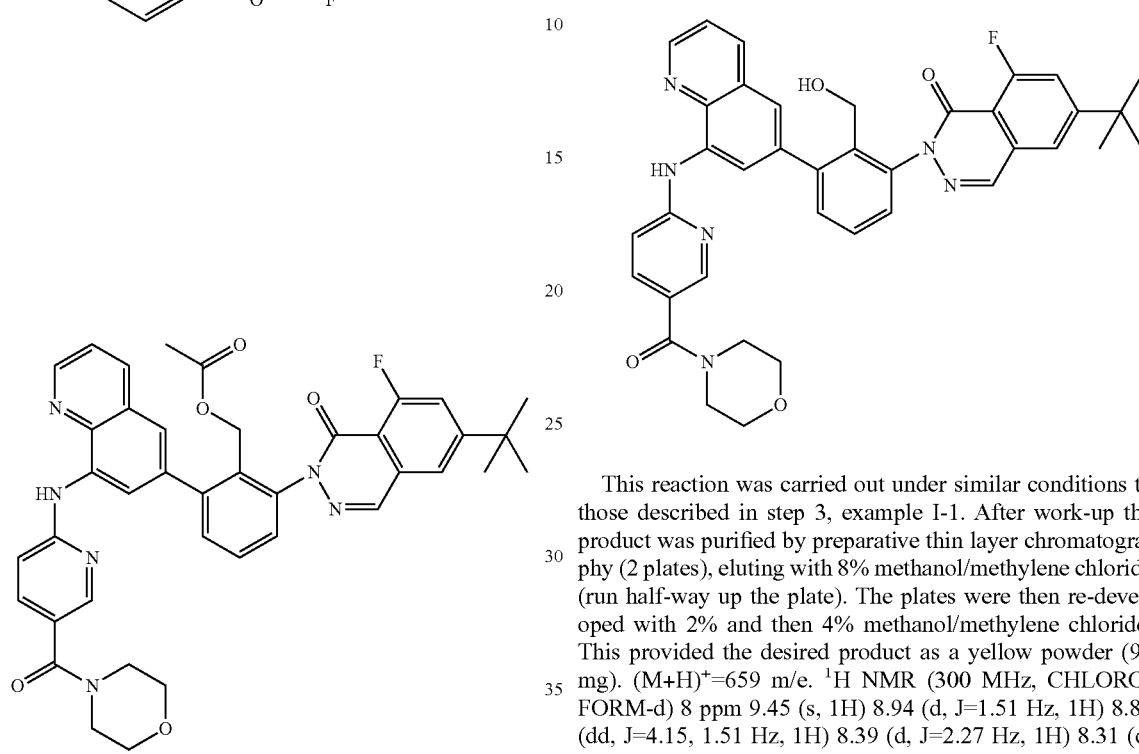

In a 25 ml round bottom flask containing 2-(6-tert-butyl-8-fluoro-1-oxophthalazin-2(1H)-yl)-6-(4,4,5,5-tetramethyl-1,3,2-dioxaborolan-2-yl)benzyl acetate (563 mg, 683 µmol, Eq: 1.4), (6-(6-chloroquinolin-8-ylamino)pyridin-3-yl)(morpholino)methanone (180 mg, 488 µmol, Eq: 1.00), X-PHOS (34.9 mg, 73.2 µmol) and potassium phosphate (228 mg, 1.07 mmol) was added BuOH (7 mL) and $H_2O$ (1.65 mL). The flask was evacuated and backfilled with argon before addition of $Pd(dba)_2$ (19.6 mg, 34.2 µmol). The flask was evacuated and backfilled with argon again and heated at 110° C. for 2.5 hrs. LC/MS showed the presence of desired product as a mixture with 6-tert-butyl-8-fluoro-2-(2-hydroxymethyl-3-{8-[5-(morpholine-4-carbonyl)-pyridin-2-ylamino]-quinolin-6-yl}-phenyl)-2H-phthalazin-1-one. The reaction mixture was cooled to ambient temperature, diluted with 35 ml water and 35 ml EtOAc and shaken. The EtOAc phase was collected and washed with an equal volume of brine. The aqueous phase was back-extracted with 2×30 ml EtOAc. The combined organic extract was dried ($MgSO_4$), and concentrated in vacuo. The crude product was purified by preparative thin layer chromatography (3 plates), eluting with 2% methanol/methylene chloride to provide the desired product (together with some 6-tert-butyl-8-fluoro-2-(2-hydroxymethyl-3-{8-[5-(morpholine-4-carbonyl)-pyridin-2-ylamino]-quinolin-6-yl}-phenyl)-2H-phthalazin-1-one) as a light brown foamy solid (310 mg).

$(M+H)^+ = 701$ m/e.

86

Example 13

Step 6. Preparation of 6-tert-butyl-8-fluoro-2-(2-hydroxymethyl-3-{8-[5-(morpholine-4-carbonyl)-pyridin-2-ylamino]-quinolin-6-yl}-phenyl)-2H-phthalazin-1-one This reaction was carried out under similar conditions to those described in step 3, example I-1. After work-up the product was purified by preparative thin layer chromatography (2 plates), eluting with 8% methanol/methylene chloride (run half-way up the plate). The plates were then re-developed with 2% and then 4% methanol/methylene chloride. This provided the desired product as a yellow powder (94 mg). $(M+H)^+ = 659$ m/e. $^1H$ NMR (300 MHz, CHLOROFORM-d) δ ppm 9.45 (s, 1H) 8.94 (d, J=1.51 Hz, 1H) 8.85 (dd, J=4.15, 1.51 Hz, 1H) 8.39 (d, J=2.27 Hz, 1H) 8.31 (d, J=2.64 Hz, 1H) 8.23 (dd, J=8.31, 1.51 Hz, 1H) 7.74 (dd, J=8.69, 2.27 Hz, 1H) 7.65 (d, J=1.51 Hz, 1H) 7.60-7.63 (m, 1H) 7.55-7.59 (m, 2H) 7.50-7.54 (m, 1H) 7.49 (d, J=4.15 Hz, 1H) 7.44 (dd, J=7.55, 1.89 Hz, 1H) 7.11 (d, J=8.31 Hz, 1H) 4.44 (d, J=6.42 Hz, 2H) 3.65-3.84 (m, 8H) 3.61 (t, J=6.80 Hz, 1H) 1.44 (s, 9H).

Biological Assay Data

Bruton's Tyrosine Kinase (Btk) Inhibition Assay

The assay is a capture of radioactive $^{33}P$ phosphorylated product through filtration. The interactions of Btk, biotinylated $SH_2$ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 µm hydrophilic PVDF filter plates (Millipore). Concentrations reported here are final assay concentrations: 10-100 µM compounds in DMSO (Burdick and Jackson), 5-10 nM Btk enzyme (His-tagged, full-length), 30 µM peptide substrate (Biotin-Aca-AAAEEIYGEI-$NH_2$), 100 µM ATP (Sigma), 8 mM imidazole (Sigma, pH 7.2), 8 mM glycerol-2-phosphate (Sigma), 200 µM EGTA (Roche Diagnostics), 1 mM $MnCl_2$ (Sigma), 20 mM $MgCl_2$ (Sigma), 0.1 mg/ml BSA (Sigma), 2 mM DTT (Sigma), 1 µCi $^{33}P$ ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

IC$_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 µM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, MnCl$_2$, MgCl$_2$, BSA).
2) Bead preparation
   a.) rinse beads by centrifuging at 500 g
   b.) reconstitute the beads with PBS and EDTA to produce a 20% bead slurry
3) Pre-incubate reaction mix without substrate (assay buffer, DTT, ATP, $^{33}$P ATP) and mix with substrate (assay buffer, DTT, ATP, $^{33}$P ATP, peptide substrate) 30° C. for 15 min.
4) To start assay, pre-incubate 10 µL Btk in enzyme buffer (imidazole, glycerol-2-phosphate, BSA) and 10 µL of test compounds for 10 min at RT.
5) Add 30 µL reaction mixture without or with substrate to Btk and compounds.
6) Incubate 50 µL total assay mix for 30 min at 30° C.
7) Transfer 40 µL of assay to 150 µL bead slurry in filter plate to stop reaction.
8) Wash filter plate after 30 min, with following steps
   a. 3×250 µL NaCl
   b. 3×250 µL NaCl containing 1% phosphoric acid
   c. 1×250 µL H$_2$O
9) Dry plate for 1 h at 65° C. or overnight at RT
10) Add 50 µL microscint-20 and count $^{33}$P cpm on scintillation counter.

Calculate percent activity from raw data in cpm percent activity=(sample—$bkg$)/(total activity–$bkg$)×100

Calculate IC$_{50}$ from percent activity, using one-site dose response sigmoidal model $y=A+((B-A)/(1+((x/C)^D)))$ x=cmpd conc, y=% activity, A=min, B=max, C=IC$_{50}$, D=1 (hill slope)

Inhibition of B Cell Activation in Whole Blood Measured by CD69 Expression

A procedure to test the ability of Btk inhibitors to suppress B cell receptor-mediated activation of B cells in human blood is as follows:

Human whole blood (HWB) is obtained from healthy volunteers, with the following restrictions: 24 hr drug-free, non-smokers. Blood is collected by venipuncture into Vacutainer tubes anticoagulated with sodium heparin. Test compounds are diluted to ten times the desired starting drug concentration in PBS (20×), followed by three-fold serial dilutions in 10% DMSO in PBS to produce a nine point dose-response curve. 5.5 µl of each compound dilution is added in duplicate to a 2 ml 96-well V bottom plate (Analytical Sales and Services, #59623-23); 5.5 µl of 10% DMSO in PBS is added to control and no-stimulus wells. HWB (100 µl) is added to each well, and after mixing the plates are incubated at 37 C, 5% CO$_2$, 100% humidity for 30 minutes. Goat F(ab')2 anti-human IgM (Southern Biotech, #2022-14) (10 µl of a 500 µg/ml solution, 50 µg/ml final concentration) is added to each well (except the no-stimulus wells) with mixing and the plates are incubated for an additional 20 hours.

At the end of the 20 hour incubation, samples are incubated with florescent-probe-labeled anti-bodies (15 µl PE Mouse anti-Human CD20, BD Pharmingen, #555623, and/or 20 ul APC Mouse anti-Human CD69, BD Pharmingen #555533) for 30 minutes, at 37 C, 5% CO$_2$, 100% humidity. Included are induced control, unstained and single stains for compensation adjustments and initial voltage settings. Samples are then lysed with 1 ml of 1× Pharmingen Lyse Buffer (BD Pharmingen #555899), and plates are centrifuged at 1800 rpm for 5 minutes. Supernatants are removed via suction and the remaining pellets are lysed again with another 1 ml of 1× Pharmingen Lyse Buffer, and plates are spun down as before. Supernatants are aspirated and remaining pellets are washed in FACs buffer (PBS+1% FBS). After a final spin, the supernatants are removed and pellets are resuspended in 180 µl of FACs buffer. Samples are transferred to a 96 well plate suitable to be run on the HTS 96 well system on the BD LSR II flow cytometer.

Using appropriate excitation and emission wavelengths for the fluorophores used, data are acquired and percent positive cell values are obtained using Cell Quest Software. Results are initially analyzed by FACS analysis software (Flow Jo). The IC50 for test compounds is defined as the concentration which decreases by 50% the percentage of CD69-positive cells that are also CD20-positive after stimulation by anti-IgM (average of 8 control wells, after subtraction of the average of 8 wells for the no-stimulus background). The IC50 values are calculated using XLfit software version 3, equation 201.

Representative compound data for this assay are listed below in Table II.

TABLE II

| Compound | HWB IC50 (µM) |
|---|---|
| I-1 | 0.35 |
| I-2 | 0.077 |
| I-3 | 0.04 |
| I-4 | 0.013 |
| I-5 | 0.89 |
| I-6 | 0.48 |
| I-7 | 0.112 |
| I-8 | 2.27 |
| I-9 | 1.04 |
| I-10 | 0.142 |
| I-11 | 0.072 |
| I-12 | 2.5 |
| I-13 | >5 |

Inhibition of B-Cell Activation

B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of 0.5×10$^6$/mL in tissue culture flasks. On day of assay, cells are counted and set at a concentration of 1×10$^6$/mL1 in growth media supplemented with 1 μM FLUO-3AM (TefLabs Cat-No. 0116, prepared in anhydrous DMSO and 10% Pluronic acid) in a tissue culture flask, and incubated at 37° C. (4% CO$_2$) for one h. To remove extracellular dye, cells were collected by centrifugation (5 min, 1000 rpm), resuspended in FLIPR buffer (described below) at 1×10$^6$ cells/mL and then dispensed into 96-well poly-D-lysine coated black/clear plates (BD Cat-No. 356692) at 1×10$^5$ cells per well. Test compounds were added at various concentrations ranging from 100 μM to 0.03 μM (7 concentrations, details below), and allowed to incubate with cells for 30 min at RT. Ramos cell Ca$^{2+}$ signaling was stimulated by the addition of 10 μg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM CaCl$_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 μM, 24 μL of 10 mM compound stock solution (made in DMSO) is added directly to 576 μL of FLIPR buffer. The test compounds are diluted in FLIPR Buffer (using Biomek 2000 robotic pipettor) resulting in the following dilution scheme: vehicle, $1.00 \times 10^{-4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The IC$_{50}$ was determined using a non-linear curve fit (GraphPad Prism software).

Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring: 1=swelling and/or redness of paw or one digit.

2=swelling in two or more joints.

3=gross swelling of the paw with more than two joints involved.

4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Rat In Vivo Asthma Model

Male Brown-Norway rats are sensitized i.p. with 100 μg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100 μl) is determined by Coulter Counter. For differential leukocyte counts, 50-200 μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leucocyte count in the BAL of OA sensitized and challenged rats as compared to control levels.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I,

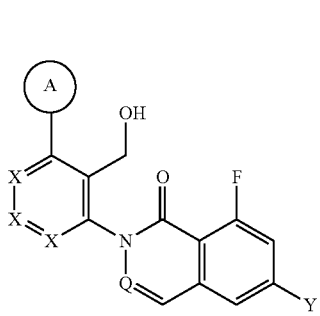

wherein:
X is CH;
Q is N;
A is

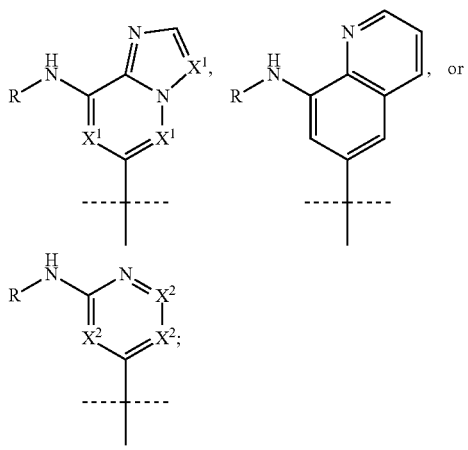

wherein:
one $X^1$ is N and the rest are CH, or each $X^1$ is CH;
one $X^2$ is N and the rest are CH, or each $X^2$ is CH, or one $X^2$ is N and the rest are CH or $CNH_2$;
R is H, —$R^1$, —$R^1$—$R^2$—$R^3$, —$R^1$—$R^3$, or —$R^2$—$R^3$;
$R^1$ is aryl or heteroaryl;
$R^2$ is —C(=O) or $C(R^{2'})_2$;
each $R^{2'}$ is independently H or lower alkyl;
$R^3$ is H or $R^4$;
$R^4$ is heterocycloalkyl optionally substituted with lower alkyl;
Y is lower alkyl;
or a pharmaceutically acceptable salt thereof.

2. The compound of claim 1, wherein A is

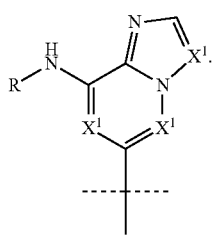

3. The compound of claim 2, wherein A is

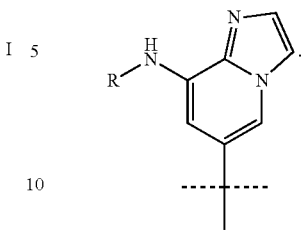

4. The compound of claim 2, wherein A is

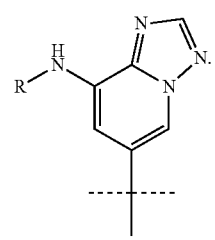

5. The compound of claim 2, wherein A is

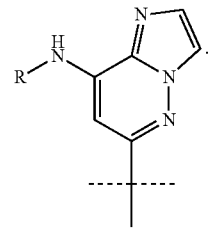

6. The compound of claim 2, wherein A is

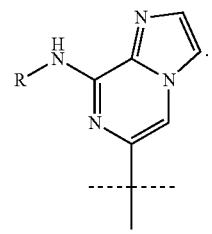

7. The compound of claim 1, wherein A is

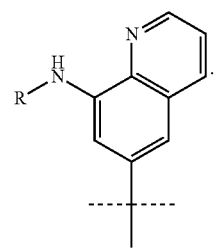

8. The compound of claim 1, wherein A is

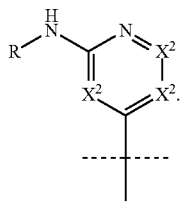

9. The compound of claim 8, wherein A is

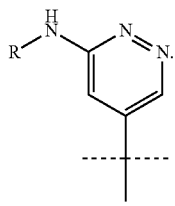

10. The compound of claim 8, wherein A is

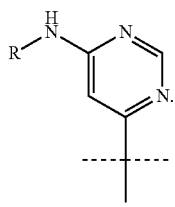

11. The compound of claim 1, wherein
R is —R$^1$—R$^2$—R$^3$.

12. The compound of claim 11, wherein R$^1$ is pyridyl, each X is CH, and Q is N.

13. The compound of claim 12, wherein R$^2$ is —C(=O) or CH$_2$.

14. The compound of claim 1, wherein
R is —R$^1$—R$^3$, each X is CH, and Q is N.

15. The compound of claim 1 selected from the group consisting of:
 6-tert-Butyl-8-fluoro-2-(2-hydroxymethyl-3-{8-[5-(morpholine-4-carbonyl)-pyridin-2-ylamino]-[1,2,4]triazolo[1,5-c]pyridin-6-yl}-phenyl)-2H-phthalazin-1-one;
 6-tert-Butyl-8-fluoro-2-(2-hydroxymethyl-3-{8-[5-(morpholine-4-carbonyl)-pyridin-2-ylamino]-imidazo[1,2-b]pyridazin-6-yl}-phenyl)-2H-phthalazin-1-one;
 6-tert-Butyl-8-fluoro-2-(2-hydroxymethyl-3-{8-[5-(4-isopropyl-piperazin-1-yl)-pyridin-2-ylamino]-imidazo[1,2-b]pyridazin-6-yl}-phenyl)-2H-phthalazin-1-one;
 6-tert-Butyl-8-fluoro-2-(2-hydroxymethyl-3-{8-[5-(4-methyl-piperazin-1-ylmethyl)-pyridin-2-ylamino]-imidazo[1,2-b]pyridazin-6-yl}-phenyl)-2H-phthalazin-1-one;
 6-tert-Butyl-8-fluoro-2-(2-hydroxymethyl-3-{6-[5-(morpholine-4-carbonyl)-pyridin-2-ylamino]-pyridazin-4-yl}-phenyl)-2H-phthalazin-1-one;
 6-tert-Butyl-8-fluoro-2-(2-hydroxymethyl-3-{2-[5-(morpholine-4-carbonyl)-pyridin-2-ylamino]-pyridin-4-yl}-phenyl)-2H-phthalazin-1-one;
 6-tert-Butyl-8-fluoro-2-(2-hydroxymethyl-3-{8-[4-(morpholine-4-carbonyl)-phenylamino]-imidazo[1,2-c]pyrazin-6-yl}-phenyl)-2H-phthalazin-1-one;
 6-tert-Butyl-8-fluoro-2-(2-hydroxymethyl-3-{8-[4-(1-methyl-piperidin-4-yl)-phenylamino]-imidazo[1,2-c]pyrazin-6-yl}-phenyl)-2H-phthalazin-1-one;
 6-tert-Butyl-8-fluoro-2-(2-hydroxymethyl-3-{8-[4-(morpholine-4-carbonyl)-phenylamino]-imidazo[1,2-c]pyridin-6-yl}-phenyl)-2H-phthalazin-1-one;
 6-tert-Butyl-8-fluoro-2-(2-hydroxymethyl-3-{8-[5-(morpholine-4-carbonyl)-pyridin-2-ylamino]-imidazo[1,2-c]pyridin-6-yl}-phenyl)-2H-phthalazin-1-one;
 6-tert-Butyl-8-fluoro-2-{2-hydroxymethyl-3-[8-(1'-methyl-1',2',3',4',5',6'-hexahydro-[3,4']bipyridinyl-6-ylamino)-imidazo[1,2-c]pyridin-6-yl]-phenyl}-2H-phthalazin-1-one;
 6-tert-Butyl-8-fluoro-2-(2-hydroxymethyl-3-{6-[5-(morpholine-4-carbonyl)-pyridin-2-ylamino]-pyrimidin-4-yl}-phenyl)-2H-phthalazin-1-one; and
 6-tert-Butyl-8-fluoro-2-(2-hydroxymethyl-3-{8-[5-(morpholine-4-carbonyl)-pyridin-2-ylamino]-quinolin-6-yl}-phenyl)-2H-phthalazin-1-one.

16. A method for treating an inflammatory and/or autoimmune condition comprising administering to a patient in need thereof a therapeutically effective amount of the Btk inhibitor compound of claim 1.

17. A method for treating rheumatoid arthritis comprising administering to a patient in need thereof a therapeutically effective amount of the Btk inhibitor compound of claim 1.

18. A method for treating asthma comprising administering to a patient in need thereof a therapeutically effective amount of the Btk inhibitor compound of claim 1.

19. A pharmaceutical composition comprising the Btk inhibitor compound of claim 1.

20. A pharmaceutical composition comprising the Btk inhibitor compound of claim 1, admixed with at least one pharmaceutically acceptable carrier, excipient or diluent.

* * * * *